United States Patent
Abe et al.

(10) Patent No.: US 12,139,459 B2
(45) Date of Patent: Nov. 12, 2024

(54) ENHANCER OF FERTILIZATION FUNCTION OF SPERM

(71) Applicants: TOHOKU UNIVERSITY, Miyagi (JP); KAKE EDUCATIONAL INSTITUTION, Okayama (JP)

(72) Inventors: Takaaki Abe, Miyagi (JP); Nobuo Yaegashi, Miyagi (JP); Masahito Tachibana, Miyagi (JP); Kenichiro Hayashi, Okayama (JP)

(73) Assignees: TOHOKU UNIVERSITY, Miyagi (JP); KAKE EDUCATIONAL INSTITUTION, Okayama (JP)

( * ) Notice: Subject to any disclaimer, the term of this patent is extended or adjusted under 35 U.S.C. 154(b) by 1010 days.

(21) Appl. No.: 15/734,579

(22) PCT Filed: Jun. 4, 2019

(86) PCT No.: PCT/JP2019/022082
§ 371 (c)(1),
(2) Date: Apr. 28, 2021

(87) PCT Pub. No.: WO2019/235455
PCT Pub. Date: Dec. 12, 2019

(65) Prior Publication Data
US 2022/0106270 A1    Apr. 7, 2022

(30) Foreign Application Priority Data

Jun. 5, 2018  (JP) ................. 2018-107827

(51) Int. Cl.
| | | |
|---|---|---|
| *C07D 209/12* | (2006.01) | |
| *C07D 209/18* | (2006.01) | |
| *C07D 209/20* | (2006.01) | |
| *C07D 401/06* | (2006.01) | |
| *C12N 5/073* | (2010.01) | |
| *C12N 5/075* | (2010.01) | |
| *C12N 5/076* | (2010.01) | |

(52) U.S. Cl.
CPC ......... *C07D 209/12* (2013.01); *C07D 209/18* (2013.01); *C07D 209/20* (2013.01); *C07D 401/06* (2013.01); *C12N 5/0604* (2013.01); *C12N 5/0609* (2013.01); *C12N 5/061* (2013.01); *C12N 2500/30* (2013.01); *C12N 2501/999* (2013.01)

(58) Field of Classification Search
None
See application file for complete search history.

(56) References Cited

U.S. PATENT DOCUMENTS

2015/0353489 A1* 12/2015 Abe .................. A61P 1/16
548/494

FOREIGN PATENT DOCUMENTS

| JP | 2015-189670 A | 11/2015 |
|---|---|---|
| WO | 2014/080640 | 5/2014 |

OTHER PUBLICATIONS

Tug et al, Archives of Gynecology and Obstetrics, vol. 281 pp. 933-938 (Year: 2010).*
Nakada, K. et al., Proc Natl Acad Sci U S A. (2006) 103:15148-15153.

* cited by examiner

*Primary Examiner* — Zinna Northington Davis
(74) *Attorney, Agent, or Firm* — Edwin S. Flores; Daniel J. Chalker; Chalker Flores, LLP

(57) ABSTRACT

An object of the present invention is to provide an agent for enhancing fertilization function of a mammal sperm, which comprises a low molecular compound which can be produced relatively easily and inexpensively as an active ingredient, and a method for enhancing fertilization function of a mammal sperm and a method for preparing a mammal fertilized egg, which use a low molecular compound which can be produced relatively easily and inexpensively. An agent comprising one or more compounds selected from the group consisting of compounds of the following formula $(I_0)$, formula (II), and formula (III), and physiologically acceptable salts thereof when $R^3$ is OH is used as an agent for enhancing fertilization function of a mammal sperm.

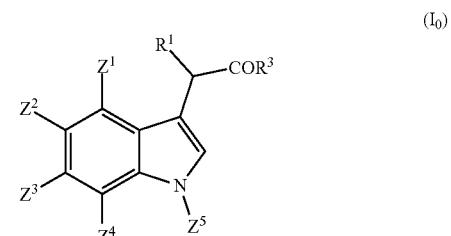

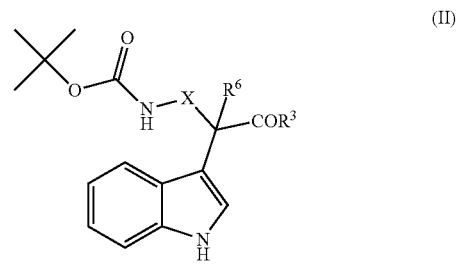

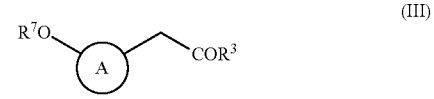

6 Claims, No Drawings

ENHANCER OF FERTILIZATION FUNCTION OF SPERM

CROSS-REFERENCE TO RELATED APPLICATIONS

This application is the National Stage of International Application No. PCT/JP2019/022082, filed on Jun. 4, 2019 claiming the priority of JP 2018-107827, filed on Jun. 5, 2018, the content of each of which is incorporated by reference herein.

TECHNICAL FIELD

The present invention relates to an agent for enhancing fertilization function of a mammal sperm, a method for enhancing fertilization function of a mammal sperm, and a method for preparing a mammal fertilized egg.

BACKGROUND ART

In Japan, one out of four married couples reportedly has an infertility problem due to the influence of delayed marriage or late birth. Hence, the practice of general treatment of infertility by intrauterine insemination (IUI) as well as assisted reproductive technology (ART) such as in vitro fertilization (IVF) or intracytoplasmic sperm injection (ICSI) is on the increase.

According to WHO (World Health Organization), males are involved in about 50% cases including 24% "male" factors alone and both male and female factors among the causes of infertility. However, Japanese treatment of infertility is weighted toward females, and measures against the male factors have rarely been made so far.

Sperms with reduced mobility have been confirmed in male infertility cases, and the sperms have been reported to have the mitochondrial genome having a mutation. It has also been reported using mice having the mutagenized mitochondrial genome that decreased function of mitochondrion is associated with male infertility (Non-Patent Document 1).

On the other hand, the present inventors have reported that the compound group of the present invention, which will be described later, has an effect of enhancing expression of erythropoietin and a therapeutic effect of mitochondrial disease (Patent Document 1) and an effect of suppressing organ fibrosis (Patent Document 2). However, it has not been known so far that the compound group of the present invention has the effect of enhancing fertilization function of a mammal sperm.

PRIOR ART DOCUMENTS

Patent Documents

Patent Document 1: WO 2014/080640
Patent Document 2: Japanese unexamined Patent Application Publication No. 2015-189670

Non-Patent Document

Non-Patent Document 1: Nakada, K. et al., Proc Natl Acad Sci USA. (2006) 103: 15148-15153

SUMMARY OF THE INVENTION

Object to be Solved by the Invention

An object of the present invention is to provide an agent for enhancing fertilization function of a mammal sperm, which comprises a low molecular compound which can be produced relatively easily and inexpensively as an active ingredient, and a method for enhancing fertilization function of a mammal sperm and a method for preparing a mammal fertilized egg, which use a low molecular compound which can be produced relatively easily and inexpensively.

Means to Solve the Object

The present inventors are continuing diligent studies to solve the object. In the process, the present inventors found that the compound group of the present invention described below has an effect of effectively enhancing fertilization function even on a mammal sperm having decreased fertilization function, and have completed the present invention.

Specifically, the present invention is as follows:
[1] An agent for enhancing fertilization function of a mammal sperm, comprising one or more compounds selected from the group consisting of compounds of the following formula ($I_0$), formula (II), and formula (III), and physiologically acceptable salts thereof when $R^3$ is OH:

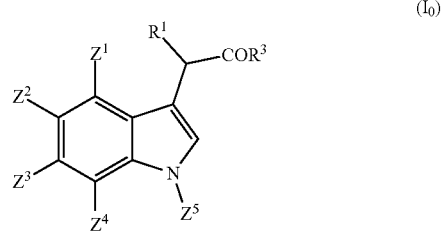

(I₀)

[wherein $R^1$ is a benzoylmethyl group whose benzene ring is unsubstituted or a benzoylmethyl group whose benzene ring is substituted by an alkyl group having 1 to 7 carbon atoms, an alkoxyl group having 1 to 7 carbon atoms, fluorine, and/or chlorine; an unsubstituted or fluorine-substituted linear or branched alkyl group having 4 to 6 carbon atoms; or phenyl group- or cyclopentyl group-substituted methylene or ethylene; wherein the phenyl group is optionally further substituted by one or more phenyl groups, $Z^1$, $Z^2$, $Z^3$ and $Z^4$ are the same or different and each is a hydrogen atom, a halogen atom, a C1 to C6 alkyl group, a C2 to C6 alkenyl group, a C2 to C6 alkynyl group, an organic oxy group represented by $OR^8$, $R^8$ is a C1 to C7 alkyl group, a C2 to C6 alkenyl group or a C2 to C6 alkynyl group, $Z^5$ is a hydrogen atom or a C1 to C6 alkyl group, $R^3$ is any group selected from OH, $OR^4$, $NHR^4$, and $NR^4R^5$, and $R^4$ and $R^5$ are the same or different and each is a substituted or unsubstituted alkyl group having 1 to 4 carbon atoms]

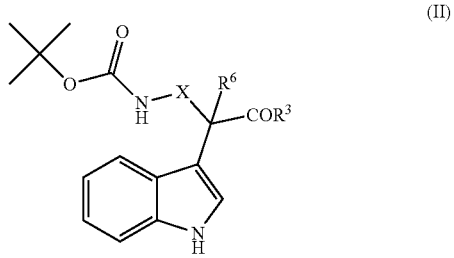

(II)

[wherein $R^6$ is hydrogen or a methyl group, X is an alkylene group having 4 to 6 carbon atoms or an ether group having 4 carbon atoms, $R^3$ is any group selected from OH, $OR^4$, $NHR^4$, and $NR^4R^5$, and $R^4$ and $R^5$ are the same or different and each is a substituted or unsubstituted alkyl group having 1 to 4 carbon atoms]

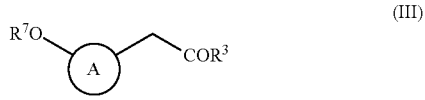

(III)

[wherein A is indole or naphthalene, and when A is indole, positions 3 and 5 of the indole are substituted by an acetic acid group and $R^7O$, respectively, and when A is naphthalene, positions 1 and 7 of the naphthalene are substituted by an acetic acid group and $R^7O$, respectively, $R^7$ is an alkyl group having 1 to 5 carbon atoms or a benzyl group, wherein the benzene ring of the benzyl group is optionally substituted by one or more alkyl groups having 1 to 3 carbon atoms or alkoxyl groups having 1 to 3 carbon atoms, $R^3$ is any group selected from OH, $OR^4$, $NHR^4$, and $NR^4R^5$, and $R^4$ and $R^5$ are the same or different and each is a substituted or unsubstituted alkyl group having 1 to 4 carbon atoms]

[2] The agent according to [1], wherein the compound is a compound of the following formula (I-2) or a physiologically acceptable salt thereof:

Formula (I-2)

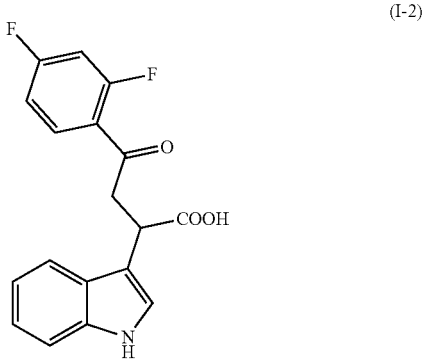

(I-2)

[3] A method for enhancing fertilization function of a mammal sperm, comprising step (a) of transferring at least one collected mammal sperm into a physiological aqueous solution containing one or more compounds selected from the group consisting of compounds of the following formula ($I_0$), formula (II), and formula (III), and physiologically acceptable salts thereof when $R^3$ is OH:

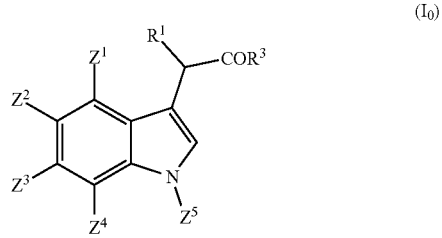

($I_0$)

[wherein $R^1$ is a benzoylmethyl group whose benzene ring is unsubstituted or a benzoylmethyl group whose benzene ring is substituted by an alkyl group having 1 to 7 carbon atoms, an alkoxyl group having 1 to 7 carbon atoms, fluorine, and/or chlorine; an unsubstituted or fluorine-substituted linear or branched alkyl group having 4 to 6 carbon atoms; or phenyl group- or cyclopentyl group-substituted methylene or ethylene; wherein the phenyl group is optionally further substituted by one or more phenyl groups, $Z^1$, $Z^2$, $Z^3$ and $Z^4$ are the same or different and each is a hydrogen atom, a halogen atom, a C1 to C6 alkyl group, a C2 to C6 alkenyl group, a C2 to C6 alkynyl group, an organic oxy group represented by $OR^8$, $R^8$ is a C1 to C7 alkyl group, a C2 to C6 alkenyl group or a C2 to C6 alkynyl group, $Z^5$ is a hydrogen atom or a C1 to C6 alkyl group, $R^3$ is any group selected from OH, $OR^4$, $NHR^4$, and $NR^4R^5$, and $R^4$ and $R^5$ are the same or different and each is a substituted or unsubstituted alkyl group having 1 to 4 carbon atoms],

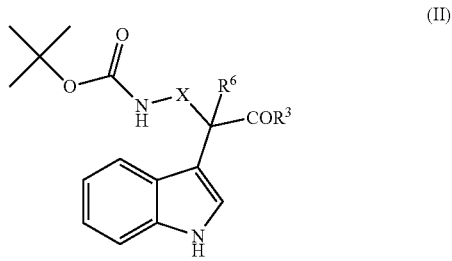

(II)

[wherein $R^6$ is hydrogen or a methyl group, X is an alkylene group having 4 to 6 carbon atoms or an ether group having 4 carbon atoms, $R^3$ is any group selected from OH, $OR^4$, $NHR^4$, and $NR^4R^5$, and $R^4$ and $R^5$ are the same or different and each is a substituted or unsubstituted alkyl group having 1 to 4 carbon atoms], and

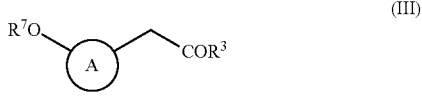

(III)

[wherein A is indole or naphthalene, and when A is indole, positions 3 and 5 of the indole are substituted by an acetic acid group and $R^7O$, respectively, and when A is naphthalene, positions 1 and 7 of the naphthalene are substituted by an acetic acid group and $R^7O$, respectively, $R^7$ is an alkyl group having 1 to 5 carbon atoms or a benzyl group, wherein the benzene ring of the benzyl group is optionally substituted by one or more alkyl groups having 1 to 3 carbon atoms or alkoxyl groups having 1 to 3 carbon atoms, $R^3$ is any group selected from OH, $OR^4$, $NHR^4$, and $NR^4R^5$, and $R^4$ and $R^5$ are the same or different and each is a substituted or unsubstituted alkyl group having 1 to 4 carbon atoms].

[4] The method for enhancing fertilization function according to [3], wherein the compound is a compound of the following formula (I-2) or a physiologically acceptable salt thereof:

Formula (I-2)

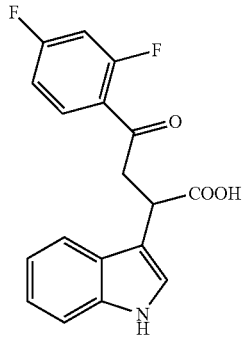
(I-2)

[5] A method for preparing a mammal fertilized egg, comprising step (b-1) of culturing a mammal sperm obtained by an enhancement method according to [3] or [4] in a culture medium containing at least one collected mammal ovum.

[6] A method for preparing a mammal fertilized egg, comprising step (b-2) of culturing at least one collected mammal sperm and at least one collected mammal ovum in a culture medium containing one or more compounds selected from the group consisting of compounds of the following formula $(I_0)$, formula (II), and formula (III), and physiologically acceptable salts thereof when $R^3$ is OH:

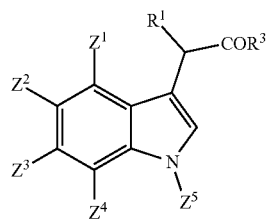
$(I_0)$

[wherein $R^1$ is a benzoylmethyl group whose benzene ring is unsubstituted or a benzoylmethyl group whose benzene ring is substituted by an alkyl group having 1 to 7 carbon atoms, an alkoxyl group having 1 to 7 carbon atoms, fluorine, and/or chlorine; an unsubstituted or fluorine-substituted linear or branched alkyl group having 4 to 6 carbon atoms; or phenyl group- or cyclopentyl group-substituted methylene or ethylene; wherein the phenyl group is optionally further substituted by one or more phenyl groups, $Z^1$, $Z^2$, $Z^3$ and $Z^4$ are the same or different and each is a hydrogen atom, a halogen atom, a C1 to C6 alkyl group, a C2 to C6 alkenyl group, a C2 to C6 alkynyl group, an organic oxy group represented by $OR^8$, $R^8$ is a C1 to C7 alkyl group, a C2 to C6 alkenyl group or a C2 to C6 alkynyl group, $Z^5$ is a hydrogen atom or a C1 to C6 alkyl group, $R^3$ is any group selected from OH, $OR^4$, $NHR^4$, and $NR^4R^5$, and $R^4$ and $R^5$ are the same or different and each is a substituted or unsubstituted alkyl group having 1 to 4 carbon atoms],

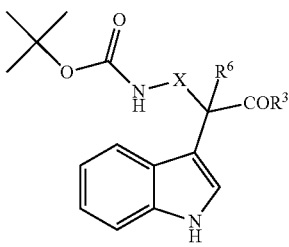
(II)

[wherein $R^6$ is hydrogen or a methyl group, X is an alkylene group having 4 to 6 carbon atoms or an ether group having 4 carbon atoms, $R^3$ is any group selected from OH, $OR^4$, $NHR^4$, and $NR^4R^5$, and $R^4$ and $R^5$ are the same or different and each is a substituted or unsubstituted alkyl group having 1 to 4 carbon atoms], and

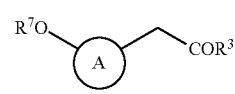
(III)

[wherein A is indole or naphthalene, and when A is indole, positions 3 and 5 of the indole are substituted by an acetic acid group and $R^7O$, respectively, and when A is naphthalene, positions 1 and 7 of the naphthalene are substituted by an acetic acid group and $R^7O$, respectively, $R^7$ is an alkyl group having 1 to 5 carbon atoms or a benzyl group, wherein the benzene ring of the benzyl group is optionally substituted by one or more alkyl groups having 1 to 3 carbon atoms or alkoxyl groups having 1 to 3 carbon atoms, $R^3$ is any group selected from OH, $OR^4$, $NHR^4$, and $NR^4R^5$, and $R^4$ and $R^5$ are the same or different and each is a substituted or unsubstituted alkyl group having 1 to 4 carbon atoms].

[7] The method for preparing a mammal fertilized egg according to [6], wherein the compound is a compound of the following formula (I-2) or a physiologically acceptable salt thereof:

Formula (I-2)

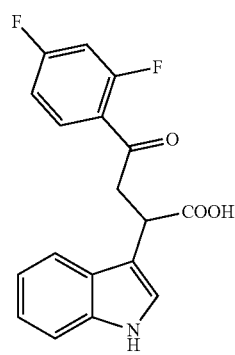
(I-2)

An alternative embodiment of the present invention can include, for example, one or more compounds selected from the compound group of the present invention for use as an agent for enhancing fertilization function of a mammal sperm; one or more compounds selected from the compound group of the present invention for use in enhancing fertilization function of a mammal sperm; and use of one or more compounds selected from the compound group of the present invention for producing an agent for enhancing fertilization function of a mammal sperm.

An alternative embodiment of the present invention can also include, for example, a method for increasing the fertilization efficiency and/or pregnancy efficiency of a female non-human mammal, comprising: step (a) of transferring at least one collected mammal sperm into a physiological aqueous solution containing one or more compounds selected from the compound group of the present invention, wherein the mammal sperm is a non-human mammal sperm; and step (p-1) of injecting the non-human mammal sperm obtained in the step (a) into the uterus of the female non-human mammal in the ovulatory phase (this process is referred to as intrauterine insemination [IUI]).

An alternative embodiment of the present invention can also include, for example, a method for increasing the fertilization efficiency and/or pregnancy efficiency of a female human, comprising: step (a) of transferring at least one collected mammal sperm into a physiological aqueous solution containing one or more compounds selected from the compound group of the present invention, wherein the mammal sperm is a human sperm; and step (p-2) of injecting the human sperm obtained in the step (a) into the uterus of the female human in the ovulatory phase.

Effect of the Invention

According to the present invention, fertilization function of a mammal sperm can be effectively enhanced, and decreased fertilization function of a sperm can be enhanced in the treatment of infertility caused by male factors (male infertility). Therefore, improvement in fertilization rate or pregnancy rate is expected. Moreover, the compound group of the present invention is superior at the point that a low molecular weight compound which can be produced relatively easily and in high yield and useful as an active ingredient for enhancement of fertilization function of a mammal sperm, can be produced relatively easily and inexpensively.

Mode of Carrying Out the Invention

The agent for enhancing fertilization function of a mammal sperm of the present invention is an agent containing one or more compounds selected from the compound group of the present invention as an active ingredient for limited use that is "for enhancing fertilization function of a mammal sperm" (hereinafter, it is sometimes referred to as "enhancer of the present invention").

The method for enhancing fertilization function of a mammal sperm of the present invention is not particularly limited as long as the method comprises step (a) of transferring at least one collected mammal sperm into a physiological aqueous solution containing one or more compounds selected from the compound group of the present invention (hereinafter, it is sometimes referred to as "compound group-containing physiological aqueous solution of the present invention") (hereinafter, this method is sometimes referred to as "enhancement method of the present invention"). Preferably, the method further comprises the step of culturing the mammal sperm obtained in the step (a) before fertilization or semination (hereinafter, it is sometimes referred to as "pre-fertilization/pre-semination culture step"). The mammal sperm obtained by the enhancement method of the present invention can be used in an in vitro semination method (e.g., semination by in vitro fertilization) and an in vivo semination method (e.g., intrauterine insemination). Hence, the enhancement method of the present invention may further comprise, after the step (a) or after the pre-fertilization/pre-semination culture step, the step of injecting the obtained mammal sperm into at least one collected mammal ovum using a glass pipette (injection pipette for intracytoplasmic sperm injection) or the like under a microscope (hereinafter, it is sometimes referred to as "intracytoplasmic sperm injection step").

The method for preparing a mammal fertilized egg of the present invention is not particularly limited as long as the method is an in vitro method comprising step (b-1) of culturing a mammal sperm (semination by in vitro fertilization [IVF]) obtained by the enhancement method of the present invention in a culture medium containing at least one collected mammal ovum (hereinafter, it is sometimes referred to as "mammal ovum-containing culture medium") (hereinafter, this method is sometimes referred to as "preparation method 1 of the present invention"); or an in vitro method comprising step (b-2) of culturing at least one collected mammal sperm and at least one collected mammal ovum (semination) in a culture medium containing one or more compounds selected from the compound group of the present invention (hereinafter, it is sometimes referred to as "compound group-containing culture medium of the present invention") (hereinafter, this method is sometimes referred to as "preparation method 2 of the present invention"). The method may comprise the step of then culturing the mammal fertilized egg in vitro in order to confirm fertilization. The preparation method 1 of the present invention and the preparation method 2 of the present invention exclude in vitro fertilization in which a mammal sperm and a mammal ovum are spontaneously fertilized in a culture medium (semination by so-called in vitro fertilization) and a method for preparing a mammal fertilized egg, comprising the step of injecting a mammal sperm into at least one collected mammal ovum using a glass pipette (injection pipette for intracytoplasmic sperm injection) or the like under a microscope (intracytoplasmic sperm injection step).

The enhancement method of the present invention, the preparation method 1 of the present invention, and the preparation method 2 of the present invention exclude so-called medical practice by a physician, such as the step of implanting a fertilized egg into the female uterus (embryo transfer [ET]).

In this specification, "enhancement of fertilization function of a mammal sperm" means that increase in the fertilization rate of the mammal sperm with a mammal ovum owing to a factor such as enhancement of motility (more specifically, forward motility) of the mammal sperm by its enhanced mitochondrial function. An effect of enhancing fertilization function of a mammal sperm includes an effect of further enhancing a normal level of fertilization function as well as an effect of enhancing decreased fertilization function, for example, a decreased forward motion rate of a sperm compared with the lower limit value 32% of the forward motion rate of a healthy individual's sperm (see the document "WHO Laboratory Manual for the examination of semen, the 5th edition (published by the World Health Organization, translated by The Institute for Advanced Reproductive Medical Technology, 2010)"), to improve fertilization function. In other words, the enhancement method of the present invention enhances fertilization function of a mammal sperm, and as a result, there is a possibility that an infertile patient to which in vitro fertilization (IVF) is adapted can get pregnant by intrauterine insemination (IUI).

In recent years, fertility preservation treatment (oncofertility treatment) for cancer survivors of the AYA (adolescent and young adult) generation has received attention. However, freeze-thaw operation inevitably decreases sperm function. The "effect of enhancing fertilization function of a mammal sperm" also includes an effect of enhancing fertilization function in assisted reproduction technologies exploiting the freeze-thawed sperms of such cancer survivors.

Examples of the mammal can include humans and non-human mammals including rodents such as mice, rats, hamsters and guinea pigs, lagomorphs such as rabbits, hoofed animals such as pigs, cattle, goats, horses and sheep, carnivore animals such as dogs and cats, and non-human primates such as monkeys, rhesus macaques, cynomolgus monkeys, marmosets, orangutans and chimpanzees. Among them, for example, a mouse, a pig, or a human is preferred.

The enhancer of the present invention is broadly classified into liquid type and non-liquid type. Examples of the liquid type enhancer can include liquids containing the compound group of the present invention thawed in a solvent (e.g., a physiological aqueous solution such as a sperm preparation medium, and a culture medium). The non-liquid type enhancer is configured as an agent containing the compound group of the present invention in the form of a powder or the like to be generally added to the solvent. Such non-liquid type enhancer can be added to a physiological aqueous solution and a culture medium to prepare the compound group-containing physiological aqueous solution of the present invention and the compound group-containing culture medium of the present invention, respectively, which are liquid type enhancers.

The physiological aqueous solution is not particularly limited as long as the physiological aqueous solution is an isotonic aqueous solution having a salt or sugar concentration, etc. adjusted with sodium, potassium or the like so as to have almost the same osmotic pressure as that of body fluid or cell sap. Examples thereof can include sperm preparation media for livestock, etc. (liquids for density gradient centrifugation for sperm washing and enrichment), for example, Percoll; sperm preparation media for assisted reproduction technologies of humans, for example, Sepa-Sperm (Kitazato Corp., Shizuoka, Japan), PureCeption (SAGE[R], CooperSurgical, Inc., CT, USA), Isolate (FUJI-FILM Irvine Scientific, Inc., CA, USA), and SupraSperm (ORIGIO[R], CooperSurgical, Inc., CT, USA); saline; phosphate buffered saline [PBS]; Tris buffered saline [TBS]; HEPES buffered saline; Ringer's solutions (lactate Ringer's solution, acetate Ringer's solution, bicarbonate Ringer's solution, etc.); 5% aqueous glucose solution; and culture media. In the enhancement method of the present invention, a culture medium is preferred for culturing a mammal sperm before fertilization or semination. In the enhancement method of the present invention, a sperm preparation medium is preferred, and a sperm preparation medium for assisted reproduction technologies of humans is more preferred, when a mammal sperm is not cultured before fertilization or semination. In this specification, "isotonic" means that the osmotic pressure falls within the range of 250 to 380 mOsm/L.

The culture medium can be any culture medium suitable for survival and/or maintenance of mammal sperms. Examples thereof can include TYH culture medium, HTF culture medium, KSOM culture medium, Dulbecco's PBS culture medium, M2 culture medium, PB1 culture medium, Hanks culture medium, Hepes-TALP culture medium, Hoppe & Pitts culture medium, m-KRB culture medium, HIS culture medium, BO culture medium, mTALP culture medium, mT culture medium, MCM culture medium, CCM culture medium, K-MCM culture medium, BWW culture medium, Whitten culture medium, BMOC culture medium, T6 culture medium, HT6 culture medium, Bavister-TALP culture medium, SOF culture medium, Menezo-B2 culture medium, Ham's culture medium, Medium 199 culture medium, MEM culture medium, mWM culture medium, and culture media dedicated to human embryos, for example, cleavage medium (SAGE[R] Cleavage Medium, CooperSurgical, Inc., CT, USA), sperm washing medium (FUJIFILM Irvine Scientific, Inc., CA, USA), fertilization (HTF) medium (SAGE In-Vitro Fertilization, CT, USA), Ferticult (R) Sperm Washing Flushing Medium (FertiPro N.V., Beernem, Belgium), and Insemination Medium and NI fertilization Medium (NAKA ivf medium, Nakamedical, Inc., Japan) containing 10% plasma protein fraction (plasma protein fraction [PPF], human albumin [HAS], SSS; serum substitute supplement [manufactured by FUJIFILM Irvine Scientific, Inc.], etc.).

The enhancer of the present invention may comprise a component enhancing fertilization function of a mammal sperm, other than the compound group of the present invention. Since the compound group of the present invention exerts an excellent effect of enhancing fertilization function of a mammal sperm by itself, it is preferred that the enhancer of the present invention should not comprise a component enhancing fertilization function of a mammal sperm (e.g., proteins, DNA, RNA, and plant-derived extracts), other than the compound group of the present invention.

In the step (a), the mammal sperm may be a mammal sperm-containing liquid (e.g., semen and a sperm suspension) or may be the mammal sperm itself which is not contained in a liquid. Such a mammal sperm can be aspirated into, for example, a capillary (capillary tube made of glass, synthetic resin or the like) or a polypropylene micropipette tip having an inside diameter which permits aspiration of the mammal sperm, and transferred (mixed or injected) into a droplet-like compound group-containing physiological aqueous solution of the present invention placed on or contacted with a container for microscopic observation. When the mammal sperm after the step (a) is cultured before fertilization or semination and when the physiological aqueous solution is a culture medium, the droplet-like compound group-containing physiological aqueous solution of the present invention is usually cultured as it is. Alternatively, when the mammal sperm after the step (a) is cultured or washed and enriched before fertilization or semination and when the physiological aqueous solution is not a culture medium, it is preferred that the mammal sperm should be aspirated into a capillary or a polypropylene micropipette tip by the operation mentioned above, then transferred (mixed or injected) into the droplet-like compound group-containing culture medium of the present invention placed on or contacted with a container for microscopic observation, or the compound group-containing culture medium of the present invention left standing on a glass or high density polypropylene (PP) conical tube for centrifugation, etc., and cultured or washed and enriched in this droplet-like compound group-containing culture medium of the present invention. The compound group-containing physiological aqueous solution of the present invention (compound group-containing culture medium of the present invention) containing the mammal sperm obtained by the enhancement method of the present invention can be used directly as a mammal sperm suspension in the subsequent culture (semination by in vitro fertilization) in step (b-1) or an intracytoplasmic sperm injection step. In the intracytoplasmic sperm injection step, when the collected mammal ovum is an ovum around which granulosa cells (cumulus cells) are attached (cumulus oocyte complex [COC]), a mammal ovum treated with hyaluronidase for removal of the granulosa cells is preferred. In the intracytoplasmic sperm injection step, the droplet-like compound group-containing physiological aqueous solution of the present invention (compound group-containing culture medium of the present invention) containing the mammal sperm after the step (a) or the pre-fertilization/pre-semination culture step is mixed with, for example, PVP (polyvinylpyrrolidone), and then aspirated into a glass pipette (injection pipette for intracytoplasmic sperm injection) by the operation mentioned above. The mammal sperm is microinjected to a mammal ovum in a droplet-like mammal ovum-containing physiological aqueous solution placed on or contacted with a container for microscopic operation.

In the step (b-1), the mammal sperm obtained by the enhancement method of the present invention may be a mammal sperm-containing liquid (e.g., a sperm suspension) or may be the mammal sperm itself which is not contained in a liquid. Such a mammal sperm can be aspirated into, for example, a capillary or a polypropylene micropipette tip by the operation mentioned above, then transferred (mixed or injected) at an appropriate concentration (human sperm concentration: preferably 100000 to 400000/mL) into a droplet-like mammal ovum-containing culture medium placed on or contacted with a container for microscopic observation, or a mammal ovum-containing culture medium in a culture dish for semination, and cultured (seminated) in this compound group-containing culture medium of the present invention. In the step (b-2), for example, a collected mammal sperm and mammal ovum were aspirated separately or together into a capillary or a polypropylene micropipette tip by the operation mentioned above, then transferred (mixed or injected) at an appropriate concentration (human sperm concentration: preferably 100000 to 400000/mL) into a droplet-like compound group-containing culture medium of the present invention placed on or contacted with a container for microscopic observation, or a mammal ovum-containing culture medium in a culture dish for semination, and cultured (seminated) in this compound group-containing culture medium of the present invention.

The droplet-like compound group-containing physiological aqueous solution of the present invention (compound group-containing culture medium of the present invention), or the droplet-like mammal ovum-containing physiological aqueous solution (culture medium) or the mammal ovum-containing physiological aqueous solution (culture medium) in a culture dish for semination is preferably covered with an oil in order to prevent evaporation of the liquid during culture.

The culture temperature of the mammal sperm and the mammal ovum is usually in the range of about 30 to 40° C., preferably about 37° C. The $CO_2$ concentration at the time of culture is usually in the range of about 1 to 10%, preferably about 5%. The humidity at the time of culture is usually in the range of about 70 to 100%, preferably in the range of about 95 to 100%. The $O_2$ concentration at the time of culture may be a normal oxygen concentration (e.g., 18 to 22% $O_2$) or may be a low oxygen concentration (e.g., 0 to 10% $O_2$).

The oil can be a hydrophobic substance that is isolated from an animal, a plant, a mineral or the like, is liquid at ordinary temperature, and causes phase separation from water. Specific examples thereof can include mineral oil (mineral-derived oil), silicone oil, salad oil, and coconut oil. Among them, for example, mineral oil is preferred.

The container for microscopic observation is not particularly limited as long as the container is partially or wholly superior in transparency and is made of a raw material which permits observation under a phase contrast microscope. The container for microscopic operation is not particularly limited as long as the container is partially or wholly superior in transparency and is made of a raw material which permits intracytoplasmic sperm injection. Specific examples of these containers can include containers made of resins such as polymethyl methacrylate (PMMA), polycarbonate, polypropylene, polyethylene, polymethylpentene, polystyrene, polytetrafluoroethylene, ABS resin, polydimethylsiloxane, polyethylene terephthalate, cycloolefin polymer, fluorine resin, and silicone, and copolymers and complexes containing these polymer compounds as raw materials, and containers made of glass such as quartz glass, Pyrex® glass, soda glass, borate glass, silicate grass, and borosilicate glass, and complexes thereof as raw materials.

Examples of the shape of the container for microscopic observation or the container for microscopic operation can include film (sheet) shapes, Petri dish (dish) shapes, well plate shapes, and tray shapes. Among them, for example, a Petri dish (dish) shape is preferred.

The volume of the droplet-like compound group-containing physiological aqueous solution of the present invention (compound group-containing culture medium of the present invention) or the volume of the droplet-like mammal ovum-containing physiological aqueous solution (culture medium) is usually 1.0 μL or larger, preferably 10 μL or larger, more preferably 30 μL or larger, and is usually 500 μL or smaller, preferably 400 μL or smaller, more preferably 350 μL or smaller, still more preferably 300 μL or smaller, from the viewpoint of facilitating confirming the presence of a very small number of sperms under a microscope. Thus, the volume of the droplet-like compound group-containing physiological aqueous solution of the present invention (compound group-containing culture medium of the present invention) or the volume of the droplet-like mammal ovum-containing physiological aqueous solution (culture medium) is usually in the range of 1.0 to 500 μL, preferably in the range of 10 to 400 μL, more preferably in the range of 100 to 350 μL, still more preferably in the range of 100 to 300 μL. In the case of using a culture or semination dish having a well shape, the volume of the compound group-containing physiological aqueous solution of the present invention (compound group-containing culture medium of the present invention) or the volume of the droplet-like mammal ovum-containing physiological aqueous solution (culture medium) is preferably a volume recommended by a manufacturer of the culture or semination dish used.

In this specification, "at least one mammal sperm" means that the number of mammal sperms is one or more, and includes one mammal sperm as well as the number of mammal sperms in the range of, for example, 1 to 2, 1 to 3, 1 to 4, 1 to 5, 1 to 6, 1 to 7, 1 to 8, 1 to 9, 1 to 10, 1 to 50, or 1 to 100.

In this specification, "at least one mammal ovum" means that the number of mammal ova is one or more, and includes one mammal ova as well as the number of mammal ova in the range of, for example, 1 to 2, 1 to 3, 1 to 4, 1 to 5, or 1 to 6.

The concentration of the compound group of the present invention in the compound group-containing physiological aqueous solution of the present invention (compound group-containing culture medium of the present invention) can be any concentration which exerts an effect of enhancing fertilization function of a mammal sperm. This concentration differs depending on the type of the mammal, the concentration of the mammal sperm, the number of mammal ova, etc. and therefore, cannot be generalized. The concentration is in the range of, for example, 0.01 to 100 µM, preferably 0.05 to 50 µM, more preferably 0.1 to 10 µM.

In the enhancement method of the present invention, the culture period of the mammal sperm can be any period which exerts an effect of enhancing fertilization function of a mammal sperm. This period differs depending on the type of the mammal, the concentration of the mammal sperm, the number of mammal ova, etc. and therefore, cannot be generalized. The period is in the range of, for example, 1 minute to 12 hours, preferably 5 minutes to 6 hours, more preferably 10 minutes to 3 hours, still more preferably 30 minutes to 2 hours.

In the step (b-1) of the preparation method 1 of the present invention, the culture (semination by in vitro fertilization) period of the mammal sperm obtained by the enhancement method of the present invention in the mammal ovum-containing culture medium can be any period which is long enough to complete fertilization. This period differs depending on the type of the mammal, the concentration of the mammal sperm, the number of mammal ova, etc. and therefore, cannot be generalized. The period is in the range of, for example, 3 to 24 hours, preferably 3 to 12 hours or 12 to 24 hours. In consideration of usual fertilization which is completed 12 to 18 hours after semination (see the documents "Nagy Z P, et al., 1994 Human Reproduction 9, 1743-1748" and "Zsolt P. Nagy et al., 1998 Human Reproduction 13, 1606-1612"), 12 to 18 hours are more preferred.

In the step (b-2) of the preparation method 2 of the present invention, the culture (semination by in vitro fertilization) period of the mammal sperm and the mammal ovum in the compound group-containing culture medium of the present invention can be any period which exerts an effect of enhancing fertilization function of a mammal sperm and is long enough to complete fertilization. This period differs depending on the type of the mammal, the concentration of the mammal sperm, the number of mammal ova, etc. and therefore, cannot be generalized. The period is in the range of, for example, 3 to 24 hours, preferably 3 to 12 hours or 12 to 24 hours. In consideration of usual fertilization which is completed 12 to 18 hours after semination, 12 to 18 hours are more preferred.

A detailed description of the compounds contained in compound group of the present invention is given below.

In one aspect of the present invention, $R^1$ in the formula ($I_0$) is a benzoylmethyl group whose benzene ring is unsubstituted or a benzoylmethyl group whose benzene ring is substituted by an alkyl group having 1 to 7 carbon atoms, an alkoxyl group having 1 to 7 carbon atoms, fluorine, and/or chlorine. Such a "benzene ring having an alkyl group having 1 to 7 carbon atoms, an alkoxyl group having 1 to 7 carbon atoms, or a benzoylmethyl group substituted with fluorine and/or chlorine" means one or more hydrogen atoms that bind to a carbon atom constituting the benzene ring of the benzoylmethyl group are replaced by an alkyl group having 1 to 7 carbon atoms, an alkoxyl group having 1 to 7 carbon atoms, a fluorine atom and/or a chlorine atom. Accordingly, the substituted benzene ring means that 1 to 5 hydrogen atoms of the hydrogen atoms bonded to the carbon atoms constituting the benzene ring are substituted with an alkyl group having 1 to 7 carbon atoms, an alkoxyl group having 1 to 7 carbon atoms, a benzene ring substituted by fluorine and/or chlorine. When the substituted benzene ring has two or more substituents, the substituents is the same or different. Examples thereof can include a benzene ring substituted with an alkyl group having 1 to 7 carbon atoms with 1 to 5 carbon atoms, a benzene ring substituted with 1 to 7 alkoxyl groups having 1 to 5 carbon atoms, a benzene ring substituted with 1 to 5 fluorine atoms or a benzoylmethyl group having a benzene ring substituted with 1 to 5 chlorine atoms. Further, as other examples, a benzoylmethyl group having a benzene ring substituted with a total of 2 to 5 substituents selected from an alkyl group having 1 to 4 carbon atoms, an alkoxyl group having 1 to 4 carbon atoms, a fluorine atom and a chlorine atom can be mentioned. In this context, examples of the alkyl group having 1 to 7 carbon atoms can include a methyl group, an ethyl group, a propyl group, an isopropyl group, an n-butyl group, an isobutyl group, a sec-butyl group, a tert-butyl group, an n-pentyl group, a 1-methylbutyl group, a 2-methylbutyl group, a 3-methylbutyl group, a 1-ethylpropyl group, a 1,1-dimethylpropyl group, a 1,2-dimethylpropyl group, an n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1-ethylbutyl group, a 2-ethylbutyl group, a 1-ethyl-1-methylpropyl group, a 1-ethyl-2-methylpropyl group, a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1-ethylbutyl group, a 2-ethylbutyl group, a 1-ethyl-1-methylpropyl group, a 1-ethyl-2-methylpropyl group, an n-heptyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 3-ethylpentyl group, a 4,4-dimethylpentyl group, and a 1-propylbutyl group.

Examples of the alkoxyl group having 1 to 7 carbon atoms can include a methoxy group, an ethoxy group, a propoxy group, an isopropoxy group, an n-butoxy group, an isobutoxy group, a sec-butoxy group, a tert-butoxy group, an n-pentoxy group, a 1-methylbutoxy group, a 2-methylbutoxy group, a 3-methylbutoxy group, a 1-ethylpropoxy group, a 1,1-dimethylpropoxy group, a 1,2-dimethylpropoxy group, a 2,2-dimethylpropoxyl group, an n-hexyloxy group, a 1-methylpentyloxy group, a 2-methylpentyloxy group, a 3-methylpentyloxy group, a 4-methylpentyloxy group, a 1,1-dimethylbutoxy group, a 1,2-dimethylbutoxy group, a 1,3-dimethylbutoxy group, a 2,2-dimethylbutoxy group, a 2,3-dimethylbutoxy group, a 3,3-dimethylbutoxy group, a 1,1,2-trimethylpropoxy group, a 1-ethylbutoxy group, a 2-ethylbutoxy group, a 1-ethyl-1-methylpropoxy group, a 1-ethyl-2-methylpropoxy group, an n-heptyloxy group, a 1-methylhexyloxy group, a 2-methylhexyloxy group, a 3-methylhexyloxy group, a 4-methylhexyloxy group, a 5-methylhexyloxy group, a 1-ethylpentyloxy group, a 2-ethylpentyloxy group, a 3-ethylpentyloxy group, a 4,4-dimethylpentyloxy group, and a 1-propylbutoxy group.

In an alternative aspect of the present invention, $R^1$ in the formula ($I_0$) is an unsubstituted or fluorine-substituted linear or branched alkyl group having 4 to 6 carbon atoms. Examples of the unsubstituted or fluorine-substituted linear or branched alkyl group having 4 to 6 carbon atoms can include an n-butyl group, an isobutyl group, a sec-butyl group, a tert-butyl group, an n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, an n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1-ethylbutyl group, a 2-ethylbutyl group, a 1-ethyl-1-methylpropyl group, a 1-ethyl-2-methylpropyl group, and fluorinated forms thereof. The unsubstituted or fluorine-substituted linear or branched alkyl group having 4 to 6 carbon atoms is preferably a 1-ethylbutyl group, a 2-ethylbutyl group, a 1-methylpentyl group, a 2-methylpentyl group, a 3-methylpentyl group, a 4-methylpentyl group, a 5-methylpentyl group, a 3,3,4,4,4-pentafluorobutyl group, a 4,4,5,5,5-pentafluoropentyl group, or a 5,5,6,6,6-pentafluorohexyl group, more preferably a 2-ethylbutyl group, a 2-methylpentyl group, a 3-methylpentyl group, or a 4,4,5,5,5-pentafluoropentyl group, most preferably a 4,4,5,5,5-pentafluoropentyl group.

In an alternative aspect of the present invention, $R^1$ in the formula ($I_0$) is phenyl group- or cyclopentyl group-substituted methylene or ethylene. The phenyl group is optionally further substituted by one or more phenyl groups. The phenyl group- or cyclopentyl group-substituted methylene or ethylene is a benzyl group, a 2-phenethyl group, a cyclopentylmethyl group, or a 2-cyclopentylethyl group. Examples of the benzyl group or the 2-phenethyl group substituted by one or more phenyl groups can include a 3-phenylbenzyl group, a 4-phenylbenzyl group, a 3,5-diphenylbenzyl group, a 2-(1,1'-biphenyl-3-yl)-ethyl group, a 2-(1,1'-biphenyl-4-yl)-ethyl group, and a 2-(3,5-diphenylphenyl)-ethyl group. Preferred examples of $R^1$ in the formula (I) can include a 2-phenethyl group, a cyclopentylmethyl group, a 2-cyclopentylethyl group, and a 2-(1,1'-biphenyl-3-yl)-ethyl group.

$Z^1$, $Z^2$, $Z^3$ and $Z^4$ in the formula ($I_0$) is the same or different and each is a hydrogen atom, a halogen atom, a C1 to C6 alkyl group, a C2 to C6 alkenyl group, a C2 to C6 alkynyl group, an organic oxy group represented by $OR^8$. $R^8$ is a C1 to C7 alkyl group, a C2 to C6 alkenyl group or a C2 to C6 alkynyl group. $Z^3$ can include a hydrogen atom or a C1 to C6 alkyl group. Examples of the halogen atom can include a fluorine atom, a chlorine atom, a bromine atom, and an iodine atom. Examples of a C1 to C6 alkyl group can include a methyl group, an ethyl group, a propyl group, an isopropyl group, an n-butyl group, an isobutyl group, a sec-butyl group, a tert-butyl group, an n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, an n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1-ethylbutyl group, a 2-ethylbutyl group, a 1-ethyl-1-methylpropyl group, and a 1-ethyl-2-methylpropyl group. Examples of a C2 to C6 alkenyl group can include an ethenyl group (vinyl group), a 1-propenyl group, a 2-propenyl group (allyl group), a 1-butenyl group, a 2-butenyl group, a 3-butenyl group, an isobutyl group, 1-pentenyl group, 2-pentenyl group, 3-pentenyl group, 4-pentenyl group, 1-hexenyl group, 2-hexenyl group, 3-hexenyl group, 4-hexenyl group, and 5-hexenyl group. Examples of C2 to C6 alkynyl groups can include ethynyl group, 1-propynyl group, 2-propynyl group (propargyl group), 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynl group, and 1,1-dimethyl-2-butynyl group. Examples of a C1 to C7 alkoxyl group (when $R^8$ is a C1 to C7 alkyl group at an organic oxy group represented by $OR^8$), can include a methoxy group, an ethoxy group, a propoxy group, an isopropoxy group, an n-butoxy group, an isobutoxy group, a sec-butoxy group, a tert-butoxy group, an n-pentoxy group, a 1-methylbutoxy group, a 2-methylbutoxy group, a 3-methylbutoxy group, a 1-ethylpropoxy group, a 1,1-dimethylpropoxy group, a 1,2-dimethylpropoxy group, a 2,2-dimethylpropoxyl group, an n-hexyloxy group, a 1-methylpentyloxy group, a 2-methylpentyloxy group, a 3-methylpentyloxy group, a 4-methylpentyloxy group, a 1,1-dimethylbutoxy group, a 1,2-dimethylbutoxy group, a 1,3-dimethylbutoxy group, a 2,2-dimethylbutoxy group, a 2,3-dimethylbutoxy group, a 3,3-dimethylbutoxy group, a 1,1,2-trimethylpropoxy group, a 1-ethylbutoxy group, a 2-ethylbutoxy group, a 1-ethyl-1-methylpropoxy group, a 1-ethyl-2-methylpropoxy group, an n-heptyloxy group, a 1-methylhexyloxy group, a 2-methylhexyloxy group, a 3-methylhexyloxy group, a 4-methylhexyloxy group, a 5-methylhexyloxy group, a 1-ethylpentyloxy group, a 2-ethylpentyloxy group, a 3-ethylpentyloxy group, a 4,4-dimethylpentyloxy group, and a 1-propylbutoxy group. $Z^1$, $Z^2$, $Z^3$ and $Z^4$ are the same or different, preferably hydrogen, an ethoxy group, fluorine, or chlorine.

$R^4$ and $R^5$ in the formula ($I_0$) are the same or different and each is a substituted or unsubstituted alkyl group having 1 to 4 carbon atoms. Examples of the substituted or unsubstituted alkyl group having 1 to 4 carbon atoms can include a methyl group, an ethyl group, a propyl group, an isopropyl group, an n-butyl group, an isobutyl group, a sec-butyl group, a tert-butyl group, pyrrolidine formed by $R^4$ and $R^5$ together with nitrogen, and forms thereof substituted by a methoxy group, a phenyl group, fluorine, and chlorine. The substituted or unsubstituted alkyl group having 1 to 4 carbon atoms is preferably a methyl group, a monochloromethyl group, an ethyl group, a 2-methoxyethyl group, a 2,2,2-trichloroethyl group, a 1-phenylethyl group, a 2-phenylethyl group, a methoxyethyl group, an isopropyl group, a hexafluoroisopropyl group, or pyrrolidine, more preferably a methyl group or an ethyl group.

An embodiment of the above formula ($I_0$), includes a compound of the following formula (I) and preferably a compound of the formula (1).

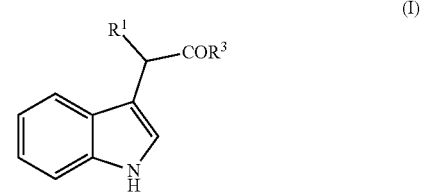

(I)

[wherein $R^1$ and $R^3$ have the same meanings as defined in the above [1].]

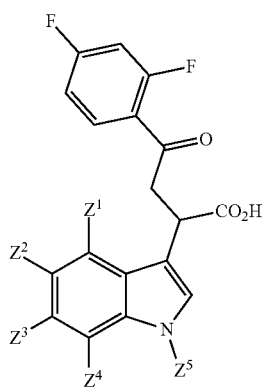

(1)

[wherein $Z^1$, $Z^2$, $Z^3$, $Z^4$ and $Z^5$ have the same meanings as defined in the above [1].]

In the compound of the above formula (1), $Z^1$, $Z^2$, $Z^3$ and $Z^4$ which are the same or different, are a hydrogen atom, a halogen atom, a C1 to C6 alkyl group, a C2 to C6 alkenyl group, a C2 to C6 alkynyl group, or an organic oxy group represented by $OR^8$, $R^8$ is a C1 to C7 alkyl group, a C2 to C6 alkenyl group, or a C2 to C6 alkynyl group, $Z^5$ is a hydrogen atom or a C1 to C6 alkyl group.

Examples of the halogen atom in the formula (1) can include a fluorine atom, a chlorine atom, a bromine atom, and an iodine atom.

The C1 to C6 alkyl group in the formula (1) means a linear or branched alkyl group having 1 to 6 carbon atoms which may have a substituent, and specific examples thereof can include methyl, ethyl, n-propyl, isopropyl, n-butyl, isobutyl, sec-butyl, tert-butyl, n-pentyl, isopentyl, neopentyl and n-hexyl groups.

Examples of the substituent of the above-mentioned "optionally have a substituent" can include a halogen atom, a hydroxyl group, a carboxyl group, an alkyl group having 1 to 6 carbon atoms, an alkenyl group having 2 to 6 carbon atoms, an alkynyl group having 2 to 6 carbon atoms and a C6 to C10 aryl group. The alkyl group having 1 to 6 carbon atoms, the alkenyl group having 2 to 6 carbon atoms and the alkynyl group having 2 to 6 carbon atoms are preferably the same as an alkyl group having 1 to 6 carbon atoms, an alkenyl having 2 to 6 carbon atoms group, and alkynyl group having 2 to 6 carbon atoms in the formula (1). Examples of the C6 to C10 aryl groups can include a phenyl group and a naphthyl group.

The C2 to C6 alkenyl group in the formula (1) means a linear or branched alkenyl group having 2 to 6 carbon atoms which optionally have a substituent, and specific examples thereof can include a vinyl group, 1-propenyl group, 2-propenyl group, 1-butenyl group, 2-butenyl group, 3-butenyl group, 1,3-butenyl group, 1-pentenyl group, and 1-hexenyl group.

The C2 to C6 alkynyl group in the formula (1) means a linear or branched alkynyl group having 2 to 6 carbon atoms which optionally have a substituent, and specific examples thereof can include an ethynyl group, 1-propynyl group, 1-butynyl group, 1-pentynyl group, and 1-hexynyl group.

$Z^1$, $Z^2$, $Z^3$ and $Z^4$ are preferably a hydrogen atom, a halogen atom, a C1 to C6 alkyl group, or an organic oxy group represented by $OR^8$, preferably a hydrogen atom, a fluorine atom, a chlorine atom, a methyl group, an ethyl group, more preferably a C1 to C3 alkyl group such as an n-propyl group or an isopropyl group, and an organic oxy group represented by $OR^8$.

$Z^5$ is preferably a hydrogen atom or a C1 to C3 alkyl group, more preferably a hydrogen atom or a methyl group.

$R^8$ is preferably a C1 to C6 alkyl group, more preferably a C1 to C3 alkyl group such as a methyl group, an ethyl group, an n-propyl group or an isopropyl group, or a benzyl group.

Among the compounds of the above formula (1), the compounds of the following formula (2), formula (3), formula (4), formula (5), and formula (6) or the salts thereof are preferable.

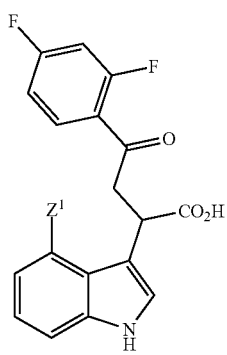

(2)

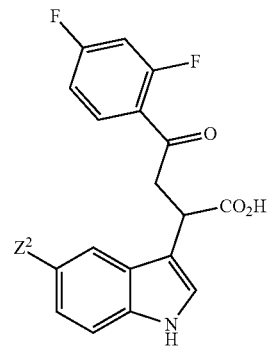

(3)

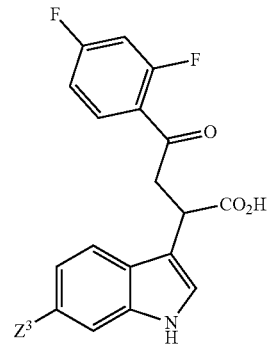

(4)

-continued
(5)
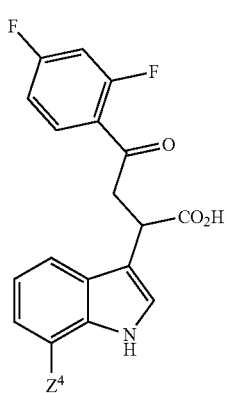
(6)
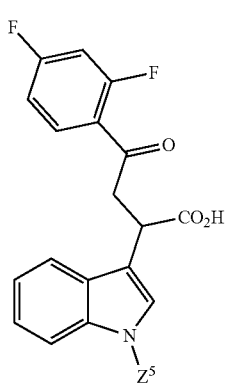
$Z^1$, $Z^2$, $Z^3$, $Z^4$, $Z^5$ in the above formulas (2), (3), (4), (5) and (6) have the same definitions as $Z^1$, $Z^2$, $Z^3$, $Z^4$, $Z^5$ in the formula (1).
Specifically, examples of the compound of the formula (1) can include the following compounds.
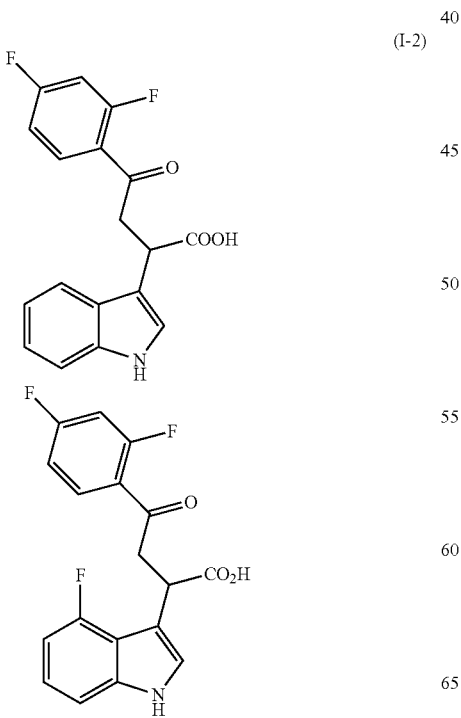
(I-2)
-continued
(2-1)
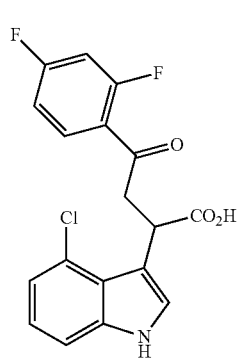
(3-1)
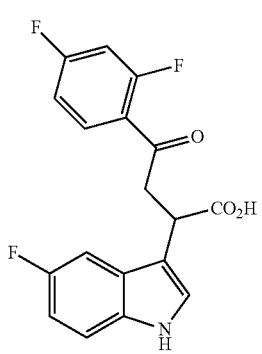
(3-2)
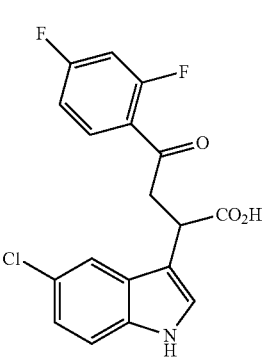
(4-1)
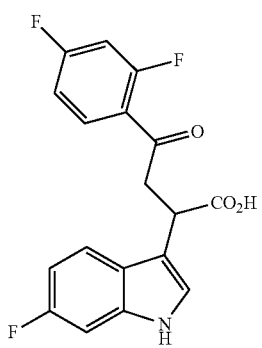

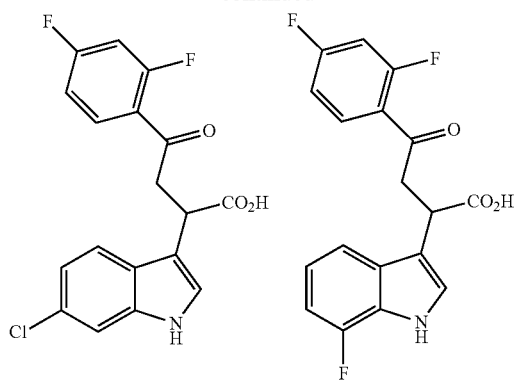
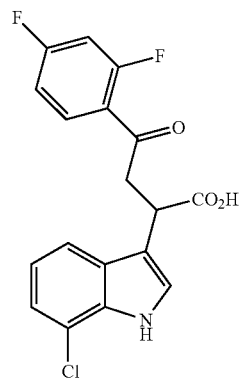
(5-1)
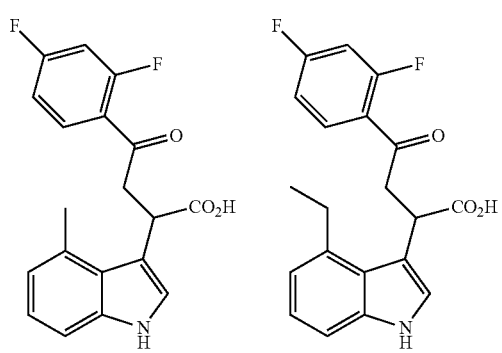
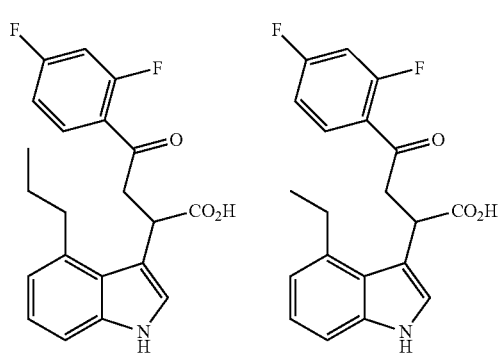
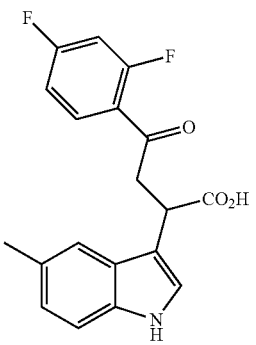
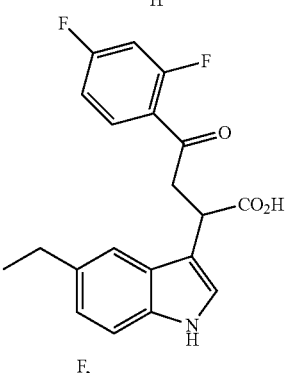
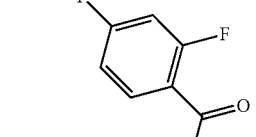
(3-3)
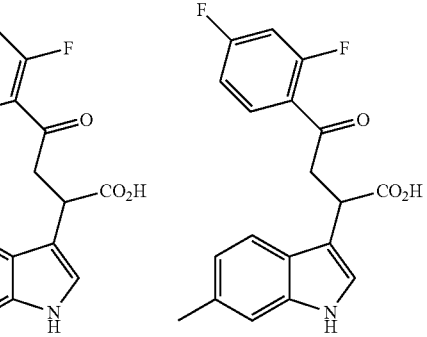
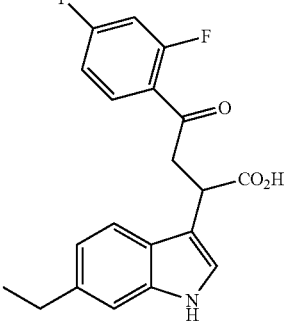

-continued
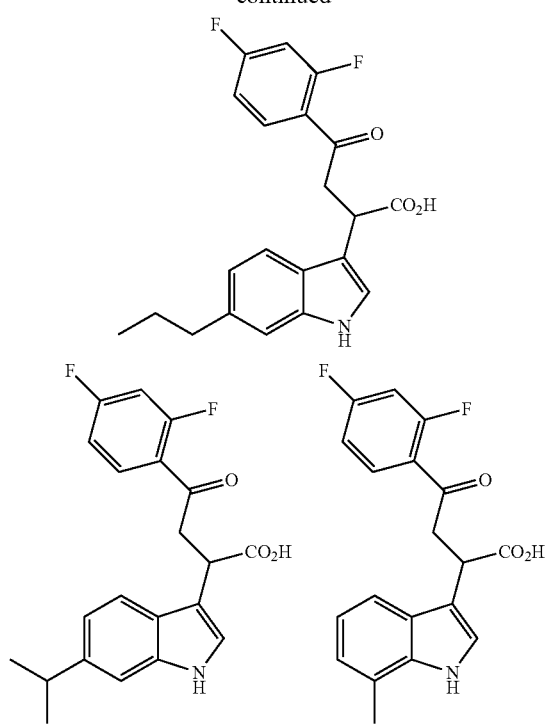
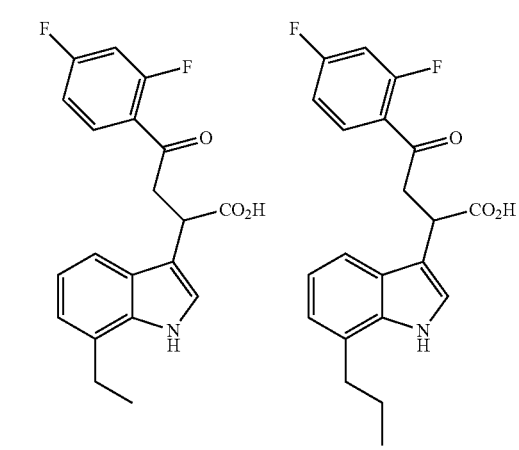
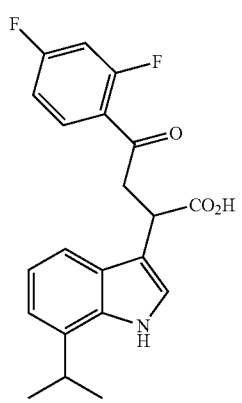
-continued
(6-1)
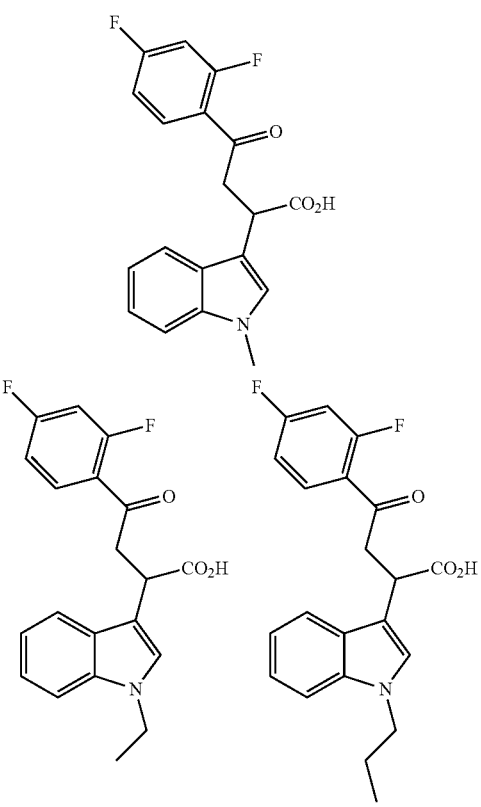
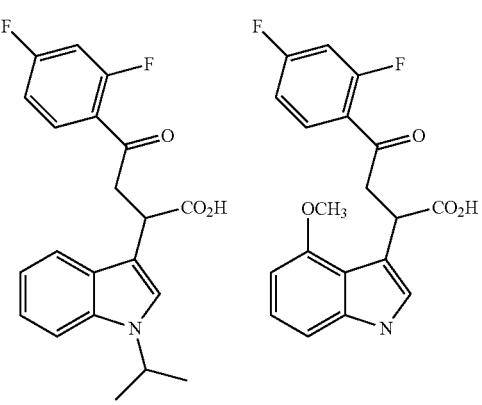 [SMILES: CC(C)n1cc(C(CC(=O)c2ccc(F)cc2F)C(=O)O)c2ccccc21 ; COc1cccc2[nH]cc(C(CC(=O)c3ccc(F)cc3F)C(=O)O)c12]
(3-4)
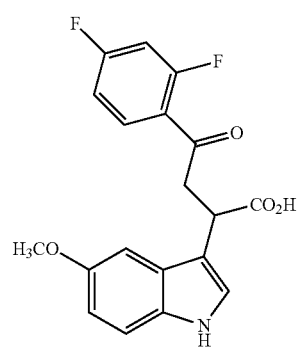

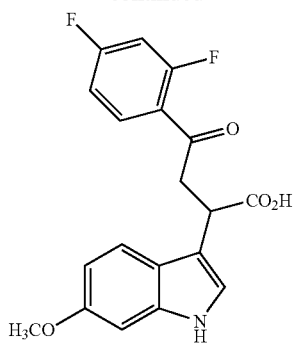
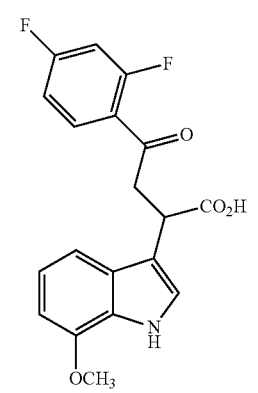
(5-2)
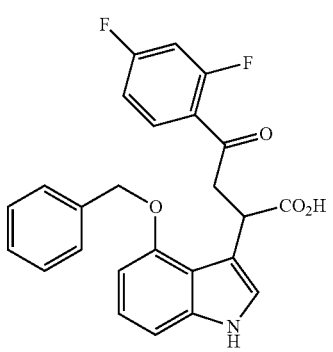
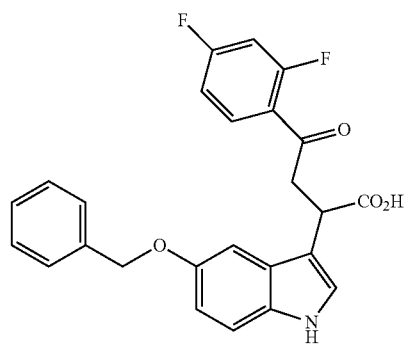
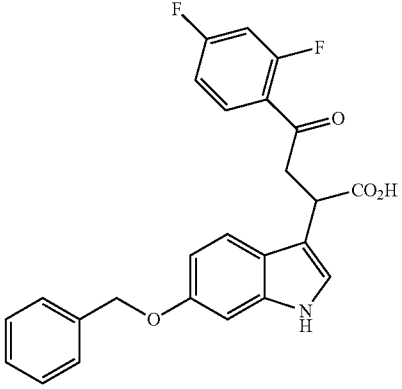
(4-2)
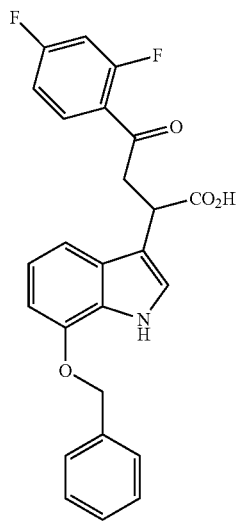
Among the above compounds, the following compounds are preferable.
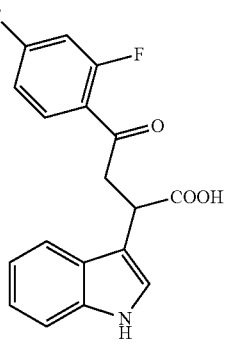
(I-2)

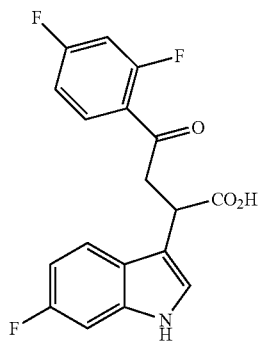
(4-1)
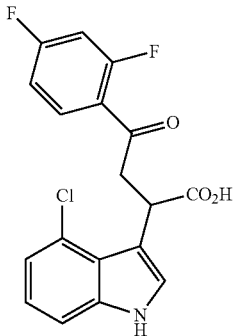
(2-1)
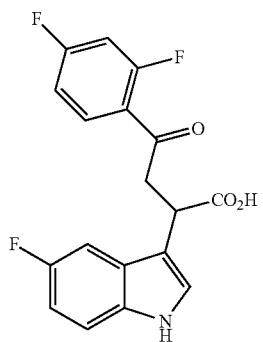
(3-1)
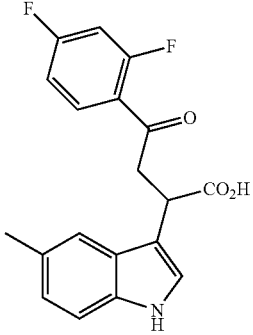
(3-3)
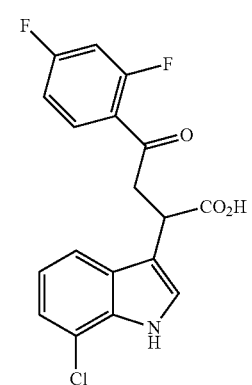
(5-1)
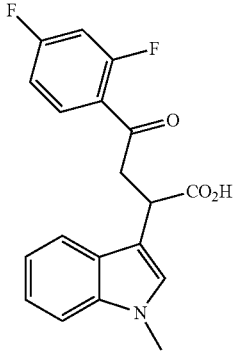
(6-1)
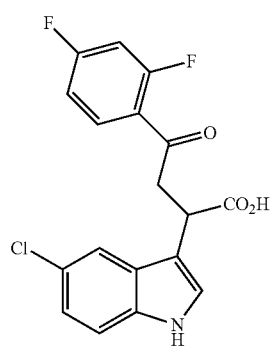
(3--2)
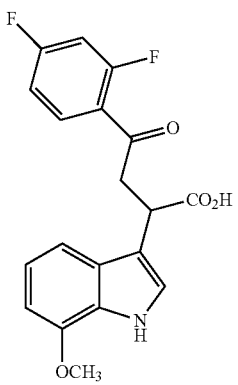
(5-2)

(3-4)

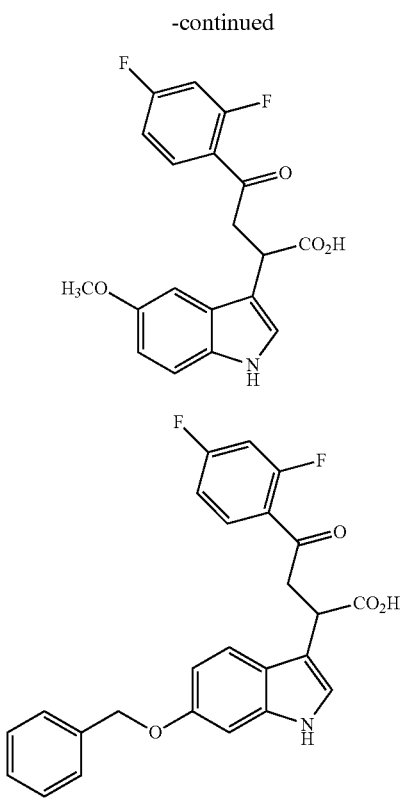

(4-2)

The compound of the formula ($I_0$) wherein $R^1$ is a 2,4-difluorobenzoylmethyl group, $Z^1$, $Z^2$, $Z^3$, $Z^4$, and $Z^5$ are hydrogen and $R^3$ is OH, is compound #5 mentioned later in Examples. The compound of the formula ($I_0$) wherein $R^1$ is a 4-fluorobenzoylmethyl group, $Z^1$, $Z^2$, $Z^3$, $Z^4$, and $Z^5$ are hydrogen, and $R^3$ is OH, is compound #4 mentioned later in Examples. The compound of the formula ($I_0$) wherein $R^1$ is a 4,4,5,5,5-pentafluoropentyl group, $Z^1$, $Z^2$, $Z^3$, $Z^4$, and $Z^5$ are hydrogen, and $R^3$ is OH, is compound #21 mentioned later in Examples. The compound of the formula ($I_0$) wherein $R^1$ is a 2-cyclopentylethyl group, $Z^1$, $Z^2$, $Z^3$, $Z^4$, and $Z^5$ are hydrogen, and $R^3$ is OH, is compound #24 mentioned later in Examples. In addition to these compounds, specific examples of the compound of the formula ($I_0$) can include compounds #2, 4, 5, and 20 mentioned later in Examples, compounds #17 to 19 mentioned later in Examples, compounds #22 and 23 mentioned later in Examples, and compound #25 mentioned later in Examples.

X in the formula (II) is a linear alkylene group having 4 to 6 carbon atoms, i.e., butylene —$(CH_2)_4$—, pentylene —$(CH_2)_5$—, or hexylene —$(CH_2)_6$—, or an ether group having 4 carbon atoms. Examples of the ether group having 4 carbon atoms can include a methylene-O-propylene group, an ethylene-O-ethylene group, and a propylene-O-methylene group. X is preferably butylene, hexylene, or an ethylene-O-ethylene group.

$R^4$ and $R^5$ in the formula (II) are the same or different and each is a substituted or unsubstituted alkyl group having 1 to 4 carbon atoms. Examples of the substituted or unsubstituted alkyl group having 1 to 4 carbon atoms can include a methyl group, an ethyl group, a propyl group, an isopropyl group, an n-butyl group, an isobutyl group, a sec-butyl group, a tert-butyl group, pyrrolidine formed by $R^4$ and $R^5$ together with nitrogen, and forms thereof substituted by a methoxy group, a phenyl group, fluorine, and chlorine. The substituted or unsubstituted alkyl group having 1 to 4 carbon atoms is preferably a methyl group, a monochloromethyl group, an ethyl group, a 2,2,2-trichloromethyl group, a 1-phenylethyl group, a 2-phenylethyl group, a methoxyethyl group, an isopropyl group, a hexafluoroisopropyl group, or pyrrolidine, more preferably a methyl group or an ethyl group.

The compound of the formula (II) wherein X is butylene, $R^6$ is hydrogen, and $R^3$ is OH, is compound #15 mentioned later in Examples. In addition to the compound #15, specific examples of the compound of the formula (I) can include compound #13 mentioned later in Examples and compound #14 mentioned later in Examples.

$R^7$ in the formula (III) is an alkyl group having 1 to 5 carbon atoms or a benzyl group. Examples of the linear or branched alkyl group having 1 to 5 carbon atoms can include a methyl group, an ethyl group, a propyl group, an isopropyl group, an n-butyl group, an isobutyl group, a sec-butyl group, a tert-butyl group, an n-pentyl group, a 1-methylbutyl group, a 2-methylbutyl group, a 3-methylbutyl group, a 1-ethylpropyl group, a 1,1-dimethylpropyl group, a 1,2-dimethylpropyl group, and a 2,2-dimethylpropyl group. The benzene ring of the benzyl group is optionally substituted by one or more alkyl groups having 1 to 3 carbon atoms or alkoxyl groups having 1 to 3 carbon atoms. Examples of the alkyl group having 1 to 3 carbon atoms can include a methyl group, an ethyl group, an n-propyl group, and an isopropyl group. Examples of the alkoxy group having 1 to 3 carbon atoms can include a methoxy group, an ethoxy group, an n-propoxy group, and an isopropoxy group. $R^7$ in the formula (III) is preferably a methyl group, an ethyl group, a propyl group, an n-butyl group, an n-pentyl group, or a 3,5-dimethoxybenzyl group, more preferably a 3,5-dimethoxybenzyl group.

$R^4$ and $R^5$ in the formula (III) are the same or different and each is a substituted or unsubstituted alkyl group having 1 to 4 carbon atoms. Examples of the substituted or unsubstituted alkyl group having 1 to 4 carbon atoms can include a methyl group, an ethyl group, a propyl group, an isopropyl group, an n-butyl group, an isobutyl group, a sec-butyl group, a tert-butyl group, pyrrolidine formed by $R^4$ and $R^5$ together with nitrogen, and forms thereof substituted by a methoxy group, a phenyl group, fluorine, and chlorine. The substituted or unsubstituted alkyl group having 1 to 4 carbon atoms is preferably a methyl group, a monochloromethyl group, an ethyl group, a 2,2,2-trichloromethyl group, a 1-phenylethyl group, a 2-phenylethyl group, a methoxyethyl group, an isopropyl group, a hexafluoroisopropyl group, or pyrrolidine, more preferably a methyl group or an ethyl group.

The compound of the formula (III) wherein A is indole, $R^7$ is a 3,5-dimethoxybenzyl group, and $R^3$ is OH, is compound #35 mentioned later in Examples. In addition to the compound #35, specific examples of the compound of the formula ($I_0$) can include compounds #36 to 38 mentioned later in Examples and compounds #33 and 34 mentioned later in Examples.

When a compound selected from compound group of the present invention has an asymmetric carbon atom and an axial chirality-related asymmetric point, this compound includes all possible optical isomers. These optical isomers can be used at an arbitrary ratio. For example, a certain optically active compound can be used as an enantiomer, a racemate, or an enantiomer mixture at an arbitrary ratio. A compound containing a plurality of asymmetric points can be used as a diastereomer mixture at an arbitrary ratio.

The physiologically acceptable salts of the compound group of the present invention include, for example, metal salts formed from aluminum, calcium, lithium, magnesium, potassium, sodium, and zinc, and organic salts formed from N,N'-dibenzylethylenediamine, chloroprocaine, choline, diethanolamine, ethylenediamine, N-methylglucamine, lysine, procaine, and the like.

Exemplary methods for synthesizing each compound selected from compound group of the present invention will be given below. However, the synthesis methods of the present invention are not limited to these methods, and generally known synthesis methods can be used. Compounds shown below can be obtained from Sigma-Aldrich Corp., Tokyo Chemical Industry Co., Ltd., Wako Pure Chemical Industries, Ltd., Kanto Chemical Co., Inc., etc. As for reaction solvents and reaction temperatures, a reaction is carried out using a solvent and a temperature usually used for the reaction, unless otherwise specified. Each reaction is carried out in an argon or nitrogen atmosphere. Each protective group can be used with reference to Green & Wuts, "PROTECTIVE GROUPS in ORGANIC SYNTHESIS" 3rd ed. John Wiley & Sons, Inc.

The compound of the formula ($I_O$) can be synthesized with substituted or unsubstituted benzene and substituted or unsubstituted indole as starting materials. First, substituted or unsubstituted benzene and maleic anhydride are used in Friedel-Crafts reaction to synthesize 4-aryl-4-oxo-2-butenoic acid. This Friedel-Crafts reaction is carried out by the action of a catalyst such as Lewis acid, phosphoric acid, or polyphosphoric acid. Aluminum chloride is preferably used as the catalyst. The reaction solvent is preferably a chlorine solvent. Alternatively, the starting material substituted or unsubstituted benzene can also be used as a solvent. The 4-aryl-4-oxo-2-butenoic acid thus obtained and substituted or unsubstituted indole are subjected to Michael reaction to obtain a compound in which the α-position of indoleacetic acid is substituted by a substituted or unsubstituted benzoyloxy group. In this way, the basic skeleton of the compound of the formula ($I_O$) can be constructed. In this Michael reaction, the carboxyl group of the 4-aryl-4-oxo-2-butenoic acid can or cannot be protected and, usually, does not have to be protected. When this carboxyl group is protected, examples of the protective group used can include a methyl ester, a tert-butyl ester, a 2,2,2-trichloroethyl ester, and a tert-butyldimethylsilyl ester. On the other hand, the nitrogen atom of the indole can or cannot be protected. When this nitrogen atom is protected, a benzyl protective group is preferred. An amide protective group is not preferred because of reducing reactivity. Also, the Michael reaction can proceed by the heating of the reaction system and can be carried out using a catalyst such as a Lewis acid. After the obtainment of the skeleton of the compound of the formula ($I_O$), the protective group can be removed, if necessary, to synthesize the compound of the formula ($I_O$). Then, the carboxylic acid moiety can also be appropriately esterified, amidated, or converted to a physiologically acceptable salt according to the purpose. Specifically, compound #5 mentioned later in Examples can be synthesized from 1,3-difluorobenzene, maleic anhydride, and indole as shown in the following scheme:

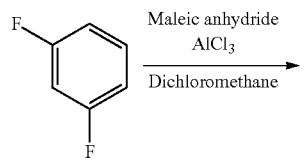
Maleic anhydride
AlCl₃
Dichloromethane

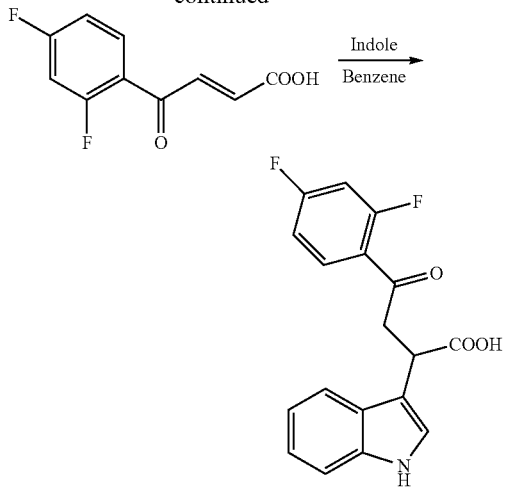

In an alternative aspect, examples of the method for synthesizing the compound of the formula ($I_O$) can include a synthesis method using an alcohol and a protected form of indoleacetic acid as starting materials. The hydroxy group of the alcohol can be converted to iodine or bromine either directly or through two-step reaction. Examples of the method involving direct conversion can include, but are not limited to, a method of substituting the alcohol by iodine (I·) by the action of triphenylphosphine, imidazole, and iodine ($I_2$), and a method of substituting the alcohol by bromine by the action of triphenylphosphine and carbon tetrabromide. Examples of the synthesis method through a plurality of steps can include a method of derivatizing the alcohol into a sulfonic acid ester such as methanesulfonate, trifluoromethanesulfonate, or toluenesulfonate, followed by reaction with an iodide salt of an alkali metal or a bromide salt of an alkali metal. The halogen form thus obtained can be nucleophilically reacted with enolate at the α-position formed from the protected form of indoleacetic acid to obtain the basic skeleton of the compound of the formula ($I_O$). Examples of the protective group for the indoleacetic acid include a method of derivatizing the indoleacetic acid into a methyl ester, a tert-butyl ester, a 2,2,2-trichloroethyl ester, or a tert-butyldimethylsilyl ester for the protection of the carboxyl group. On the other hand, the amine site of the indoleacetic acid is preferably protected as amide carbonate. Examples of the protective group can include methoxycarbonyl, ethoxycarbonyl, tert-butoxycarbonyl, and benzyloxycarbonyl. The protected form of the indoleacetic acid thus obtained is derivatized into enolate by the action of a base. The formed enolate and the halogen form can be subjected to nucleophilic reaction to obtain the basic skeleton of the compound of the formula ($I_O$). Examples of the base that can be used in this nucleophilic reaction can include: a carbonate of an alkali metal such as lithium carbonate, sodium carbonate, potassium carbonate, and cesium carbonate; an alkyllithium such as methyllithium, n-butyllithium, sec-butyllithium, and tert-butyllithium; and an alkali metal amide such as lithium diisopropylamide, lithium hexamethyldisilazane, sodium hexamethyldisilazane, and potassium hexamethyldisilazane. The solvent that can be used differs depending on the base used and is preferably an aprotic polar solvent such as N,N-dimethylformamide (DMF) or tetrahydrofuran (THF). The addition of hexamethylphosphoric triamide or the like is effective for promoting the reaction. The protective group can be removed from the protected form thus obtained to obtain the compound of interest. Then, the carboxylic acid moiety can be appropriately esterified, amidated, or converted to a physiologically acceptable salt thereof. Specifically, compound #21 mentioned later in Synthesis Examples can be synthesized with 4,4,5,5,5-pentafluoropentanol and 1-methoxycarbonyl-3-indoleacetic acid methyl ester as starting materials as shown in the following scheme:

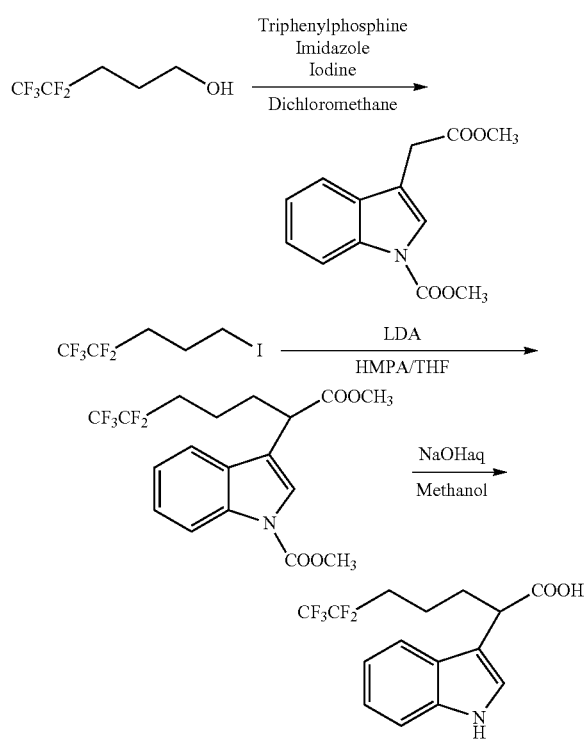

The compound of the formula (1) in the present invention can be obtained by an organic synthesis technique using a known organic chemical reaction. For example, by subjecting (E)-4-(2,4-difluorophenyl)-4-oxo-2-butenoic acid and an indole derivative of formula (7) to Michael reaction as shown below, the compound of the formula (1) can be obtained.

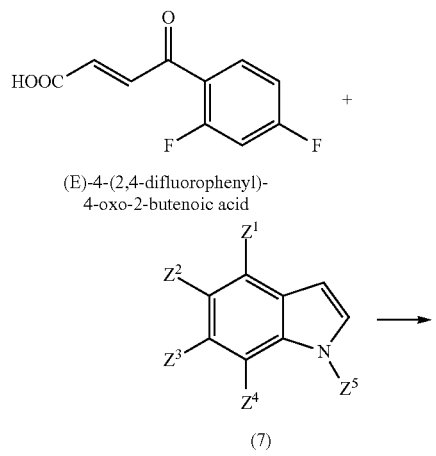

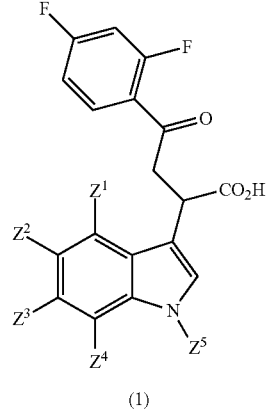

($Z^1$, $Z^2$, $Z^3$, $Z^4$, and $Z^5$ in the above formula (7) have the same definition as $Z^1$, $Z^2$, $Z^3$, $Z^4$, and $Z^5$ in the formula (1).)

The (E)-4-(2,4-difluorophenyl)-4-oxo-2-butenoic acid can be synthesized by Friedel-Crafts reaction of 1,3-difluorobenzene and maleic anhydride as shown below. Such Friedel-Crafts reaction is carried out by causing Lewis acid, phosphoric acid, polyphosphoric acid or the like to act as a catalyst, and aluminum chloride is suitably used as a catalyst.

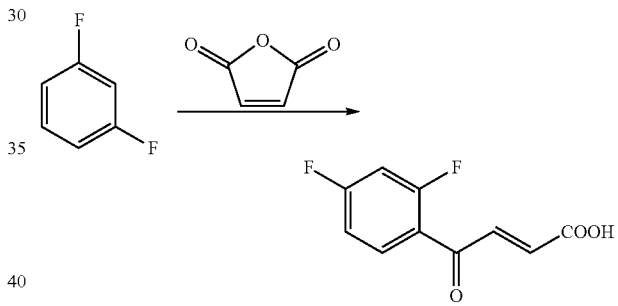

As the indole derivative of the above formula (7), a commercially available product can be used. Commercially available indole derivatives can include 4-fluoroindole, 4-chloroindole, 4-bromoindole, 6-fluoroindole, 6-chloroindole, 6-bromoindole, 5-methylindole, or the like.

In addition, the indole derivative of the above formula (7) can also be obtained by an organic synthesis technique using a known organic chemical reaction. For example, when $R^1$, $R^2$, $R^3$, $R^4$ and $R^5$ are a halogen atom, a halogenating agent such as N-bromosuccinimide, N-chlorosuccinimide, or N-iodosuccinimide can be allowed to act on a commercially available indole to obtain the indole derivative of the above formula (7). When $R^1$, $R^2$, $R^3$ and $R^4$ are a C1 to C6 alkyl group, a C2 to C6 alkenyl group, a C2 to C6 alkynyl group, and an organic oxy group represented by ORE, commercially available indole as mentioned above can be halogenated, followed by reaction with an organolithium reagent such as alkyllithium or Suzuki-Miyaura coupling reaction to obtain an indole derivative of the above formula (7). Further, when $R^3$ is a C1 to C6 alkyl group, it is possible to obtain an indole derivative of the above formula (7) by reacting a C1 to C6 alkyl halide such as bromomethane and bromoethane with a commercially available indole.

All of the organic reactions described above can be carried out in a solvent, respectively, but the solvent is appropriately selected depending on the reaction temperature, reactants and the like. The reaction temperature of the organic reaction is appropriately selected depending on the conditions such as the boiling point of the solvent to be used. When a solvent is used in the above organic reaction, the obtained reaction solution may be concentrated as necessary, and the residue may be then used as it is for the next reaction. After appropriate post-treatment, the residue may be used as the compound of the formula (1). Specific methods for post-treatment can include extraction treatment and/or known purification such as crystallization, recrystallization, chromatography.

The aforementioned method for synthesizing the compound of the formula ($I_O$) can also be used for synthesizing the compound of the formula (II). Specifically, the compound of the formula (II) can be synthesized in the same way as the aforementioned method for synthesizing the compound of the formula ($I_O$) except that a linear amino alcohol with an amino group protected with tert-butoxycarbonyl or a linear amino alcohol having oxygen in the chain and a protected form of indoleacetic acid in which the α-position is substituted by a methyl group are used as starting materials, instead of the alcohol and the protected form of indoleacetic acid used as starting materials. The linear amino alcohol and the linear amino alcohol having oxygen in the chain can each be converted to tert-butoxycarbonylamide by a standard method. Usually, di-tert-butyl carbonate is used. Those skilled in the art readily understand that the protected form of indoleacetic acid in which the α-position is substituted by a methyl group is an intermediate obtained using methyl iodide as the halogen form in the method for synthesizing the compound of the formula ($I_O$). The starting materials thus prepared can be used in the same way as the method for synthesizing the compound of the formula ($I_O$) to synthesize the compound of the formula (II). Specifically, compound #15 mentioned later in Examples can be synthesized as 4-aminobutanol and 1-methoxycarbonyl-3-indoleacetic acid methyl ester as starting materials as shown in the following scheme:

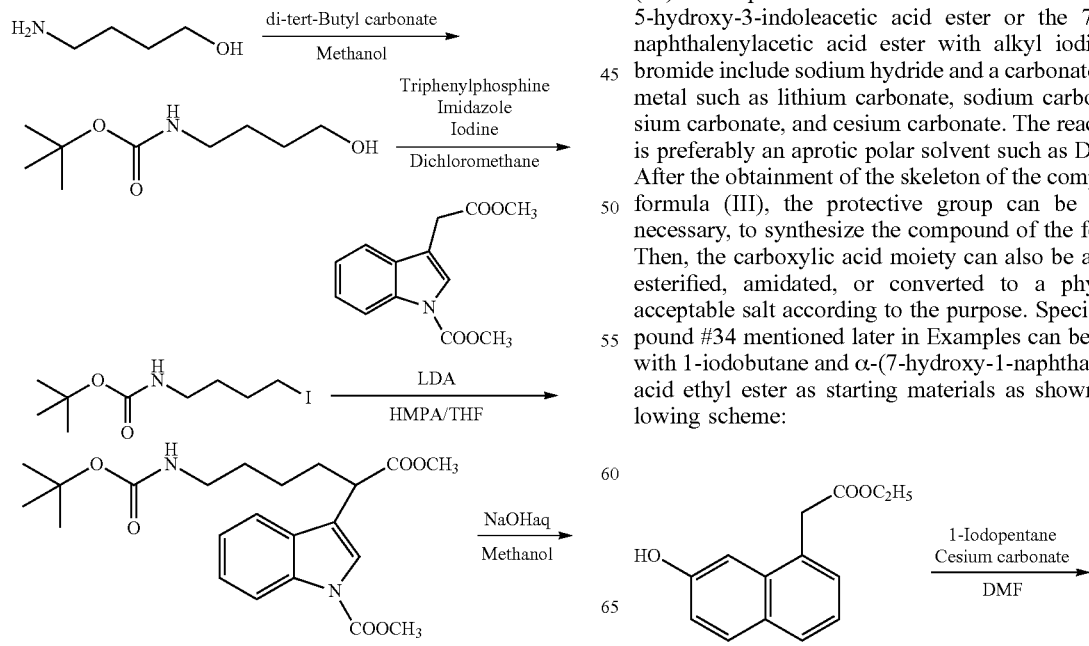

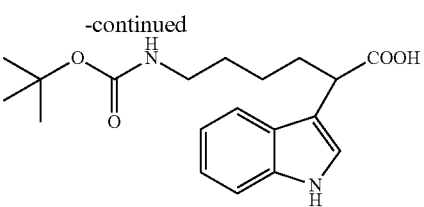

The compound of the formula (III) wherein A is indole or naphthalene can be commonly synthesized with 5-hydroxy-3-indoleacetic acid ester or α-(7-hydroxy-1-naphthalenyl)-acetic acid ester as a starting material. The 5-hydroxy-3-indoleacetic acid ester and the α-(7-hydroxy-1-naphthalenyl)-acetic acid ester can be obtained by the esterification of corresponding carboxylic acids. The 5-hydroxy-3-indoleacetic acid and the α-(7-hydroxy-1-naphthalenyl)-acetic acid have three active protons and two active protons, respectively, which present problems associated with reaction selectivity. For this reason, the alcohol moieties of these compounds are protected, and the protective group can be removed after the esterification to obtain the starting material. Alternatively, α-(7-hydroxy-1-naphthalenyl)-acetic acid ethyl ester can also be synthesized according to a method described in E. Tsuda et. al., "Alkoxy-auxins are selective inhibitors of auxin transport mediated by PIN, ABCB, and AUX1 transporters" Journal of Biological Chemistry, 286 (3), 2354-2364; 2011. In addition, a method for synthesizing the 5-hydroxy-3-indoleacetic acid ester can involve synthesizing an ester with an alcohol used as a solvent with favorable selectivity through a reaction under acidic conditions in a dried alcohol. Examples of conditions for the esterification reaction can include commercially available hydrochloric acid/methanol and a method of blowing dried hydrochloric acid into a dehydrated alcohol. A method of adding dropwise acid chloride to a preliminarily dried alcohol to generate an acid in the system is preferred. Then, the carboxylic acid moiety can be appropriately esterified, amidated, or converted to a physiologically acceptable salt thereof. The starting material thus prepared can be reacted with alkyl iodide or alkyl bromide to construct the basic skeleton of the compound of the formula (III). Examples of the base used in this reaction of the 5-hydroxy-3-indoleacetic acid ester or the 7-hydroxy-1-naphthalenylacetic acid ester with alkyl iodide or alkyl bromide include sodium hydride and a carbonate of an alkali metal such as lithium carbonate, sodium carbonate, potassium carbonate, and cesium carbonate. The reaction solvent is preferably an aprotic polar solvent such as DMF or THF. After the obtainment of the skeleton of the compound of the formula (III), the protective group can be removed, if necessary, to synthesize the compound of the formula (III). Then, the carboxylic acid moiety can also be appropriately esterified, amidated, or converted to a physiologically acceptable salt according to the purpose. Specifically, compound #34 mentioned later in Examples can be synthesized with 1-iodobutane and α-(7-hydroxy-1-naphthalenyl)-acetic acid ethyl ester as starting materials as shown in the following scheme:

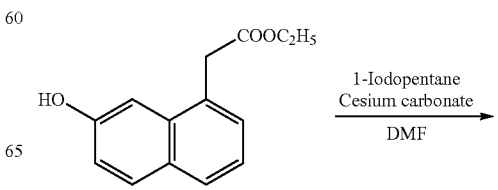

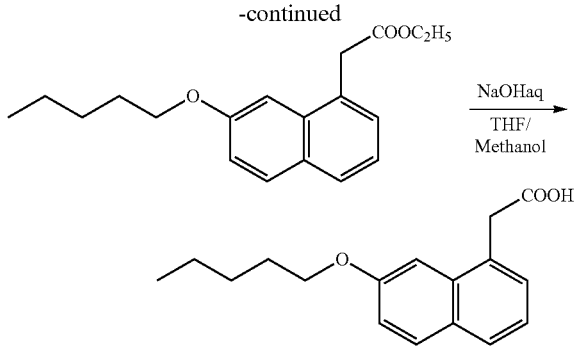

Similarly, compound #35 mentioned later in Examples can be synthesized using 3,5-dimethoxybenzyl bromide and 7-hydroxy-3-indoleacetic acid as starting materials.

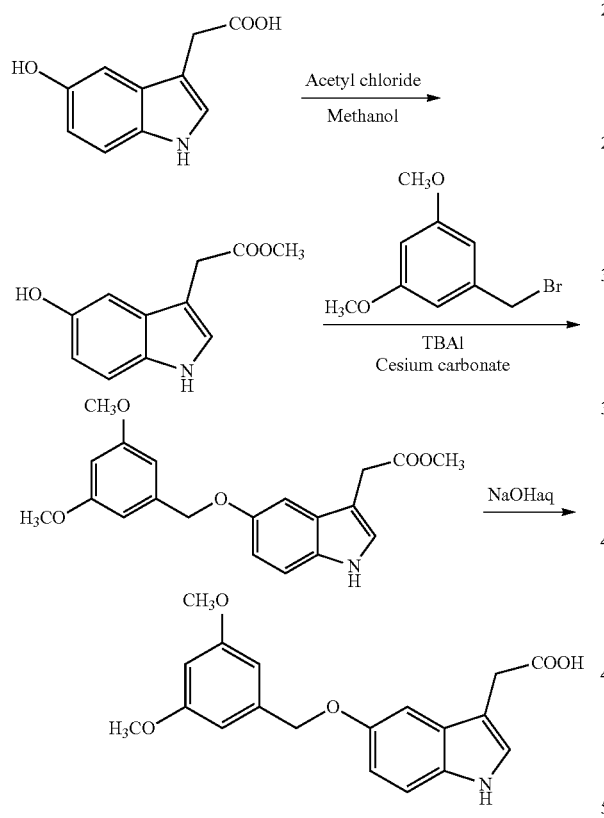

As the compound group of the present invention, compound #5 or a physiologically acceptable salt thereof is preferred of which effect is specifically shown in the examples of the present specification.

Hereinafter, the present invention will be described more specifically with reference to Examples. However, the technical scope of the present invention is not intended to be limited by these examples.

EXAMPLE 1

1. Synthesis of Compound Group of the Present Invention

Starting materials for synthesis, reaction reagents, etc., for use in methods for synthesizing compounds shown below are general commercially available products. As for reaction solvents and reaction temperatures, a reaction is carried out using a solvent and a temperature usually used for the reaction, unless otherwise specified. Each reaction is carried out in an argon or dried nitrogen atmosphere.

Synthesis of Compound #1]

4-Phenyl-2-(4-chloro-1H-indol-3-yl)-4-oxo-butane (compound #1) was synthesized by a method for synthesizing compound #20 mentioned later using 4-chloroindole instead of indole.

[Synthesis of Compound #2 and Compound #3]

4-(4-Chlorophenyl)-2-(1H-indol-3-yl)-4-oxo-butanoic acid (compound #2) and 3-(1H-indol-3-yl)-1-oxo-1-phenyl-butane (compound #3) were each synthesized according to a method described in Sayed, G. H. et al, "Synthesis and reactions of some β-aroyl-α-(indol-3-yl)propionic acids" Journal of the Chemical Society of Pakistan, 7 (4), 263-72; 1985.

(Compound #2)

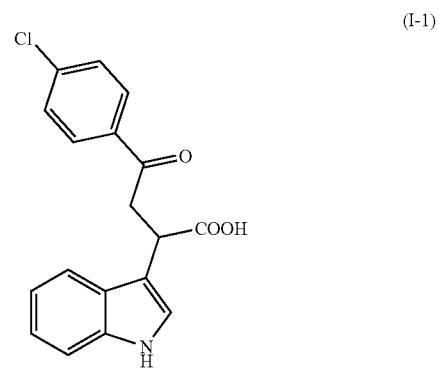 [SMILES: O=C(CC(C(=O)O)c1c[nH]c2ccccc12)c1ccc(Cl)cc1]

Synthesis of compound #4

Trans-4-(4-fluorophenyl)-4-oxo-2-butenoic Acid

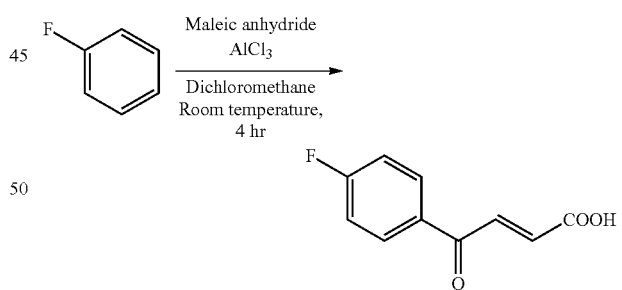

In a 50-mL round-bottomed flask filled with nitrogen, fluorobenzene (0.50 g, 5.21 mmol) was dissolved in dichloromethane (20 mL). To the solution, maleic anhydride (0.51 g, 5.20 mmol) and aluminum chloride (1.40 g, 10.49 mmol) were added, and the mixture was stirred at room temperature for 4 hours. The reaction solution was pH-adjusted to 1 by the addition of 1 N hydrochloric acid (10 mL), followed by extraction with ethyl acetate (40 mL) three times. The organic layer was washed with saturated saline and dehydrated over anhydrous sodium sulfate. The solvent was distilled off under reduced pressure, and then, the residue was purified by recrystallization (benzene) to obtain trans- 4-(4-fluorophenyl)-4-oxo-2-butenoic acid (0.57 g, yield: 56%); Melting point: 114.8 to 119.6° C.; ¹H NMR (CDCl₃): δ 8.06 (m, 2H), 7.98 (d, J=15.4 Hz, 1H), 7.21 (m, 2H), 6.90 (d, J=15.4 Hz, 1H); ¹³C NMR (CDCl₃): δ 187.5, 170.7, 166.3 (d, $J_{C-F}$=255.5 Hz), 138.0, 132.8 (d, $J_{C-F}$=3.2 Hz), 131.7 (d, $J_{C-F}$=9.9 Hz), 131.6, 116.2 (d, $J_{C-F}$=22.1 Hz); IR (neat): 2972, 1705, 1665 cm⁻¹; FAB-MS m/z 195 [M+H]⁺.

4-(4-Fluorophenyl)-2-(1H-indol-3-yl)-4-oxo-butanoic Acid (Compound #4)

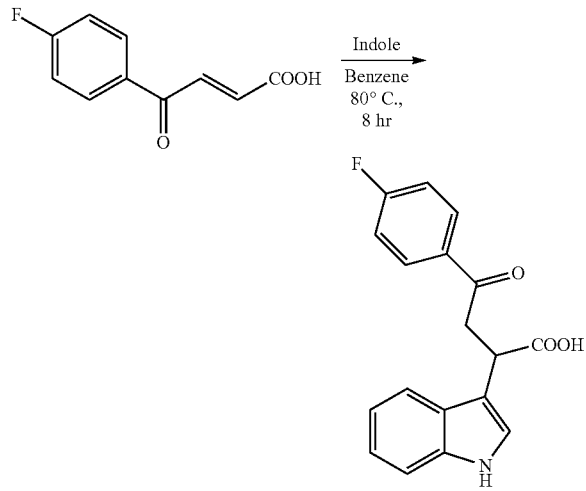

In a 30-mL round-bottomed flask, trans-4-(4-fluorophenyl)-4-oxo-2-butenoic acid (0.21 g, 1.08 mmol) was dissolved in benzene (10 mL). To the solution, indole (0.26 g, 2.19 mmol) was added, and the mixture was stirred at 80° C. for 8 hours and stirred until the temperature became room temperature. The solvent in the reaction solution was distilled off under reduced pressure, and the residue was purified using silica gel column chromatography (chloroform:methanol=20:1) to obtain 4-(4-fluorophenyl)-2-(1H-indol-3-yl)-4-oxo-butanoic acid (compound #4) (0.15 g, yield: 47%); Melting point: 161.6 to 166.6° C.; ¹H NMR (DMSO-d₆): δ 8.13 (m, 2H), 7.68 (d, J=7.9 Hz, 1H), 7.35 (m, 4H), 7.09 (t, J=7.2 Hz, 1H), 7.00 (t, J=7.1 Hz, 1H), 4.34 (dd, J=10.7, 3.9 Hz, 1H), 4.03 (dd, J=18.1, 10.7 Hz, 1H), 3.34 (dd, J=18.1, 3.9 Hz, 1H); ¹³C NMR (DMSO-d₆): δ 197.96, 175.61, 166.00 (d, $J_{C-F}$=250.0 Hz), 137.16, 134.11, 131.93 (d, $J_{C-F}$=10.0 Hz), 127.15, 124.16, 122.07, 119.97, 119.53, 116.6 (d, $J_{C-F}$=22.0 Hz), 112.79, 112.42, 42.03, 38.57; IR (neat): 3419, 2925, 1679 cm⁻¹; HRFAB-MS found m/z 312.1028 [M+H]⁺, calcd for 312.1036 (C₁₈H₁₅FNO₃).

Synthesis of Compound #5

Trans-4-(2,4-difluorophenyl)-4-oxo-2-butenoic Acid

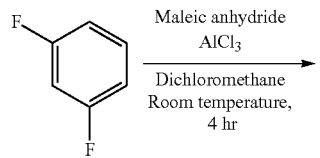

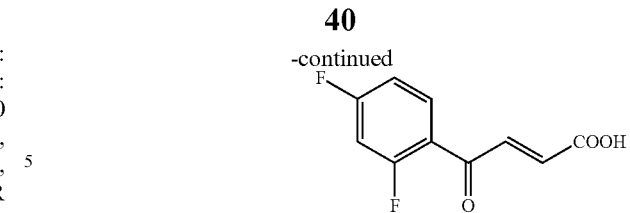

In a 50-mL round-bottomed flask filled with nitrogen, 1,3-difluorobenzene (0.51 g, 4.47 mmol) was dissolved in dichloromethane (20 mL). To the solution, maleic anhydride (0.43 g, 4.46 mmol) and aluminum chloride (1.20 g, 9.01 mmol) were added, and the mixture was stirred at room temperature for 4 hours and stirred until the temperature became room temperature. The reaction solution was pH-adjusted to 1 by the addition of 1 N hydrochloric acid (10 mL), followed by extraction with ethyl acetate (40 mL) three times. The organic layer was washed with saturated saline and dehydrated over anhydrous sodium sulfate. The solvent was distilled off under reduced pressure, and then, the residue was purified by recrystallization from benzene to obtain trans-4-(2,4-difluorophenyl)-4-oxo-2-butenoic acid (0.57 g, yield: 56%); Melting point: 114.8 to 119.6° C.; H NMR (acetone-d₆): δ 7.98 (m, 1H), 7.71 (dd, $J_{H-F}$=15.6, 3.4 Hz, 1H), 7.23 (m, 2H), 6.75 (dd, $J_{H-F}$=15.6, 1.2 Hz, 1H); ¹³C NMR (acetone-d₆): δ 187.2 (d, $J_{C-F}$=2.6 Hz), 166.9 (dd, $J_{C-F}$=254.5, 12.3 Hz), 166.4, 163.4 (dd, $J_{C-F}$=254.5, 12.9 Hz), 140.0 (d, $J_{C-F}$=6.1 Hz), 134.0 (dd, $J_{C-F}$=10.9, 3.6 Hz), 133.0 (d, $J_{C-F}$=1.6 Hz), 123.3 (dd, $J_{C-F}$=12.4, 3.6 Hz), 113.4 (dd, $J_{C-F}$=21.5, 3.6 Hz), 105.8 (dd, $J_{C-F}$=27.3, 26.3 Hz); IR (neat): 2917, 1697, 1661 cm⁻¹; FAB-MS m/z 213 [M+H]⁺.

4-(2,4-Difluorophenyl)-2-(1H-indol-3-yl)-4-oxo-butanoic Acid (Compound #5)

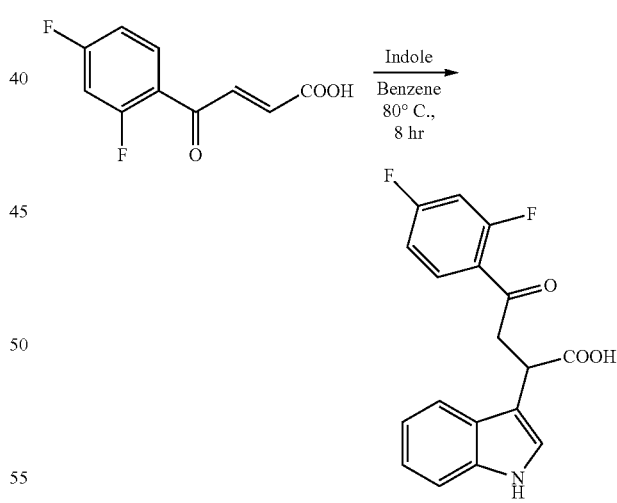

In a 30-mL round-bottomed flask, trans-4-(2,4-difluorophenyl)-4-oxo-2-butenoic acid (0.39 g, 1.84 mmol) was dissolved in benzene (10 mL). To the solution, indole (0.43 g, 2.19 mmol) was added, and the mixture was stirred 80° C. for 8 hours and stirred until the temperature became room temperature. The solvent in the reaction solution was distilled off under reduced pressure, and the residue was purified using silica gel column chromatography (chloroform:methanol=20:1) to obtain 4-(2,4-difluorophenyl)-2-(1H-indol-3-yl)-4-oxo-butanoic acid (0.15 g, yield: 51%);

Melting point: 180.2 to 184.6° C.; $^1$H NMR (DMSO-d$_6$): δ 7.98 (m, 1H), 7.65 (d, J=7.9 Hz, 1H), 7.37 (d, J=8.1 Hz, 1H), 7.42 (m, 1H), 7.28 (d, J=2.3 Hz, 1H), 7.24 (m, 1H), 7.09 (t, J=7.1 Hz, 1H), 7.01 (t, J=7.5 Hz, 1H), 4.34 (dd, J=10.5, 3.5 Hz, 1H), 3.90 (ddd, $J_{H-F}$=18.5, 10.6, 2.4 Hz, 1H), 3.30 (ddd, $J_{H-F}$=18.5, 6.1, 3.5 Hz, 1H); $^{13}$C NMR (DMSO-d$_6$): δ 195.2 (d, $J_{C-F}$=4.1 Hz), 174.8, 165.2 (d, $J_{C-F}$=253.0, 13.4 Hz), 162.2 (d, $J_{C-F}$=255.5, 13.4 Hz), 136.4, 132.7 (dd, $J_{C-F}$=108, 4.1 Hz), 126.3, 123.3, 122.2 (dd, $J_{C-F}$=12.3, 3.6 Hz), 121.4, 119.1, 118.8, 112.6 (dd, $J_{C-F}$=21.1, 3.6 Hz), 111.9, 111.8, 105.4 (dd, $J_{C-F}$=26.1 Hz), 45.6 (d, $J_{C-F}$=6.3 Hz), 37.9; IR (neat): 3382, 2919, 1678 cm$^{-1}$; HRFA-MS found m/z 330. 0910 [M+H]$^+$, calcd for 330. 0942 ($C_{18}H_{14}F_2NO_3$).

Synthesis of Compound #6

Trans-4-(2,4-dimethylphenyl)-4-oxo-2-butenoic Acid

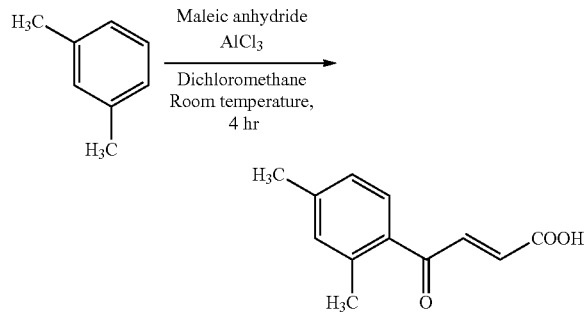

In a 50-mL round-bottomed flask filled with nitrogen, m-xylene (1.00 g, 9.42 mmol) was dissolved in dichloromethane (40 mL). To the solution, maleic anhydride (0.93 g, 9.42 mmol) and aluminum chloride (2.51 g, 18.84 mmol) were added, and the mixture was stirred at room temperature for 4 hours. The reaction solution was pH-adjusted to 1 by the addition of 1 N hydrochloric acid (10 mL), followed by extraction with ethyl acetate (40 mL) three times. The organic layer was washed with saturated saline and dehydrated over anhydrous sodium sulfate. The solvent was distilled off under reduced pressure, and then, the residue was purified by recrystallization (benzene) to obtain trans-4-(2,4-dimethylphenyl)-4-oxo-2-butenoic acid (1.49 g, yield: 77%); Melting point: 85.4 to 88.8° C.; $^1$H NMR (CDCl$_3$): δ 7.75 (d, J=15.6 Hz, 1H), 7.56 (d, J=8.2 Hz, 1H), 7.10 (m, 2H), 6.70 (d, J=15.6 Hz, 1H), 2.50 (s, 3H), 2.38 (s, 3H); $^{13}$C NMR (CDCl$_3$): δ 192.5, 170.9, 143.1, 141.7, 139.5, 133.6, 133.0, 130.9, 130.0, 126.4, 21.5, 21.2; IR (neat): 2986, 1703, 1667 cm$^{-1}$; FAB-MS m/z 205 [M+H]$^+$.

4-(2,4-Dimethylphenyl)-2-(1-propyl-1H-indol-3-yl)-4-oxo-butanoic Acid (Compound #6)

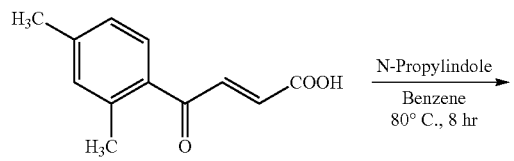

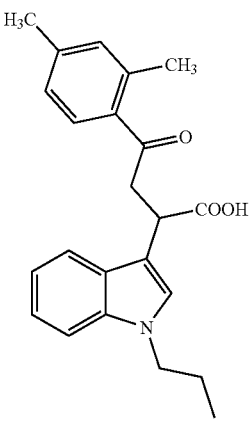

In a 30-mL round-bottomed flask, trans-4-(2,4-dimethylphenyl)-4-oxo-2-butenoic acid (0.50 g, 2.45 mmol) was dissolved in benzene (10 mL). To the solution, N-propylindole (0.85 g, 4.90 mmol) was added, and the mixture was stirred at 80° C. for 8 hours and stirred until the temperature became room temperature. The solvent in the reaction solution was distilled off under reduced pressure, and the residue was purified using silica gel column chromatography (chloroform:acetone=5:1) to obtain 4-(2,4-dimethylphenyl)-2-(1-propyl-1H-indol-3-yl)-4-oxo-butanoic acid (0.98 g, yield: 67%); Melting point: 139 to 141° C.; $^1$H NMR (400 MHz, CDCl$_3$): δ 7.70 (d, J=7.8 Hz, 1H), 7.59 (d, J=7.8 Hz, 1H), 7.28 (d, J=8.2 Hz, 1H), 7.18 (t, J=15.1 Hz, 1H), 7.07 (m, 2H), 6.99 (d, J=8.7 Hz, 2H), 4.56 (dd, J=6.0, 4.1 Hz, 1H), 3.97 (m, 2H), 3.92 (m, 1H), 3.28 (dd, J=17.8, 4.1 Hz, 1H), 2.43 (s, 3H), 2.30 (s, 3H), 1.80 (m, 2H), 0.89 (t, J=14.7, 3H); $^{13}$C NMR (100 MHz, CDCl$_3$): δ 200.9, 179.7, 142.3, 138.9, 136.3, 134.1, 132.8, 129.1, 126.7, 126.2, 126.1, 121.7, 119.4, 119.2, 110.6, 109.5, 48.0, 44.0, 38.0, 23.4, 21.5, 21.3, 11.5; IR (neat): 3428, 2923, 1707 cm; FAB-MS m/z 364 [M+H]$^+$.

4-Phenyl-2-(1H-5-ethoxyindol-3-yl)-4-oxo-butanoic acid (compound #7) was synthesized in the same way as in compound #20 using 5-ethoxyindole instead of indole.

Compounds #8, 13 to 15, 17 to 19, and 21 to 25 were each synthesized with methyl N-methoxycarbonylindoleacetate as a key intermediate.

1-Methoxycarbonylindole-3-acetic Acid Methyl Ester

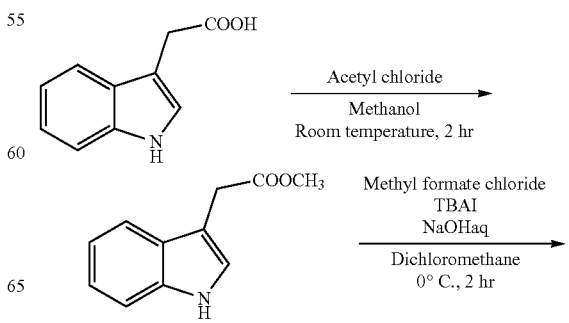

Indole-3-Acetic Acid Methyl Ester

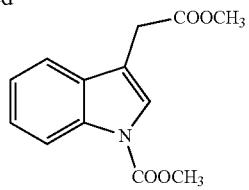

Indole-3-acetic acid (2.00 g, 11.42 mmol) was dissolved in methanol (40 ml). To this solution, acetyl chloride (0.5 ml, 6.688 mmol) was added dropwise, and the mixture was stirred at room temperature for 2 hours. After the reaction was confirmed by TLC to be complete, the reaction was terminated by the addition of a saturated aqueous solution of sodium bicarbonate, followed by extraction with ethyl acetate (50 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=7:3) to obtain indole-3-acetic acid methyl ester (2.14 g, yield: 99%): $^1$H NMR (400 MHz, CDCl$_3$): δ 8.13 (s, 1H), 6.97 (s, 1H), 7.59 (d, J=7.7 Hz, 1H), 7.23 (d, J=7.9 Hz, 1H), 7.10-7.19 (m, 2H), 3.67 (s, 3H), 3.76 (s, 2H); $^{13}$C NMR (100 MHz, CDCl$_3$): δ 172.3, 136.0, 127.1, 123.2, 122.0, 119.5, 118.6, 111.2, 108.0, 51.9, 31.0; IR (neat): 3410, 1730, 1458, 1435, 1337, 1164, 1095, 1011 cm$^{-1}$; EI-MS m/z 189 [M]$^+$.

1-Methoxycarbonyl-3-Indoleacetic Acid Methyl Ester

Methyl indole-3-acetate (2.00 g, 10.57 mmol) was dissolved in dichloromethane (30 ml). To this solution, tetrabutylammonium iodide (TBAI, 30.0 mg, 0.081 mmol) and a 30% aqueous sodium hydroxide solution (24 ml) were added, and the mixture was cooled to 0° C. To the reaction solution, methyl formate chloride (1.96 g, 20.73 mmol) was added, and the mixture was stirred at 0° C. for 2 hours. After the reaction was confirmed by TLC to be complete, the reaction was terminated by the addition of 6 N hydrochloric acid. Water (50 ml) was added thereto, followed by extraction with chloroform (50 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=8:2) to obtain methyl N-methoxycarbonylindole-3-acetate (2.26 g, yield: 87%): $^1$H NMR (400 MHz, CDCl$_3$): δ 8.18 (d, J=7.0 Hz, 1H), 7.59 (s, 1H), 7.53 (d, J=7.7 Hz, 1H), 7.35 (t, J=7.5 Hz, 1H), 7.27 (t, J=7.4 Hz, 1H), 4.00 (s, 3H), 3.72 (s, 3H), 3.71 (s, 2H); $^{13}$C NMR (100 MHz, CDCl$_3$): δ 171.1, 151.1, 135.2, 129.9, 124.6, 123.8, 122.8, 118.9, 115.0, 113.8, 53.5, 51.9, 30.6; IR (neat): 1746, 1455, 1382, 1258, 1164, 1089, 1018 cm$^{-1}$; EI-MS: m/z 247 [M]$^+$.

Compounds #8 and 9 were each synthesized according to a method described in International Publication No. WO 2010/045451.

Synthesis of Compound #8

2-(N-tert-Butoxycarbonyl-4-piperidinyl)ethanol

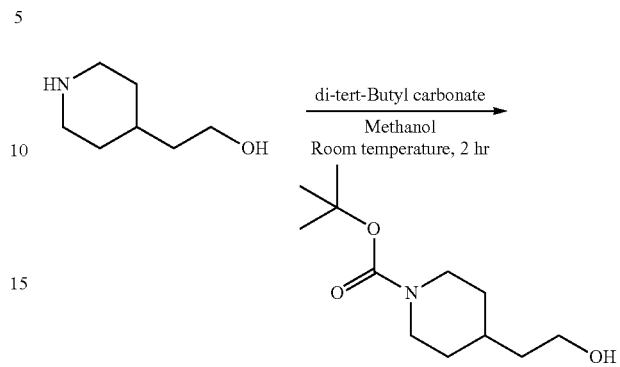

2-(4-Piperidinyl)ethanol (1.0 g, 7.7 mmol) was dissolved in methanol (50 ml). To this solution, di-tert-butyl carbonate (2.0 g, 9.3 mmol) was added, and the mixture was stirred at room temperature for 2 hours. After the reaction was confirmed by TLC to be complete, the solvent was distilled off under reduced pressure, and the residue was purified using silica gel column chromatography (hexane:acetone=9:1) to obtain N-tert-butoxycarbonyl-2-(4-piperidinyl)ethanol (1.68 g, yield: 95%).

Ethane 2-(N-tert-butoxycarbonyl-4-piperidinyl)-1-iodide

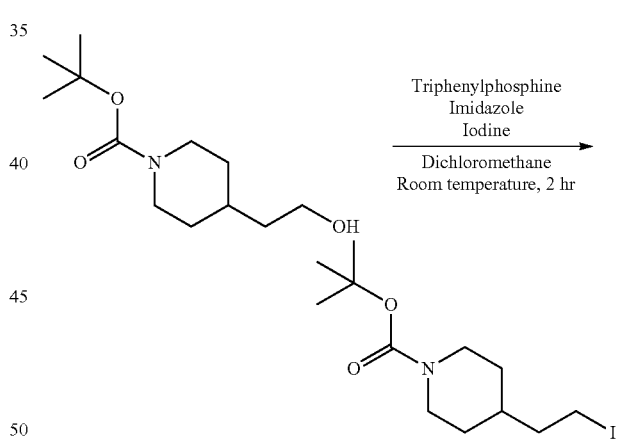

Triphenylphosphine (2.56 g, 9.760 mmol) and imidazole (0.66 g, 9.694 mmol) were dissolved in dichloromethane (15 ml), and the solution was stirred for 5 minutes. Then, iodine (2.47 g, 9.732 mmol) was added thereto, and the mixture was stirred for 10 minutes. A dichloromethane (4 ml) solution of N—N-tert-butoxycarbonyl-2-(4-piperidinyl)ethanol (1.49 g, 6.497 mmol) was added dropwise thereto, and the mixture was stirred at room temperature for 2 hours. After the reaction was confirmed by TLC to be complete, the reaction solution was filtered through celite, and a 5% aqueous sodium thiosulfate solution was added to the filtrate to remove iodine. The organic layer was washed twice with saturated saline and dehydrated over anhydrous sodium sulfate. The solvent was distilled off under reduced pressure, and then, the residue was purified using silica gel column chromatography (hexane:ethyl acetate=9:1) to obtain ethane N-tert-butoxycarbonyl-2-(4-piperidinyl)-1-iodide (2.13 g, yield: 96%).

α-[2-(N-tert-Butoxycarbonyl-4-piperidinyl)-1-ethyl]-1-methoxycarbonyl-3-indoleacetic Acid Methyl Ester

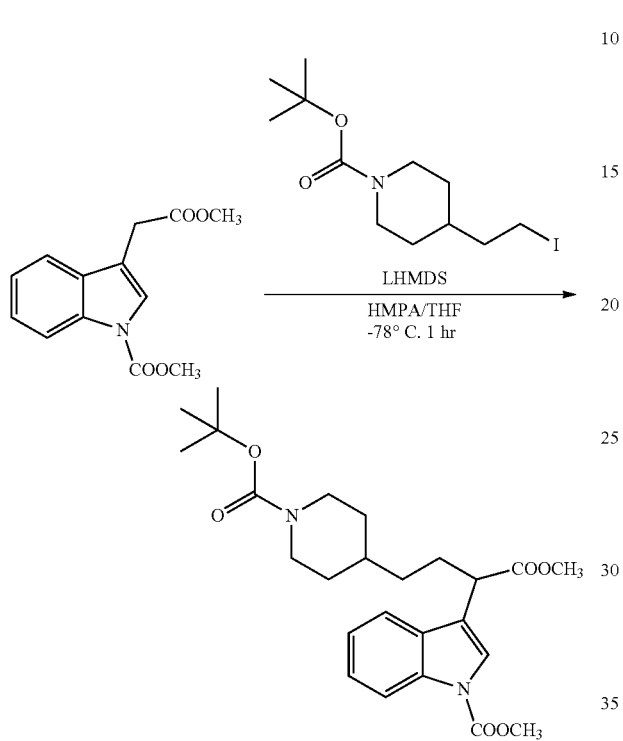

In a nitrogen atmosphere, 1-methoxycarbonyl-3-indoleacetic acid methyl ester (500 mg, 2.022 mmol) and hexamethylphosphoric triamide (HMPA, 1.81 g, 10.11 mmol) were dissolved in tetrahydrofuran (4 ml), and the solution was cooled to −78° C. A 1.5 M solution of lithium diisopropylamide (LDA) in cyclohexane (2.16 ml, 1.6 eq) was slowly added dropwise thereto, and the mixture was stirred at −78° C. for 0.5 hours. To this reaction solution, a tetrahydrofuran (2 ml) solution of ethane 2-(N-tert-butoxycarbonyl-4-piperidinyl)-1-iodide (686 mg, 2.022 mmol) was slowly added dropwise, and the mixture was stirred at −78° C. for 1 hour. After the reaction was confirmed by TLC to be complete, the temperature was adjusted to 0° C., and the reaction was terminated by the addition of water (15 ml), followed by extraction with ethyl acetate (15 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=8:2) to obtain α-2-(N-tert-butoxycarbonyl-4-piperidinyl)-ethyl-1-methoxycarbonyl-3-indoleacetic acid methyl ester (626 mg, yield: 68%): $^1$H NMR (400 MHz, CDCl$_3$): δ 8.19 (m, 1H), 7.61 (d, J=7.8 Hz, 1H), 7.56 (s, 1H), 7.35 (t, J=7.7 Hz, 1H), 7.25-7.30 (m, 1H), 3.79-4.15 (m, 5H), 3.77 (t, J=7.6 Hz, 1H), 3.68 (s, 3H), 2.65 (m, 2H), 2.05 (m, 2H), 1.65 (m, 2H), 1.25-1.50 (m, 12H), 1.05-1.19 (m, 2H); $^{13}$C NMR (100 MHz, CDCl$_3$): δ 173.9, 168.0, 154.8, 135.4, 129.3, 124.8, 123.1, 122.9, 119.2, 119.2, 115.2, 79.1, 53.7, 53.0, 52.1, 48.9, 43.7, 42.7, 35.9, 34.3, 32.0, 29.5, 28.4; FAB-MS: m/z 459 [M+H]$^+$.

α-[2-(1-Acetyl-4-piperidinyl)-ethyl]-1-methoxycarbonyl-3-indoleacetic Acid Methyl Ester

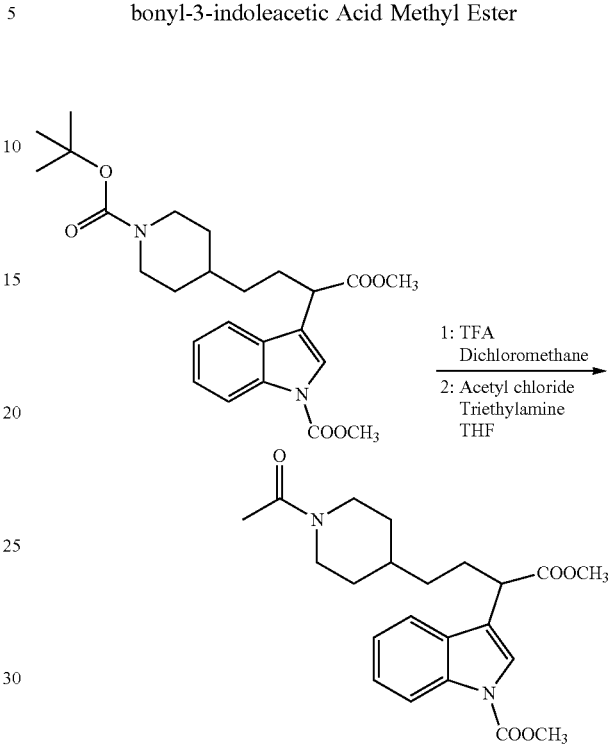

α-[2-(N-tert-Butoxycarbonyl-4-piperidinyl)-1-ethyl]-1-methoxycarbonyl-3-indoleacetic acid methyl ester (100 mg, 0.218 mmol) was dissolved in dichloromethane (2 ml). To the solution, trifluoroacetic acid (1.0 ml, 13.07 mmol) was added, and the mixture was stirred at room temperature for 5 minutes. The reaction solution was added dropwise to a 10% aqueous sodium carbonate solution (10 mL) to terminate the reaction. This solution was subjected to extraction with ethyl acetate (10 mL) three times. The organic layer was washed twice with saturated saline (10 mL) and dehydrated over anhydrous sodium sulfate. The solvent was distilled off under reduced pressure to obtain α-[2-(4-piperidinyl)-ethyl]-1-methoxycarbonyl-3-indoleacetic acid methyl ester (74.1 mg). This compound (74.1 mg, 0.207 mmol) was dissolved in tetrahydrofuran (3 mL). To the solution, triethylamine (0.2 mL) and acetyl chloride (10 mg) were added, and the mixture was stirred at room temperature for 1.5 hours. The reaction was terminated by the addition of a saturated aqueous solution of ammonium chloride (10 mL), followed by extraction with ethyl acetate (10 mL) three times. The organic layer was washed twice with saturated saline (10 mL) and dehydrated over anhydrous sodium sulfate. The solvent was distilled off under reduced pressure, and then, the residue was purified using silica gel column chromatography (chloroform:acetone=9:1) to obtain α-[2-(1-acetyl-4-piperidinyl)-ethyl]-1-methoxycarbonyl-3-indoleacetic acid methyl ester (53.9 mg, yield: 65%): $^1$H NMR (400 MHz, CDCl$_3$): δ 8.18 (d, J=6.7 Hz, 1H), 7.61 (d, J=7.8 Hz, 1H), 7.56 (s, 1H), 7.35 (t, J=8.4 Hz, 1H), 7.25-7.28 (m, 1H), 4.57 (d, J=12.8 Hz, 1H), 4.03 (s, 3H), 3.73-3.79 (m, 2H), 3.68 (s, 3H), 2.99 (t, J=12.9 Hz, 1H), 2.50 (t, J=12.6 Hz, 1H), 1.91-2.19 (m, 5H), 1.73 (t, J=10.4 Hz, 2H), 1.49 (m, 1H), 1.26-1.32 (m, 2H), 1.05-1.12 (m, 2H); $^{13}$C NMR (100

MHz, CDCl$_3$): δ 173.8, 168.7, 151.2, 135.4, 129.3, 124.8, 122.9, 119.2, 119.1, 115.2, 53.7, 52.1, 46.6, 42.7, 41.7, 35.9, 34.2, 32.5, 31.6, 29.2, 21.4; FAB-MS: m/z 401 [M+H]$^+$.

α-2-(1-Acetyl-4-piperidinyl)-ethyl-3-indoleacetic Acid (Compound #8)

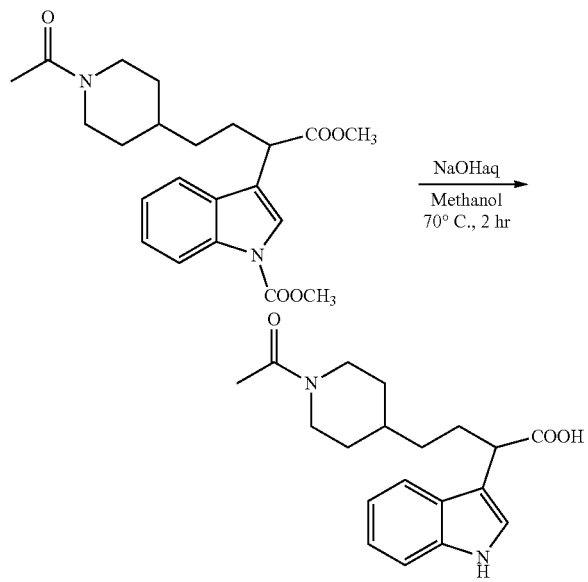

α-2-(1-Acetyl-4-piperidinyl)-ethyl-N-methoxycarbonyl-3-indoleacetic acid methyl ester (48.0 mg, 0.120 mmol) was dissolved in methanol (2 ml). To this solution, a 2 N aqueous sodium hydroxide solution (0.5 ml) was added, and the mixture was stirred at 70° C. for 2 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:acetone=3:2) to obtain α-2-(1-acetyl-4-piperidinyl)-ethyl-3-indoleacetic acid (compound #8) (25.5 mg, yield: 65%: $^1$H NMR (400 MHz, CDCl$_3$): δ 8.54 (s, 1H), 7.67 (d, J=7.9 Hz, 1H), 7.31 (d, J=8.0 Hz, 1H), 7.16 (t, J=7.7 Hz, 1H), 7.07-7.11 (m, 2H), 4.48 (d, J=12.7 Hz, 1H), 3.81 (t, J=7.5 Hz, 1H), 3.66 (d, J=13.2 Hz, 1H), 2.89 (t, J=12.5 Hz, 1H), 2.43 (t, J=12.6 Hz, 1H), 1.86-2.17 (m, 5H), 1.62 (t, J=16.5 Hz, 2H), 1.41 (m, 1H), 1.22-1.28 (m, 2H), 0.93-1.01 (m, 2H); $^{13}$C NMR (100 MHz, CDCl$_3$): δ 178.8, 169.3, 136.2, 126.5, 122.3, 122.0, 119.5, 119.1, 113.3, 111.4, 46.7, 43.1, 42.0, 35.7, 34.2, 32.5, 31.6, 29.7, 21.3; IR (neat): 3410, 1699, 1454, 1271 cm$^{-1}$; FAB-MS: m/z 329 [M+H]$^+$.

α-2-(1-Acetyl-4-piperidinyl)-methyl-3-indoleacetic acid (compound #9) was synthesized by the same approach as in compound #8 using N-tert-butoxycarbonyl-4-piperidinyl-methanol instead of 2-(N-tert-butoxycarbonyl-4-piperidinyl)ethanol.

Synthesis of Compound #10

α-4-Aminobutyl-N-methoxycarbonyl-3-indoleacetic Acid Methyl Ester

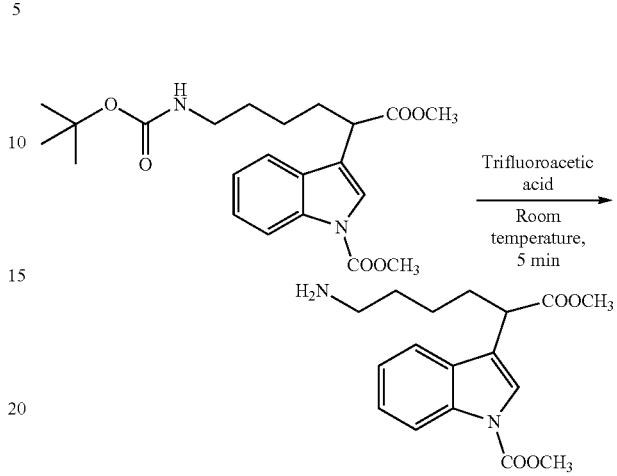

To α-(N-tert-butoxycarbonyl-4-amino-1-butyl)-1-methoxycarbonyl-3-indoleacetic acid methyl ester (150 mg, 0.358 mmol), trifluoroacetic acid (0.4 ml, 5.227 mmol) was added, and the mixture was stirred at room temperature. After 5 minutes, the reaction solution was added dropwise to an aqueous sodium bicarbonate solution to terminate the reaction. Water (5 ml) was added thereto, followed by extraction with ethyl acetate (5 ml) three times. The organic layer was washed twice with saturated saline and dehydrated over anhydrous sodium sulfate. The solvent was distilled off under reduced pressure to obtain α-4-aminobutyl-N-methoxycarbonyl-3-indoleacetic acid methyl ester.

α-[N-(1-Acetylpyrrolidine-2-carbonyl)-4-aminobutyl]-N-methoxycarbonyl-3-indoleacetic Acid Methyl Ester

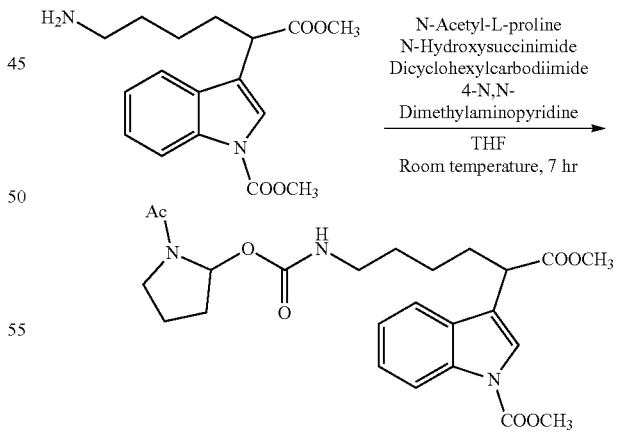

α-4-Aminobutyl-N-methoxycarbonyl-3-indoleacetic acid methyl ester (150 mg, 0.493 mmol) was dissolved in tetrahydrofuran (3 ml). To this solution, N-acetyl-L-proline (116 mg, 0.738 mmol), N-hydroxysuccinimide (85.0 mg, 0.739 mmol), dicyclohexylcarbodiimide (152 mg, 0.737 mmol), and 4-N,N-dimethylaminopyridine (72.0 mg, 0.589 mmol) were added, and the mixture was stirred at room temperature for 7 hours. The reaction was terminated with a saturated aqueous solution of ammonium chloride, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:acetone=7:3) to obtain α-[N-(1-acetylpyrrolidine-2-carbonyl)-4-aminobutyl]-N-methoxycarbonyl-3-indoleacetic acid methyl ester (107 mg, yield: 49%): $^1$H NMR (400 MHz, CDCl$_3$): δ 8.17 (d, J=7.1 Hz, 1H), 7.61 (d, J=7.7 Hz, 1H), 7.55 (s, 1H), 7.33 (t, J=7.8 Hz, 1H), 7.25 (t, J=7.4 Hz, 1H), 7.18 (s, 1H), 4.50 (d, J=7.3 Hz, 1H), 4.02 (s, 3H), 3.80 (t, J=7.6 Hz, 1H), 3.67 (s, 3H), 3.36-3.58 (m, 2H), 3.10-3.26 (m, 2H), 1.76-2.40 (m, 9H), 1.49-1.56 (m, 2H), 1.33-1.38 (m, 2H); $^{13}$C NMR (100 MHz, CDCl$_3$): δ 173.8, 171.0, 170.8, 151.1, 135.3, 129.2, 124.6, 122.9, 122.8, 119.2, 119.1, 115.0, 59.4, 53.6, 51.9, 48.1, 42.3, 38.9, 31.5, 29.0, 27.2, 24.8, 24.7, 22.3; FAB-MS: m/z 458 [M+H]$^+$.

α-[N-(1-Acetylpyrrolidine-2-carbonyl)-4-aminobutyl]-3-indoleacetic Acid (Compound #10)

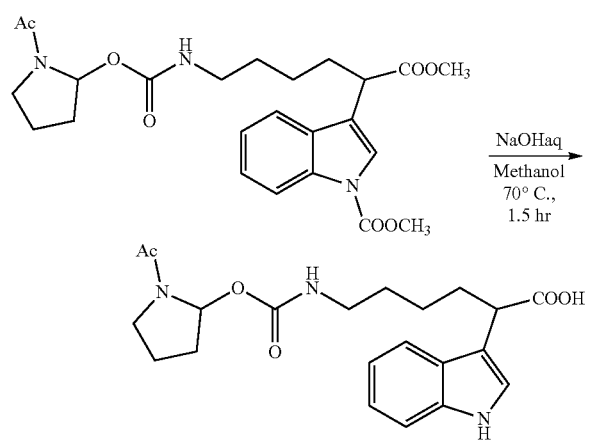

α-[N-(1-Acetylpyrrolidine-2-carbonyl)-4-aminobutyl]-N-methoxycarbonyl-3-indoleacetic acid methyl ester (80.0 mg, 0.175 mmol) was dissolved in methanol (2 ml). To this solution, a 2 N aqueous sodium hydroxide solution (0.5 ml) was added, and the mixture was stirred at 70° C. for 1.5 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=9:1) to obtain α-[N-(1-acetylpyrrolidine-2-carbonyl)-4-aminobutyl]-3-indoleacetic acid (compound #10) (63.6 mg, yield: 94%): $^1$H NMR (400 MHz, acetone-d$_6$): δ 10.21 (s, 1H), 8.03 (s, 1H), 7.70 (d, J=7.8 Hz, 1H), 7.38 (d, J=8.0 Hz, 1H), 7.27 (s, 1H), 7.09 (t, J=7.3 Hz, 1H), 7.01 (t, J=7.6 Hz, 1H), 4.35 (d, J=7.2 Hz, 1H), 3.85 (t, J=7.6 Hz, 1H), 3.53 (m, 1H), 3.40-3.46 (m, 1H), 3.23 (m, 1H), 3.10-3.17 (m, 1H), 1.85-2.14 (m, 9H), 1.36-1.50 (m, 4H); $^{13}$C NMR (100 MHz, acetone-d$_6$): δ 175.8, 172.1, 170.3, 137.3, 127.5, 123.3, 121.9, 119.7, 119.3, 114.1, 112.0, 60.5, 48.3, 43.3, 39.2, 32.9, 32.5, 25.4, 25.1, 22.2; IR (Neat): 3300, 1634, 1456, 1245 cm; FAB-MS: m/z 386 [M+H]$^+$.

Synthesis of Compound #11

α-[2-(2-Aminoethoxy)-ethyl]-N-methoxycarbonyl-3-indoleacetic Acid Methyl Ester

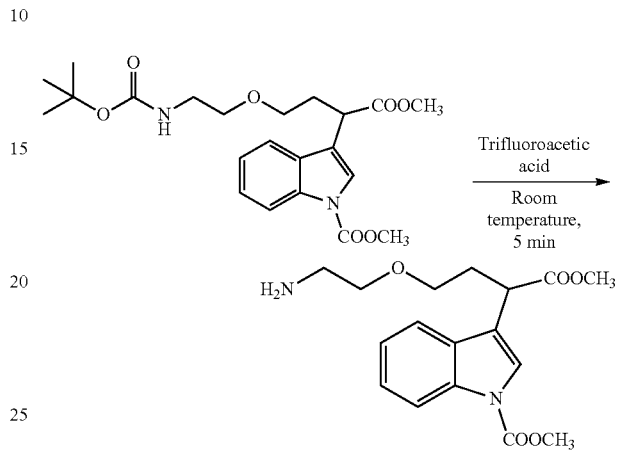

To α-[N-tert-butoxycarbonyl-(2-aminoethoxyethyl)]-1-methoxycarbonyl-3-indoleacetic acid methyl ester (140 mg, 0.322 mmol), trifluoroacetic acid (0.3 ml, 3.920 mmol) was added, and the mixture was stirred at room temperature. After 5 minutes, the reaction solution was added dropwise to an aqueous sodium bicarbonate solution to terminate the reaction. Water (5 ml) was added thereto, followed by extraction with ethyl acetate (5 ml) three times. The organic layer was washed twice with saturated saline and dehydrated over anhydrous sodium sulfate. The solvent was distilled off under reduced pressure to obtain α-[2-(2-aminoethoxy)-ethyl]-N-methoxycarbonyl-3-indoleacetic acid methyl ester (80.0 mg, yield: 74%).

α-{N-(1-Acetylpyrrolidine-2-carbonyl)-[2-(2-aminoethoxy)-ethyl]}-N-methoxycarbonyl-3-indoleacetic Acid Methyl Ester

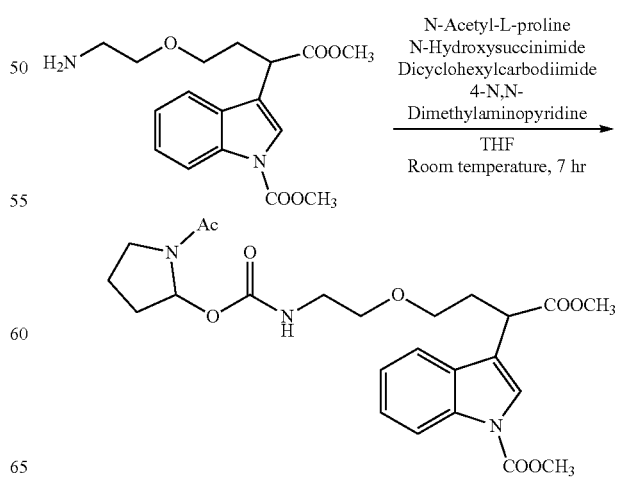

α-[2-(2-Aminoethoxy)-ethyl]-N-methoxycarbonyl-3-indoleacetic acid methyl ester (80.0 mg, 0.239 mmol) was dissolved in tetrahydrofuran (3 ml). To this solution, N-acetyl-L-proline (56.4 mg, 0.359 mmol), N-hydroxysuccinimide (41.2 mg, 0.358 mmol), dicyclohexylcarbodiimide (74.0 mg, 0.359 mmol), and 4-N,N-dimethylaminopyridine (35.0 mg, 0.286 mmol) were added, and the mixture was stirred at room temperature for 7 hours. The reaction was terminated with a saturated aqueous solution of ammonium chloride, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:acetone=7:3) to obtain α-[N-(1-acetylpyrrolidine-2-carbonyl)-4-aminobutyl]-N-methoxycarbonyl-3-indoleacetic acid methyl ester (76.1 mg, yield: 67%): $^1$H NMR (400 MHz, CDCl$_3$): δ 8.18 (d, J=7.1 Hz, 1H), 7.57-7.66 (m, 2H), 7.35 (t, J=7.7 Hz, 1H), 7.25-7.28 (m, 2H), 4.56 (t, J=8.3 Hz, 1H), 4.09 (t, J=7.6 Hz, 1H), 4.03 (s, 3H), 3.68 (s, 3H), 3.59 (t, J=9.0 Hz, 1H), 3.32-3.52 (m, 7H), 2.36-2.48 (m, 2H), 1.84-2.18 (m, 7H), 1.49-1.56 (m, 2H), 1.33-1.38 (m, 2H); $^{13}$C NMR (100 MHz, CDCl$_3$): δ 174.2, 171.5, 170.8, 151.1, 135.5, 129.3, 124.8, 123.1, 123.0, 119.4, 118.9, 115.2, 69.4, 68.4, 59.2, 53.8, 52.2, 48.2, 39.5, 39.2, 32.2, 27.8, 25.0, 22.5; FAB-MS: m/z 474 [M+H]$^+$.

α-[N-(1-Acetylpyrrolidine-2-carbonyl)-4-aminobutyl]-3-indoleacetic Acid (Compound #11)

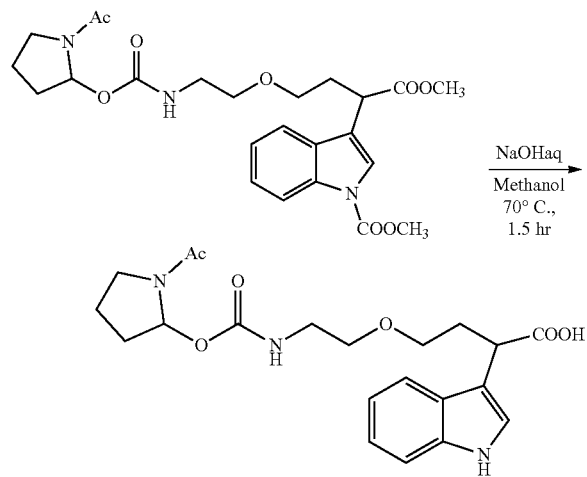

α-[N-(1-Acetylpyrrolidine-2-carbonyl)-4-aminobutyl]-N-methoxycarbonyl-3-indoleacetic acid methyl ester (60.0 mg, 0.127 mmol) was dissolved in methanol (2 ml). To this solution, a 2 N aqueous sodium hydroxide solution (0.5 ml) was added, and the mixture was stirred at 70° C. for 1.5 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=9:1) to obtain α-[N-(1-acetylpyrrolidine-2-carbonyl)-4-aminobutyl]-3-indoleacetic acid (compound #11) (36.6 mg, yield: 72%): $^1$H NMR (400 MHz, acetone-d$_6$): δ 8.48 (d, J=13.4 Hz, 1H), 7.70 (d, J=7.9 Hz, 1H), 7.34 (d, J=8.1 Hz, 1H), 7.09-7.21 (m, 3H), 4.67 (t, J=8.3 Hz, 1H), 4.40-4.11 (m, 1H), 3.18-3.76 (m, 8H), 2.46-2.67 (m, 4H), 1.86-2.22 (m, 7H); $^{13}$C NMR (100 MHz, acetone-d$_6$): δ 178.0, 171.6, 171.2, 136.1, 126.5, 122.3, 122.0, 119.4, 118.9, 113.7, 111.2, 69.3, 68.6, 60.0, 48.5, 41.2, 39.9, 33.7, 29.1, 24.8, 22.3; IR (Neat): 3317, 1634, 1456, 1247, 1119 cm$^{-1}$; FAB-MS: m/z 402 [M+H]$^+$.

Synthesis of compound #12

α-(N-tert-Butoxycarbonyl-6-amino-1-hexyl)-α-(1-naphthyl)-acetic Acid Methyl Ester

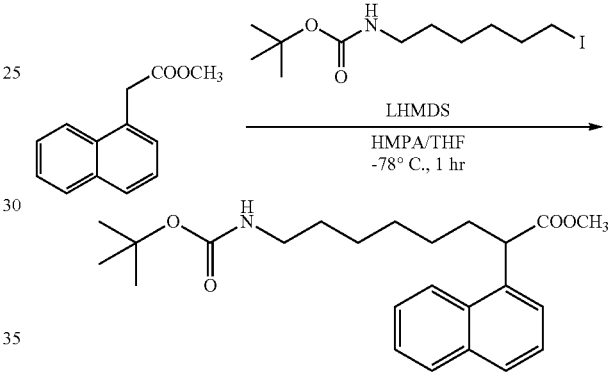

α-(1-Naphthyl)-acetic acid methyl ester (150 mg, 0.75 mmol) was dissolved in tetrahydrofuran. To the solution, hexamethylphosphoramide (HMPA, 671 mg, 3.75 mmol) was added, and the mixture was cooled to −78° C. To this solution, lithium diisopropylamide (1.5 M solution in cyclohexane, 0.75 ml, 1 mmol) was added dropwise, and the mixture was stirred at −78° C. for 30 minutes. Then, a tetrahydrofuran solution (2 mL) of N-tert-butoxycarbonyl-6-amino-1-iodohexane (270 mg, 0.82 mmol) was added dropwise thereto, and the mixture was stirred at −78° C. for 1 hour. The temperature of the reaction solution was raised to 0° C. over 15 minutes, and then, water (50 mL) was added to the solution, followed by extraction with ethyl acetate (50 mL) twice. The organic layer was washed with a saturated ammonium chloride solution (20 mL) and subsequently saline (20 mL) and then dehydrated over sodium sulfate to dryness under reduced pressure. The reaction product was purified using silica gel column chromatography (hexane:ethyl acetate=8:2) to obtain α-(N-tert-butoxycarbonyl-6-amino-1-hexyl)-α-(1-naphthyl)-acetic acid methyl ester (271 mg, yield: 91%): $^1$H NMR (400 MHz, CDCl$_3$) 8.11 (d, J=8.5 Hz, 1H), 7.83 (d, J=8.0 Hz, 1H), 7.74 (d, J=8.1 Hz, 1H), 7.40-7.54 (m, 4H), 4.71 (s, 1H), 4.36 (t, J=7.8 Hz, 1H), 3.61 (s, 3H), 3.04 (m, 2H), 2.07 (m, 2H), 1.24-1.48 (m, 17H); $^{13}$C NMR (100 MHz, CDCl$_3$): δ 174.7, 155.9, 135.3, 133.8, 131.3, 128.8, 127.5, 126.1, 125.4, 125.3, 124.6, 122.8, 78.7, 51.8, 46.5, 40.3, 32.9, 29.7, 28.9, 28.2, 27.6, 26.3; FAB-MS: m/z 400 [M+H]$^+$.

α-(N-tert-Butoxycarbonyl-6-amino-1-hexyl)-α-(1-naphthyl)-acetic Acid (Compound #12)

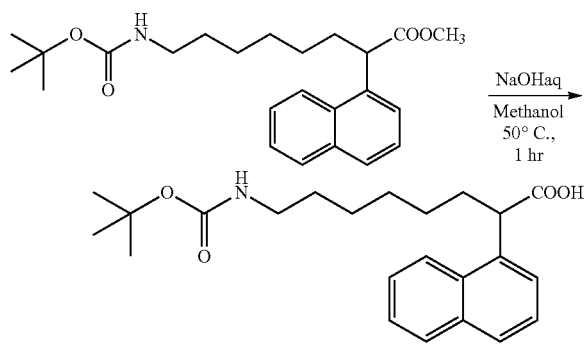

α-(N-tert-Butoxycarbonyl-6-amino-1-hexyl)-α-(1-naphthyl)-acetic acid methyl ester (100 mg, 0.25 mmol) was dissolved in a mixed solution of methanol and an aqueous sodium hydroxide solution (2 N aqueous sodium hydroxide solution:methanol=1:4, 5 mL), and the solution was heated at 50° C. for 1 hour. The reaction solution was pH-adjusted to 3.5 with 6 N hydrochloric acid, and methanol was removed by distillation under reduced pressure. To this solution, water (15 mL) was added, followed by extraction with ethyl acetate (50 mL) twice. The organic layer was washed with a saturated ammonium chloride solution (20 mL) and subsequently saline (20 mL) and then dehydrated over sodium sulfate to dryness under reduced pressure. The reaction product was purified using silica gel column chromatography (chloroform:methanol=95:5) to obtain α-(N-tert-butoxycarbonyl-6-amino-1-hexyl)-α-(1-naphthyl)-acetic acid (compound #12) (90 mg, yield: 93%): $^1$H NMR (400 MHz, CDCl$_3$): δ 8.13 (d, J=8.4 Hz, 1H), 7.84 (d, J=7.9 Hz, 1H), 7.75 (d, J=8.1 Hz, 1H), 7.41-7.53 (m, 4H), 4.56 (s, 1H), 4.35 (t, J=7.4 Hz, 1H), 3.03 (m, 2H), 2.05 (m, 2H), 1.22-1.46 (m, 17H); $^{13}$C NMR (100 MHz, CDCl$_3$) 179.0, 156.0, 135.1, 133.9, 131.6, 128.9, 127.7, 126.2, 125.5, 125.4, 124.9, 123.1, 79.0, 46.6, 40.4, 32.7, 29.8, 29.0, 28.3, 27.7, 26.4; IR (neat): 3417, 1705, 1457, 1268, 1099 cm; FAB-MS: m/z 386 [M+H]$^+$.

Synthesis of Compound #13

N-tert-Butoxycarbonyl-6-amino-1-hexanol

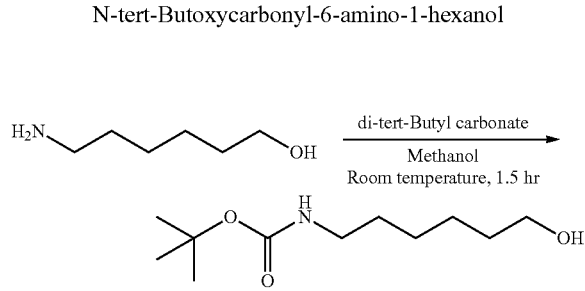

6-Amino-1-hexanol (1.0 g, 8.533 mmol) was dissolved in methanol (10 ml). To this solution, di-tert-butyl carbonate (1.86 g, 8.522 mmol) was added, and the mixture was stirred at room temperature for 1.5 hours. After the reaction was confirmed by TLC to be complete, the solvent was distilled off under reduced pressure, and the residue was purified using silica gel column chromatography (hexane:acetone=9:1) to obtain N-tert-butoxycarbonyl-6-aminohexanol (1.80 g, yield: 97%).

N-tert-Butoxycarbonyl-6-amino-1-iodohexane

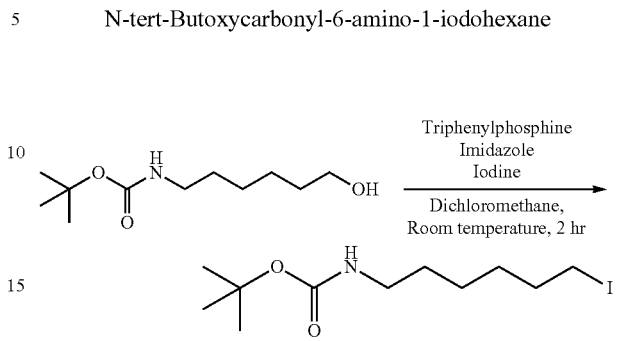

Triphenylphosphine (2.35 g, 8.96 mmol) and imidazole (0.61 g, 8.96 mmol) were dissolved in dichloromethane (15 ml), and the solution was stirred for 5 minutes. Then, iodine (2.28 g, 8.98 mmol) was added thereto, and the mixture was stirred for 10 minutes. A dichloromethane (4 ml) solution of N-tert-butoxycarbonyl-6-aminohexanol (1.3 g, 5.98 mmol) was added dropwise thereto, and the mixture was stirred at room temperature for 2 hours. After the reaction was confirmed by TLC to be complete, the reaction solution was filtered through celite, and a 5% aqueous sodium thiosulfate solution was added to the filtrate to remove iodine. The organic layer was washed twice with saturated saline and dehydrated over anhydrous sodium sulfate. The solvent was distilled off under reduced pressure, and then, the residue was purified using silica gel column chromatography (hexane:ethyl acetate=9:1) to obtain N-tert-butoxycarbonyl-6-amino-1-iodohexane (1.67 g, yield: 86%).

α-Methyl-1-methoxycarbonyl-3-indoleacetic acid methyl ester was synthesized according to a method described in Katayama M, Kato Y, Marumo S. "Synthesis, absolute configuration and biological activity of both enantiomers of 2-(5,6-dichloro-3-indolyl)propionic acid: new dichloroindole auxins" Bioscience, Biotechnology, and Biochemistry, 65 (2), 270-276; 2001.

α-(N-tert-Butoxycarbonyl-6-amino-1-hexyl)-α-methyl-1-methoxycarbonyl-3-indoleacetic Acid Methyl Ester

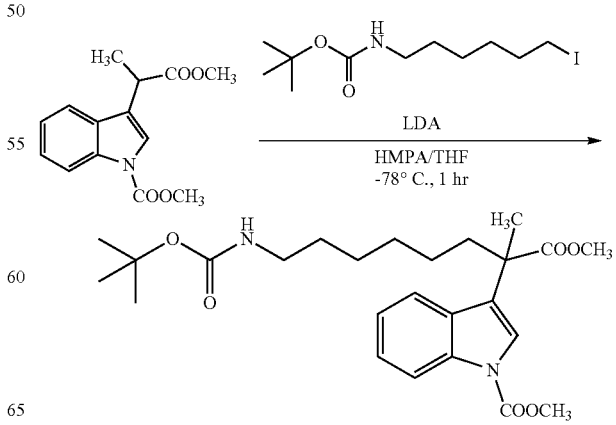

In a nitrogen atmosphere, α-methyl-1-methoxycarbonyl-3-indoleacetic acid methyl ester (83.8 mg, 0.321 mmol) was dissolved in tetrahydrofuran (2 ml), and the solution was cooled to −78° C. This solution was slowly added dropwise to a 1.0 M solution of lithium bistrimethylsilylamide (LHMDS) in tetrahydrofuran (0.69 ml, 1.5 eq), and the mixture was stirred at −78° C. for 0.5 hours. To this reaction solution, a tetrahydrofuran (1 ml) solution of N-tert-butoxycarbonyl-6-amino-1-iodohexane (105 mg, 0.321 mmol) was slowly added dropwise, and the mixture was stirred at −78° C. for 2 hours. After the reaction was confirmed by TLC to be complete, the temperature was adjusted to 0° C., and the reaction was terminated by the addition of water (5 ml), followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=8:2) to obtain α-(N-tert-butoxycarbonyl-6-amino-1-hexyl)-α-methyl-1-methoxycarbonyl-3-indoleacetic acid methyl ester (68.6 mg, yield: 46%): $^{1}$H NMR (400 MHz, CDCl$_3$): δ 8.19 (d, J=6.3 Hz, 1H), 7.52 (d, J=7.9 Hz, 1H), 7.48 (s, 1H), 7.32 (t, J=7.5 Hz, 1H), 7.21 (t, J=7.5 Hz, 1H), 4.54 (s, 1H), 4.03 (s, 3H), 3.62 (s, 3H), 3.06 (m, 2H), 2.04-2.12 (m, 2H), 1.61 (s, 3H), 1.17-1.43 (m, 17H); $^{13}$C NMR (100 MHz, CDCl$_3$): δ 176.3, 155.9, 151.3, 135.8, 128.6, 124.9, 124.5, 122.8, 122.0, 120.0, 115.2, 78.9, 53.7, 52.1, 45.5, 40.4, 37.2, 29.9, 29.5, 28.3, 26.5, 24.2, 22.5; FAB-MS: m/z 460 [M]$^{+}$.

α-(N-tert-Butoxycarbonyl-6-amino-1-hexyl)-α-methyl-3-indoleacetic Acid (Compound #13)

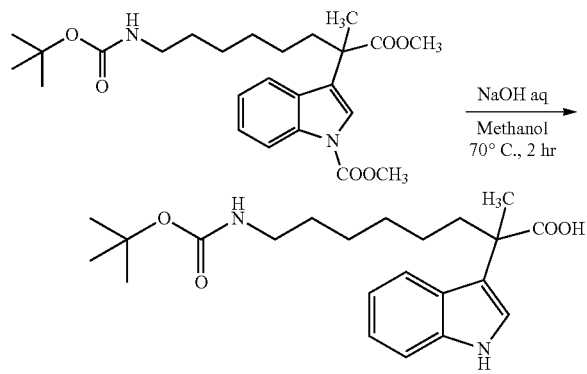

α-(N-tert-Butoxycarbonyl-6-amino-1-hexyl), α-methyl-1-methoxycarbonyl-3-indoleacetic acid methyl ester (60.0 mg, 0.130 mmol) was dissolved in methanol (4.6 ml). To the solution, water (0.4 ml) and potassium hydroxide (1.68 g, 30 mmol) were added, and the mixture was stirred at 70° C. for 2 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (benzene:acetone=85:15) to obtain α-(N-tert-butoxycarbonyl-6-amino-1-hexyl)-α-methyl-3-indoleacetic acid (compound #13) (40.0 mg, yield: 79%): $^{1}$H NMR (400 MHz, CDCl$_3$): δ 8.26 (s, 1H), 7.71 (d, J=8.0 Hz, 1H), 7.33 (d, J=8.0 Hz, 1H), 7.16 (t, J=7.4 Hz, 1H), 7.06 (t, J=7.3 Hz, 1H), 7.04 (s, 1H), 4.52 (s, 1H), 3.03 (m, 2H), 2.08-2.17 (m, 2H), 1.63 (s, 3H), 1.23-1.48 (m, 17H); $^{13}$C NMR (100 MHz, CDCl$_3$): δ 181.7, 156.1, 136.7, 125.5, 121.4, 120.4, 119.2, 118.8, 111.3, 79.1, 45.7, 40.5, 37.5, 29.7, 28.5, 26.5, 24.2, 22.6; IR (neat): 3415, 3339, 1699, 1519, 1460, 1369, 1249, 1170 cm$^{-1}$; FAB-MS: m/z 389 [M+H]$^{+}$.

Synthesis of Compound #14

2-(N-tert-Butoxycarbonyl-2-aminoethoxy)-ethanol

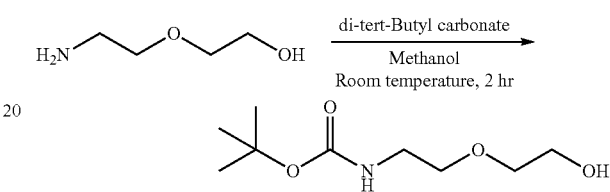

2-(2-Aminoethoxy)-ethanol (1.0 g, 9.511 mmol) was dissolved in methanol (10 ml). To this solution, di-tert-butyl carbonate (2.07 g, 9.485 mmol) was added, and the mixture was stirred at room temperature for 2 hours. After the reaction was confirmed by TLC to be complete, the solvent was distilled off under reduced pressure, and the residue was purified using silica gel column chromatography (hexane:acetone=3:2) to obtain 2-(N-tert-butoxycarbonyl-2-aminoethoxy)-ethanol (1.78 g, yield: 91%)

2-(N-tert-Butoxycarbonyl-2-aminoethoxy)-1-iodoethane

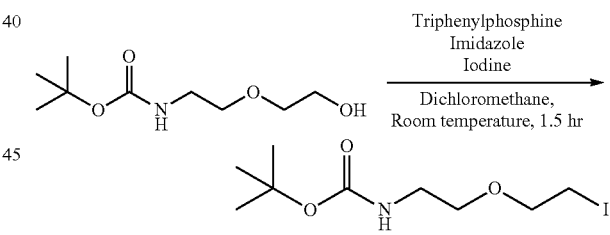

Triphenylphosphine (2.87 g, 10.94 mmol) and imidazole (0.75 g, 11.02 mmol) were dissolved in dichloromethane (15 ml), and the solution was stirred for 5 minutes. Then, iodine (2.78 g, 10.95 mmol) was added thereto, and the mixture was stirred for 10 minutes. A dichloromethane (4 ml) solution of 2-(N-tert-butoxycarbonyl-2-aminoethoxy)-ethanol (1.5 g, 7.308 mmol) was added dropwise thereto, and the mixture was stirred at room temperature for 1.5 hours. After the reaction was confirmed by TLC to be complete, the reaction solution was filtered through celite, and a 5% aqueous sodium thiosulfate solution was added to the filtrate to remove iodine. The organic layer was washed twice with saturated saline and dehydrated over anhydrous sodium sulfate. The solvent was distilled off under reduced pressure, and then, the residue was purified using silica gel column chromatography (hexane:ethyl acetate=85:15) to obtain 2-(N-tert-butoxycarbonyl-2-aminoethoxy)-1-iodoethane (2.19 g, yield: 95%).

α-[2-(N-tert-Butoxycarbonyl-2-aminoethoxy)-1-ethyl]-1-methoxycarbonyl-3-indoleacetic Acid Methyl Ester

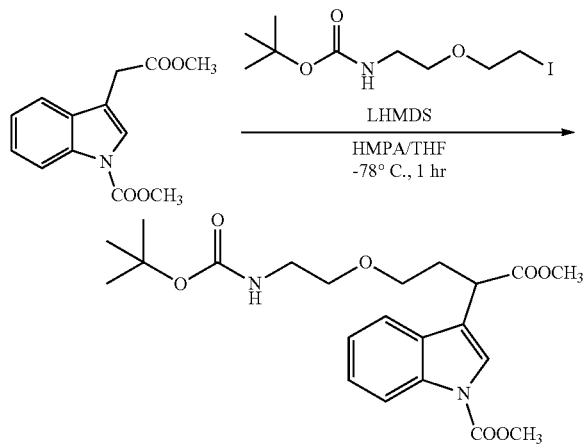

In a nitrogen atmosphere, 1-methoxycarbonyl-3-indoleacetic acid methyl ester (500 mg, 2.022 mmol) and hexamethylphosphoric triamide (HMPA, 1.81 g, 10.11 mmol) were dissolved in tetrahydrofuran (4 ml), and the solution was cooled to −78° C. A 1.5 M solution of lithium diisopropylamide (LDA) in cyclohexane (2.02 ml, 1.5 eq) was slowly added dropwise thereto, and the mixture was stirred at −78° C. for 0.5 hours. To this reaction solution, a tetrahydrofuran (2 ml) solution of 2-(N-tert-butoxycarbonyl-2-aminoethoxy)-1-iodoethane (637 mg, 2.022 mmol) was slowly added dropwise, and the mixture was stirred at −78° C. for 1 hour. After the reaction was confirmed by TLC to be complete, the temperature was adjusted to 0° C., and the reaction was terminated by the addition of water (15 ml), followed by extraction with ethyl acetate (15 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=8:2) to obtain α-[2-(N-tert-butoxycarbonyl-2-aminoethoxy)-1-ethyl]-1-methoxycarbonyl-3-indoleacetic acid methyl ester (645 mg, yield: 79%): $^1$H NMR (400 MHz, CDCl$_3$): δ 8.18 (d, J=7.0 Hz, 1H), 7.63 (d, J=7.7 Hz, 1H), 7.57 (s, 1H), 7.34 (t, J=7.7 Hz, 1H), 7.26 (t, J=7.3 Hz, 1H), 4.98 (s, 1H), 4.02-4.06 (m, 4H), 3.69 (s, 3H), 3.43-3.51 (m, 4H), 3.30 (m, 2H), 2.29 (m, 2H), 1.45 (s, 3H); $^{13}$C NMR (100 MHz, CDCl$_3$): δ 173.8, 155.9, 151.2, 135.4, 124.8, 123.1, 122.9, 119.2, 118.8, 115.2, 79.1, 69.8, 68.3, 52.7, 52.1, 40.3, 39.3, 32.2, 28.3; FAB-MS: m/z 435 [M+H]$^+$.

α-[2-(N-tert-Butoxycarbonyl-2-aminoethoxy)-1-ethyl]-3-indoleacetic Acid (Compound #14)

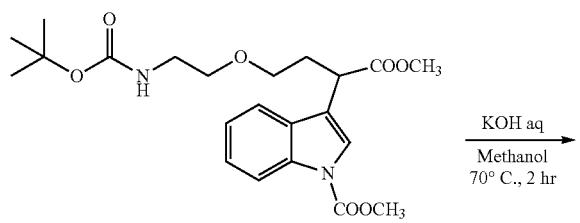

α-[2-(N-tert-Butoxycarbonyl-2-aminoethoxy)-1-ethyl]-1-methoxycarbonyl-3-indoleacetic acid methyl ester (80.0 mg, 0.184 mmol) was dissolved in methanol (2 ml). To this solution, a 2 N aqueous sodium hydroxide solution (0.5 ml) was added, and the mixture was stirred at 70° C. for 2 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=9:1) to obtain α-[2-(N-tert-butoxycarbonyl-2-aminoethoxy)-1-ethyl]-3-indoleacetic acid (compound #14) (70.2 mg, yield: 87%): $^1$H NMR (400 MHz, CDCl$_3$): δ 8.40 (s, 1H), 7.67 (d, J=7.9 Hz, 1H), 7.29 (d, J=8.0 Hz, 1H), 7.15 (t, J=7.8 Hz, 1H), 7.08 (t, J=7.3 Hz, 1H), 7.04 (s, 1H), 5.03 (s, 1H), 4.04 (t, J=7.1 Hz, 1H), 3.30-3.46 (m, 4H), 3.23 (m, 2H), 2.26 (m, 2H), 1.44 (s, 9H); $^{13}$C NMR (100 MHz, CDCl$_3$): δ 179.2, 156.2, 136.2, 126.4, 122.6, 122.1, 119.5, 119.1, 112.6, 111.3, 79.4, 69.7, 68.5, 40.3, 39.7, 32.3, 28.4; IR (neat): 3406, 3332, 1699, 1520, 1458, 1367, 1252, 1169, 1119 cm; FAB-MS: m/z 385 [M+Na]$^+$.

Synthesis of Compound #15

N-tert-Butoxycarbonyl-4-amino-1-butanol

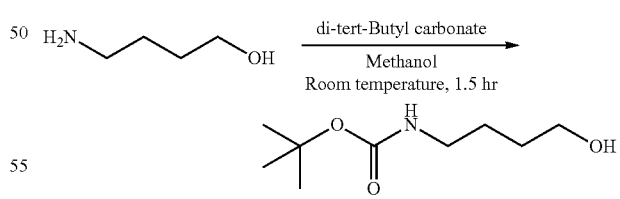

4-Amino-1-butanol (1.0 g, 11.22 mmol) was dissolved in methanol (10 ml). To this solution, di-tert-butyl carbonate (2.53 g, 11.58 mmol) was added, and the mixture was stirred at room temperature for 1.5 hours. After the reaction was confirmed by TLC to be complete, the solvent was distilled off under reduced pressure, and the residue was purified using silica gel column chromatography (hexane:acetone=9:1) to obtain N-tert-butoxycarbonyl-4-amino-1-butanol (1.88 g, yield: 89%).

N-tert-Butoxycarbonyl-4-amino-1-iodobutane

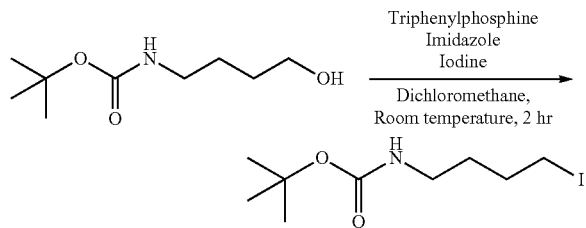

Triphenylphosphine (3.3 g, 12.58 mmol) and imidazole (0.86 g, 12.63 mmol) were dissolved in dichloromethane (15 ml), and the solution was stirred at 5 minutes. Then, iodine (3.2 g, 12.61 mmol) was added thereto, and the mixture was stirred for 10 minutes. A dichloromethane (4 ml) solution of N-tert-butoxycarbonyl-4-amino-1-butanol (1.6 g, 8.454 mmol) was added dropwise thereto, and the mixture was stirred at room temperature for 2 hours. After the reaction was confirmed by TLC to be complete, the reaction solution was filtered through celite, and a 5% aqueous sodium thiosulfate solution was added to the filtrate to remove iodine. The organic layer was washed twice with saturated saline and dehydrated over anhydrous sodium sulfate. The solvent was distilled off under reduced pressure, and then, the residue was purified using silica gel column chromatography (hexane:ethyl acetate=9:1) to obtain N-tert-butoxycarbonyl-4-amino-1-iodobutane (1.83 g, yield: 72%).

α-(N-tert-Butoxycarbonyl-4-amino-1-butyl)-1-methoxycarbonyl-3-indoleacetic Acid Methyl Ester

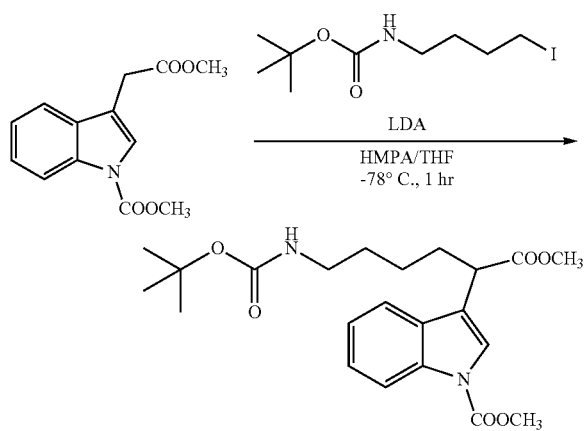

In a nitrogen atmosphere, 1-methoxycarbonyl-3-indoleacetic acid methyl ester (400 mg, 1.618 mmol) and hexamethylphosphoric triamide (HMPA, 1.45 g, 8.086 mmol) were dissolved in tetrahydrofuran (4 ml), and the solution was cooled to −78° C. A 1.5 M solution of lithium diisopropylamide (LDA) in cyclohexane (1.62 ml, 1.5 eq) was slowly added dropwise thereto, and the mixture was stirred at −78° C. for 0.5 hours. To this reaction solution, a tetrahydrofuran (2 ml) solution of N-tert-butoxycarbonyl-4-amino-1-iodobutane (484 mg, 1.618 mmol) was slowly added dropwise, and the mixture was stirred at −78° C. for 1 hour. After the reaction was confirmed by TLC to be complete, the temperature was adjusted to 0° C., and the reaction was terminated by the addition of water (15 ml), followed by extraction with ethyl acetate (15 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=8:2) to obtain α-(N-tert-butoxycarbonyl-4-amino-1-butyl)-1-methoxycarbonyl-3-indoleacetic acid methyl ester (373 mg, yield: 55%): $^1$H NMR (400 MHz, CDCl$_3$): δ 8.18 (d, J=7.8 Hz, 1H), 7.60 (d, J=7.8 Hz, 1H), 7.55 (s, 1H), 7.34 (t, J=7.9 Hz, 1H), 7.25 (t, J=7.7 Hz, 1H), 4.59 (s, 1H), 4.02 (s, 3H), 3.80 (t, J=7.6 Hz, 1H), 3.67 (s, 3H), 3.09 (m, 2H), 2.03 (m, 2H), 1.25-1.53 (m, 13H); $^{13}$C NMR (100 MHz, CDCl$_3$): δ 173.9, 155.9, 151.2, 135.5, 129.3, 124.8, 123.0, 122.9, 119.2, 115.2, 78.9, 53.6, 52.0, 42.5, 40.2, 31.7, 29.8, 28.3, 24.8; FAB-MS: m/z 419 [M+H]$^+$.

α-(N-tert-Butoxycarbonyl-4-amino-1-butyl)-3-indoleacetic Acid (Compound #15)

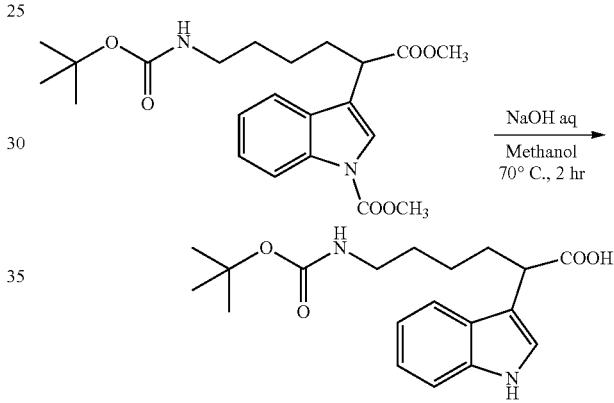

α-(N-tert-Butoxycarbonyl-4-amino-1-butyl)-1-methoxycarbonyl-3-indoleacetic acid methyl ester (100 mg, 0.239 mmol) was dissolved in methanol (2 ml). To this solution, a 2 N aqueous sodium hydroxide solution (0.5 ml) was added, and the mixture was stirred at 70° C. for 2 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=95:5) to obtain α-(N-tert-butoxycarbonyl-4-amino-1-butyl)-3-indoleacetic acid (compound #15) (71.8 mg, yield: 87%): $^1$H NMR (400 MHz, CDCl$_3$): δ 8.35 (s, 1H), 7.67 (d, J=7.8 Hz, 1H), 7.28 (d, J=7.8 Hz, 1H), 7.15 (t, J=7.7 Hz, 1H), 7.09 (t, J=7.3 Hz, 1H), 7.00 (s, 1H), 4.57 (s, 1H), 3.81 (t, J=7.5 Hz, 1H), 3.02 (m, 2H), 1.97 (m, 2H), 1.23-1.48 (m, 13H); $^{13}$C NMR (100 MHz, CDCl$_3$): δ 179.6, 156.1, 136.1, 126.4, 122.3, 122.0, 119.4, 119.1, 113.0, 111.3, 79.3, 42.9, 40.3, 31.9, 29.7, 28.4, 24.7; IR (neat): 3747, 1699, 1520, 1456, 1367, 1250, 1170 cm; FAB-MS: m/z 347 [M+H]$^+$.

Synthesis of Compound #17

2-Ethyl-1-iodobutane

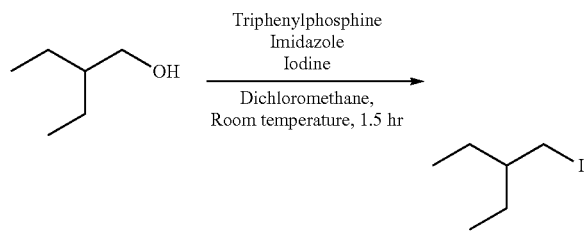

Triphenylphosphine (1.93 g, 7.358 mmol) and imidazole (0.5 g, 7.344 mmol) were dissolved in dichloromethane (5.0 ml), and the solution was stirred for 5 minutes. Then, iodine (1.86 g, 7.328 mmol) was added thereto, and the mixture was stirred for 10 minutes. A dichloromethane (2.0 ml) solution of 2-ethyl-1-butanol (0.5 g, 5.672 mmol) was added dropwise thereto, and the mixture was stirred at room temperature for 1.5 hours. After the reaction was confirmed by TLC to be complete, the reaction solution was filtered through celite, and a 5% aqueous sodium thiosulfate solution was added to the filtrate to remove iodine. The organic layer was washed twice with saturated saline and dehydrated over anhydrous sodium sulfate. The solvent was distilled off under reduced pressure, and then, the residue was purified using silica gel column chromatography (hexane) to obtain 2-ethyl-1-iodobutane (0.35 g, yield: 34%).

α-(2-Ethyl-1-butyl)-1-methoxycarbonyl-3-indoleacetic Acid Methyl Ester

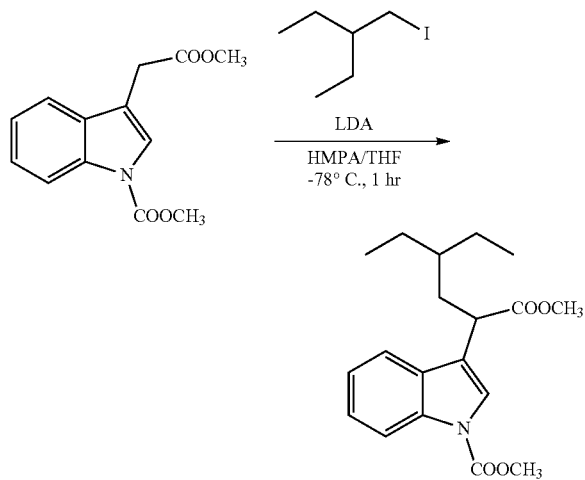

In a nitrogen atmosphere, 1-methoxycarbonyl-3-indoleacetic acid methyl ester (100 mg, 0.404 mmol) and hexamethylphosphoric triamide (HMPA, 362 mg, 2.020 mmol) were dissolved in tetrahydrofuran (2 ml), and the solution was cooled to −78° C. A 1.0 M solution of lithium bis(trimethylsilyl)amide (LHMDS) in tetrahydrofuran (0.61 ml, 1.5 eq) was slowly added dropwise thereto, and the mixture was stirred at −78° C. for 0.5 hours. To this reaction solution, a tetrahydrofuran (1 ml) solution of 2-ethyl-1-iodobutane (85.8 mg, 0.405 mmol) was slowly added dropwise, and the mixture was stirred at −78° C. for 1 hour. After the reaction was confirmed by TLC to be complete, the temperature was adjusted to 0° C., and the reaction was terminated by the addition of water (5 ml), followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=9:1) to obtain α-(2-ethyl-1-butyl)-1-methoxycarbonyl-3-indoleacetic acid methyl ester (104 mg, yield: 78%): $^1$H NMR (400 MHz, CDCl$_3$): δ 8.18 (d, J=7.0 Hz, 1H), 7.64 (d, J=7.8 Hz, 1H), 7.57 (s, 1H), 7.34 (t, J=7.7 Hz, 1H), 7.26 (t, J=7.4 Hz, 1H), 4.01 (s, 3H), 3.93 (t, J=7.8 Hz, 1H), 3.67 (s, 3H), 1.96 (m, 2H), 1.21-1.41 (m, 5H), 0.82-0.88 (m, 6H); $^{13}$C NMR (100 MHz, CDCl$_3$): δ 174.3, 151.3, 135.5, 129.5, 124.7, 122.9, 119.7, 119.3, 115.2, 53.7, 52.0, 40.4, 38.0, 35.6, 25.1, 24.9, 10.4, 10.4; IR (neat): 1738, 1455, 1377, 1256, 1164, 1085 cm$^{-1}$; EI-MS: m/z 331 [M]$^+$.

α-(2-Ethyl-1-butyl)-3-indoleacetic Acid (Compound #17)

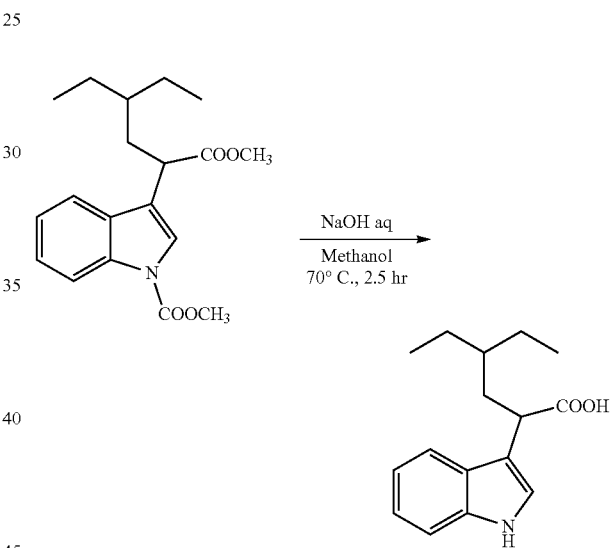

α-(2-Ethyl-1-butyl)-1-methoxycarbonyl-3-indoleacetic acid (70.0 mg, 0.211 mmol) was dissolved in methanol (2 ml). To this solution, a 2 N aqueous sodium hydroxide solution (0.5 ml) was added, and the mixture was stirred at 70° C. for 2.5 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=95:5) to obtain α-(2-ethyl-1-butyl)-3-indoleacetic acid (compound #17) (52.4 mg, yield: 96): $^1$H NMR (400 MHz, CDCl$_3$): δ 8.02 (s, 1H), 7.70 (d, J=7.9 Hz, 1H), 7.30 (d, J=8.0 Hz, 1H), 7.17 (t, J=7.9 Hz, 1H), 7.11 (t, J=7.5 Hz, 1H), 7.08 (s, 1H), 3.97 (t, J=7.8 Hz, 1H), 1.96 (m, 2H), 1.23-1.39 (m, 5H), 0.78-0.84 (m, 6H); $^{13}$C NMR (100 MHz, CDCl$_3$): δ 181.1, 136.1, 126.6, 122.2, 122.2, 119.7, 119.3, 113.7, 111.2, 40.6, 37.8, 35.9, 25.0, 25.0, 10.4, 10.4; IR (neat): 3414, 1703, 1458, 1293, 1098 cm$^{-1}$; FAB-MS: m/z 260 [M+H]$^+$.

Synthesis of Compound #18

3-Methyl-1-iodopentane

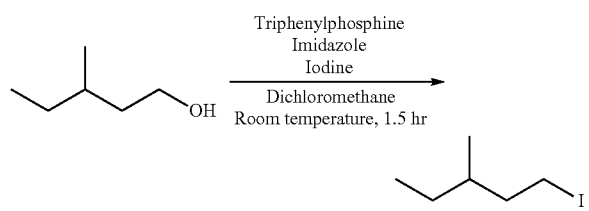

Triphenylphosphine (1.93 g, 7.358 mmol) and imidazole (0.5 g, 7.344 mmol) were dissolved in dichloromethane (5.0 ml), and the solution was stirred for 5 minutes. Then, iodine (1.86 g, 7.328 mmol) was added thereto, and the mixture was stirred for 10 minutes. A dichloromethane (2.0 ml) solution of 3-methyl-1-pentanol (0.5 g, 5.672 mmol) was added dropwise thereto, and the mixture was stirred at room temperature for 1.5 hours. After the reaction was confirmed by TLC to be complete, the reaction solution was filtered through celite, and a 5% aqueous sodium thiosulfate solution was added to the filtrate to remove iodine. The organic layer was washed twice with saturated saline and dehydrated over anhydrous sodium sulfate. The solvent was distilled off under reduced pressure, and then, the residue was purified using silica gel column chromatography (hexane:ethyl acetate=98:2) to obtain 3-methyl-1-iodopentane (0.12 mg, yield: 11%).

α-(3-Methyl-1-pentyl)-1-methoxycarbonyl-3-indoleacetic Acid Methyl Ester

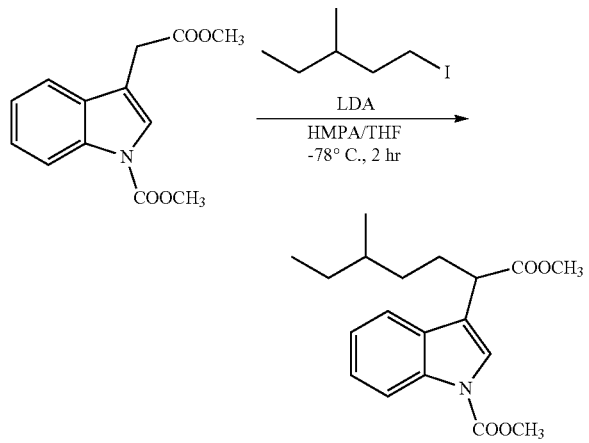

In a nitrogen atmosphere, 1-methoxycarbonyl-3-indoleacetic acid methyl ester (50.0 mg, 0.202 mmol) and hexamethylphosphoric triamide (HMPA, 181 mg, 1.011 mmol) were dissolved in tetrahydrofuran (1 ml), and the solution was cooled to −78° C. A 1.0 M solution of lithium bis(trimethylsilyl)amide (LHMDS) in tetrahydrofuran (0.30 ml, 1.5 eq) was slowly added dropwise thereto, and the mixture was stirred at −78° C. for 0.5 hours. To this reaction solution, a tetrahydrofuran (1 ml) solution of 3-methyl-1-iodopentane (51.5 mg, 0.243 mmol) was slowly added dropwise, and the mixture was stirred at −78° C. for 2 hours. After the reaction was confirmed by TLC to be complete, the temperature was adjusted to 0° C., and the reaction was terminated by the addition of water (5 ml), followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=12:1) to obtain α-(3-methyl-1-pentyl)-1-methoxycarbonyl-3-indoleacetic acid methyl ester (25.8 mg, yield: 39%) $^1$H NMR (400 MHz, CDCl$_3$): δ 8.18 (d, J=6.7 Hz, 1H), 7.62 (d, J=7.7 Hz, 1H), 7.56 (s, 1H), 7.34 (t, J=7.8 Hz, 1H), 7.26 (t, J=7.2 Hz, 1H), 4.03 (s, 3H), 3.77 (t, J=7.9 Hz, 1H), 3.68 (s, 3H), 2.01 (m, 2H), 1.10-1.39 (m, 5H), 0.82-0.87 (m, 6H); $^{13}$C NMR (100 MHz, CDCl$_3$): δ 174.2, 151.3, 135.5, 129.5, 124.8, 122.9, 119.4, 119.3, 115.2, 53.7, 52.0, 42.9, 34.4, 34.2, 29.8, 29.2, 19.1, 11.3; IR (neat): 1741, 1454, 1378, 1254, 1084 cm$^{-1}$; EI-MS: m/z 331 [M]$^+$.

α-(3-Methyl-1-pentyl)-3-indoleacetic Acid (Compound #18)

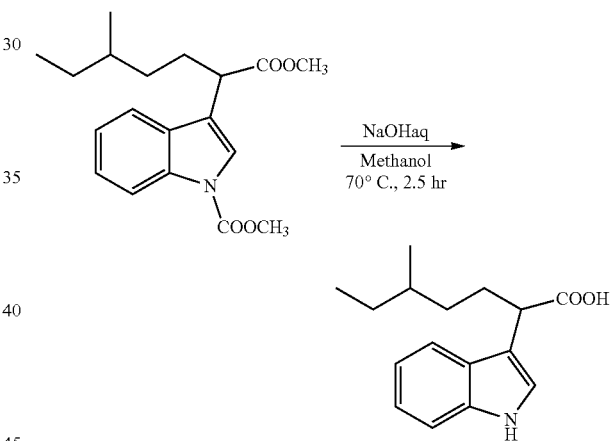

α-(3-Methyl-1-pentyl)-1-methoxycarbonyl-3-indoleacetic acid methyl ester (20.0 mg, 0.060 mmol) was dissolved in methanol (1 ml). To this solution, a 2 N aqueous sodium hydroxide solution (0.25 ml) was added, and the mixture was stirred at 70° C. for 2.5 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=95:5) to obtain α-(3-methyl-1-pentyl)-3-indoleacetic acid (compound #18) (16.8 mg, yield: 89%): $^1$H NMR (400 MHz, CDCl$_3$): δ 8.07 (s, 1H), 7.70 (d, J=7.8 Hz, 1H), 7.33 (d, J=8.1 Hz, 1H), 7.19 (t, J=8.0 Hz, 1H), 7.10-7.13 (m, 2H), 3.82 (t, J=6.7 Hz, 1H), 1.97 (m, 2H), 1.10-1.36 (m, 5H), 0.79-0.85 (m, 6H); $^{13}$C NMR (100 MHz, CDCl$_3$): δ 180.4, 136.1, 126.6, 122.2, 122.2, 119.7, 119.3, 113.7, 111.2, 43.2, 34.5, 34.3, 30.1, 29.2, 19.1, 11.3; IR (neat): 3418, 1704, 1456, 1294, 1098 cm$^{-1}$; EI-MS: m/z 259 [M]$^+$.

Synthesis of Compound #19

2-Methyl-1-iodopentane

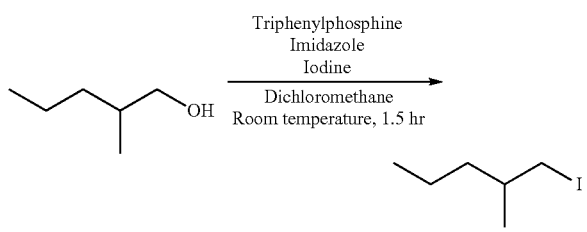

Triphenylphosphine (1.93 g, 7.358 mmol) and imidazole (0.5 g, 7.344 mmol) were dissolved in dichloromethane (5.0 ml), and the solution was stirred for 5 minutes. Then, iodine (1.86 g, 7.328 mmol) was added thereto, and the mixture was stirred for 10 minutes. A dichloromethane (2.0 ml) solution of 2-methyl-1-pentanol (0.5 g, 5.672 mmol) was added dropwise thereto, and the mixture was stirred at room temperature for 1.5 hours. After the reaction was confirmed by TLC to be complete, the reaction solution was filtered through celite, and a 5% aqueous sodium thiosulfate solution was added to the filtrate to remove iodine. The organic layer was washed twice with saturated saline and dehydrated over anhydrous sodium sulfate. The solvent was distilled off under reduced pressure, and then, the residue was purified using silica gel column chromatography (hexane) to obtain 2-methyl-1-iodopentane (0.56 g, yield: 54%).

α-(2-Methyl-1-pentyl)-1-methoxycarbonyl-3-indoleacetic Acid Methyl Ester

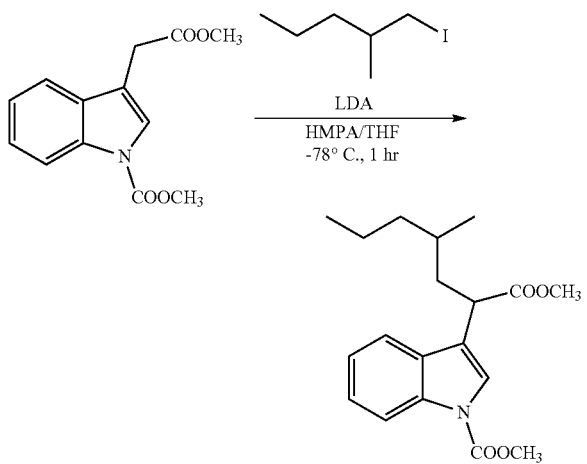

In a nitrogen atmosphere, 1-methoxycarbonyl-3-indoleacetic acid methyl ester (100 mg, 0.404 mmol) and hexamethylphosphoric triamide (HMPA, 362 mg, 2.020 mmol) were dissolved in tetrahydrofuran (2 ml), and the solution was cooled to −78° C. A 1.0 M solution of lithium bis(trimethylsilyl)amide (LHMDS) in tetrahydrofuran (0.61 ml, 1.5 eq) was slowly added dropwise thereto, and the mixture was stirred at −78° C. for 0.5 hours. To this reaction solution, a tetrahydrofuran (1 ml) solution of 2-methyl-1-iodopentane (85.8 mg, 0.405 mmol) was slowly added dropwise, and the mixture was stirred at −78° C. for 1 hour. After the reaction was confirmed by TLC to be complete, the temperature was adjusted to 0° C., and the reaction was terminated by the addition of water (5 ml), followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=9:1) to obtain α-(2-methyl-1-pentyl)-1-methoxycarbonyl-3-indoleacetic acid methyl ester (101 mg, yield: 75%): $^1$H NMR (400 MHz, CDCl$_3$): δ 8.18 (d, J=5.7 Hz, 1H), 7.63 (d, J=7.8 Hz, 1H), 7.55 (s, 1H), 7.34 (t, J=7.6 Hz, 1H), 7.27 (t, J=7.5 Hz, 1H), 4.03 (s, 3H), 3.91-3.97 (m, 1H), 3.68 (s, 3H), 1.58-2.24 (m, 2H), 1.10-1.50 (m, 5H), 0.83-0.97 (m, 6H); $^{13}$C NMR (100 MHz, CDCl$_3$): δ 174.4, 151.2, 135.4, 129.4, 124.7, 122.9, 122.8, 119.9, 119.4, 115.2, 53.7, 52.0, 40.4, 39.6, 39.3, 30.7, 19.8, 19.4, 14.2; IR (neat): 1739, 1456, 1373, 1217, 1087 cm$^{-1}$; EI-MS: m/z 331 [M]$^+$.

α-(2-Methyl-1-pentyl)-3-indoleacetic Acid (Compound #19)

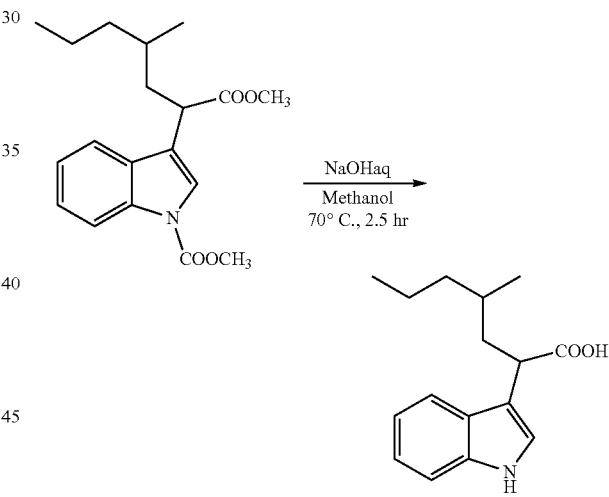

α-(2-Methyl-1-pentyl)-1-methoxycarbonyl-3-indoleacetic acid methyl ester (70.0 mg, 0.211 mmol) was dissolved in methanol (2 ml). To this solution, a 2 N aqueous sodium hydroxide solution (0.5 ml) was added, and the mixture was stirred at 70° C. for 2.5 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=95:5) to obtain α-(2-methyl-1-pentyl)-3-indoleacetic acid (compound #19) (51.9 mg, yield: 95%): $^1$H NMR (400 MHz, CDCl$_3$): δ 8.12 (s, 1H), 7.70 (d, J=7.8 Hz, 1H), 7.30 (d, J=8.0 Hz, 1H), 7.17 (t, J=7.4 Hz, 1H), 7.11 (t, J=7.2 Hz, 1H), 7.06 (s, 1H), 3.96-4.02 (m, 1H), 1.60-2.22 (m, 2H), 1.12-1.51 (m, 5H), 0.79-0.94 (m, 6H); $^{13}$C NMR (100 MHz, CDCl$_3$): δ 180.9, 136.1, 126.5, 122.3, 122.2, 119.7, 119.3, 113.3, 111.2, 40.7, 39.9, 39.2, 30.3, 19.8, 19.4, 14.3; IR (neat): 3417, 1699, 1457, 1292, 1099 cm$^{-1}$; EI-MS: m/z 259 [M]$^+$.

Synthesis of Compound #20

4-Phenyl-2-(1H-indol-3-yl)-4-oxo-butanoic Acid (Compound #20)

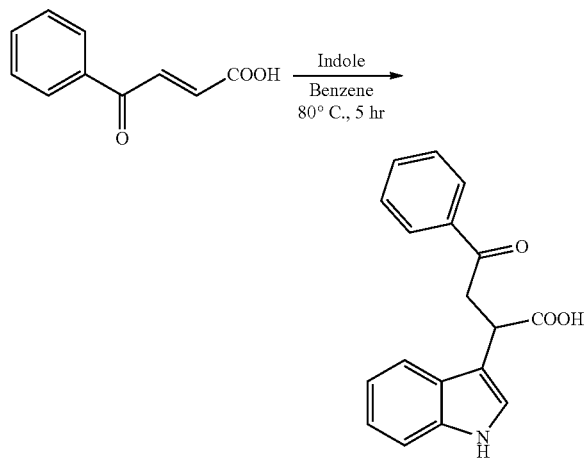

In a 30-mL round-bottomed flask, trans-4-phenyl-4-oxo-2-butenoic acid (1.0 g, 5.65 mmol) was dissolved in benzene (25 mL). To the solution, indole (0.79 g, 6.77 mmol) was added, and the mixture was stirred at 80° C. for 5 hours and stirred until the temperature became room temperature. The solvent in the reaction solution was distilled off under reduced pressure, and the residue was recrystallized from benzene to obtain 4-phenyl-2-(1H-indol-3-yl)-4-oxo-butanoic acid (compound #20) (1.24 g, yield: 75%); Melting point: 149 to 150° C.; $^1$H NMR (400 MHz, acetone-d$_6$): δ 10.17 (1H, brs, 1H), 8.05 (2H, d, J=8.2 Hz), 7.80 (1H, d, J=8.3 Hz), 7.57 (1H, t, J=7.8 Hz), 7.51 (2H, dd, J=8.2, 7.8 Hz), 7.41 (1H, d, J=8.2 Hz), 7.37 (1H, s), 7.13 (1H, t, J=8.2 Hz), 7.06 (1H, t, J=8.2 Hz), 4.57 (1H, dd, J=11.0, 4.1 Hz), 4.13 (1H, dd, J=17.8, 11.0 Hz), 3.41 (1H, dd, J=17.8, 4.1 Hz); IR: (neat): 3400, 3055, 1711, 1677, 1453 cm$^{-1}$; HRFAB-MS found m/z 294.1143 [M+H]$^+$, calcd for 294.1130 (C$_{18}$H$_{16}$NO$_3$).

Synthesis of Compound #21

4,4,5,5,5-Pentafluoro-1-iodopentane

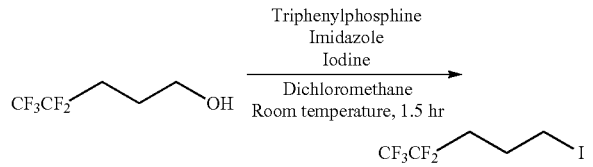

Triphenylphosphine (1.1 g, 4.211 mmol) and imidazole (0.29 g, 4.211 mmol) were dissolved in dichloromethane (5.0 ml), and the solution was stirred for 5 minutes. Then, iodine (1.07 g, 4.211 mmol) was added thereto, and the mixture was stirred for 10 minutes. A dichloromethane (2.0 ml) solution of 4,4,5,5,5-pentafluoro-1-pentanol (0.5 g, 2.807 mmol) was added dropwise thereto, and the mixture was stirred at room temperature for 1.5 hours. After the reaction was confirmed by TLC to be complete, the reaction solution was filtered through celite, and a 5% aqueous sodium thiosulfate solution was added to the filtrate to remove iodine. The organic layer was washed twice with saturated saline and dehydrated over anhydrous sodium sulfate. The solvent was distilled off under reduced pressure, and then, the residue was purified using silica gel column chromatography (hexane) to obtain 4,4,5,5,5-pentafluoro-1-iodopentane (0.36 g, yield: 45%).

α-(4,4,5,5,5-Pentafluoro-1-pentyl)-1-methoxycarbonyl-3-indoleacetic Acid Methyl Ester

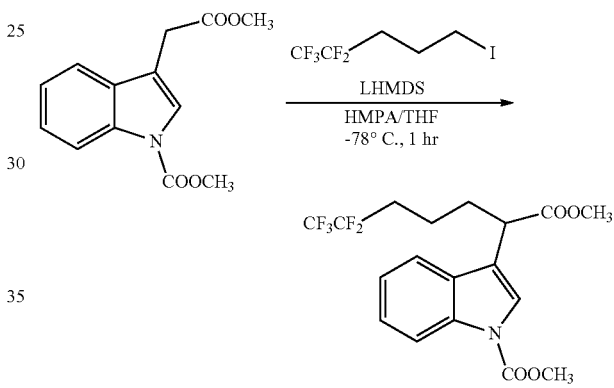

In a nitrogen atmosphere, 1-methoxycarbonyl-3-indoleacetic acid methyl ester (50.0 mg, 0.202 mmol) and hexamethylphosphoric triamide (HMPA, 181 mg, 1.011 mmol) were dissolved in tetrahydrofuran (1 ml), and the solution was cooled to −78° C. A 1.0 M solution of lithium bis(trimethylsilyl)amide (LHMDS) in tetrahydrofuran (0.30 ml, 1.5 eq) was slowly added dropwise thereto, and the mixture was stirred at −78° C. for 0.5 hours. To this reaction solution, a tetrahydrofuran (1 ml) solution of 4,4,5,5,5-pentafluoro-1-iodopentane (81.4 mg, 0.283 mmol) was slowly added dropwise, and the mixture was stirred at −78° C. for 1 hour. After the reaction was confirmed by TLC to be complete, the temperature was adjusted to 0° C., and the reaction was terminated by the addition of water (5 ml), followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=85:15) to obtain α-(4,4,5,5,5-pentafluoro-1-pentyl)-1-methoxycarbonyl-3-indoleacetic acid methyl ester (59.8 mg, yield: 73%): $^1$H NMR (400 MHz, CDCl$_3$): δ 8.19 (d, J=7.6 Hz, 1H), 7.60 (d, J=7.8 Hz, 1H), 7.57 (s, 1H), 7.36 (t, J=7.5 Hz, 1H), 7.27 (t, J=6.9 Hz, 1H), 4.03 (s, 3H), 3.83 (t, J=7.6 Hz, 1H), 3.69 (s, 3H), 1.98-2.23 (m, 4H), 1.62-1.68 (m, 2H); $^{13}$C NMR (100 MHz, CDCl$_3$) δ 173.5, 151.3, 135.5, 129.1, 125.0, 123.1, 123.1, 119.2, 118.6, 115.3, 53.8, 52.2, 42.3, 31.4, 30.6, 30.3, 30.1, 18.6; IR (neat) 1739, 1456, 1378, 1257, 1198 cm$^{-1}$; EI-MS: m/z 407 [M]$^+$.

α-(4,4,5,5,5-Pentafluoro-1-pentyl)-3-indoleacetic Acid (Compound #21)

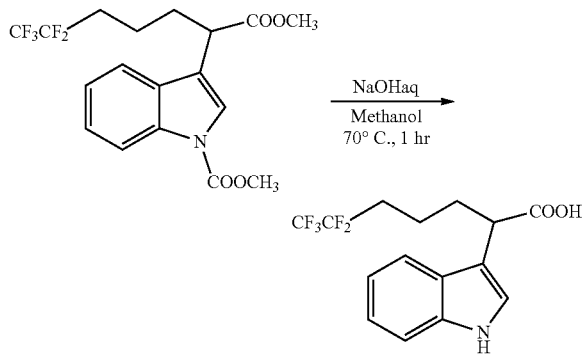

α-(4,4,5,5,5-Pentafluoro-1-pentyl)-1-methoxycarbonyl-3-indoleacetic acid methyl ester (55.5 mg, 0.183 mmol) was dissolved in methanol (1 ml). To this solution, a 2 N aqueous sodium hydroxide solution (0.25 ml) was added, and the mixture was stirred at 70° C. for 1 hour. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=95:5) to obtain α-(4,4,5,5,5-pentafluoro-1-pentyl)-3-indoleacetic acid (compound #21) (43.9 mg, yield: 97%): $^1$H NMR (400 MHz, CDCl$_3$): δ 8.06 (s, 1H), 7.67 (d, J=7.9 Hz, 1H), 7.33 (d, J=8.1 Hz, 1H), 7.20 (t, J=8.0 Hz, 1H), 7.12 (t, J=7.9 Hz, 1H), 7.09 (s, 1H), 3.87 (t, J=7.5 Hz, 1H), 1.95-2.22 (m, 4H), 1.60-1.67 (m, 2H); $^{13}$C NMR (100 MHz, CDCl$_3$): δ 179.9, 136.2, 126.2, 122.4, 122.4, 119.9, 119.1, 112.5, 111.4, 42.7, 31.5, 30.6, 30.3, 30.1, 18.6; IR (neat): 3418, 1704, 1459, 1198 cm; EI-MS: m/z 335 [M]$^+$.

Synthesis of Compound #22

3-(2-Hydroxy-1-ethyl)-1,1'-biphenyl

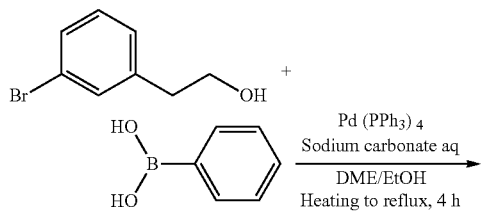

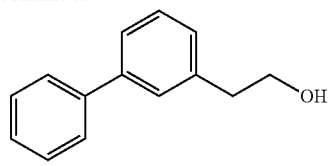

2-(3-Bromophenyl)-1-ethanol (200 mg, 0.995 mmol) was dissolved in a mixed solvent of dimethoxyethane:ethanol (=5:1) (3.0 ml). To the solution, phenylboronic acid (242 mg, 1.985 mmol), a 2 M aqueous sodium carbonate solution (1.5 ml), and tetrakis(triphenylphosphine) palladium(0) (Pd (PPh$_3$)$_4$, 56.0 mg, 0.048 mmol) were added, and the mixture was stirred for 4 hours under heating to reflux. After the reaction was confirmed by TLC to be complete, the reaction solution was filtered through celite, and the filtrate was neutralized by the addition of hydrochloric acid, followed by extraction with ethyl acetate (10 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=8:2) to obtain 3-(2-hydroxy-1-ethyl)-1,1'-biphenyl (172 mg, yield: 87%).

3-(2-Iodo-1-ethyl)-1,1'-biphenyl

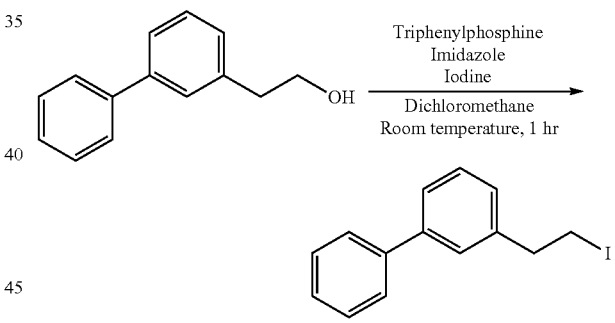

Triphenylphosphine (327 mg, 1.248 mmol) and imidazole (85.0 mg, 1.249 mmol) were dissolved in dichloromethane (3.0 ml), and the solution was stirred for 5 minutes. Then, iodine (317 mg, 1.248 mmol) was added thereto, and the mixture was stirred for 10 minutes. A dichloromethane (0.5 ml) solution of 3-(2-hydroxy-1-ethyl)-1,1'-biphenyl (165 mg, 0.832 mmol) was added dropwise thereto, and the mixture was stirred at room temperature for 1 hour. After the reaction was confirmed by TLC to be complete, the reaction solution was filtered through celite, and a 5% aqueous sodium thiosulfate solution was added to the filtrate to remove iodine. The organic layer was washed twice with saturated saline and dehydrated over anhydrous sodium sulfate. The solvent was distilled off under reduced pressure, and then, the residue was purified using silica gel column chromatography (hexane:ethyl acetate=98:2) to obtain 3-(2-iodo-1-ethyl)-1,1'-biphenyl (185 mg, yield: 72%).

71

α-[2-(1,1'-Biphenyl-3-yl)-1-ethyl]-1-methoxycarbonyl-3-indoleacetic Acid Methyl Ester

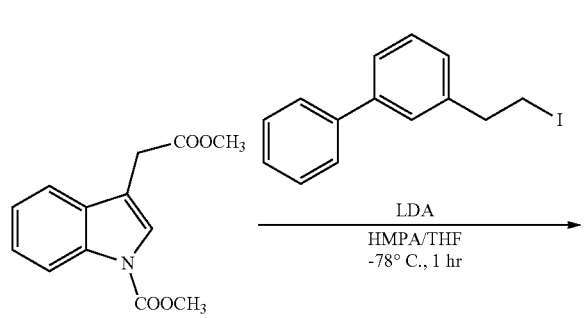

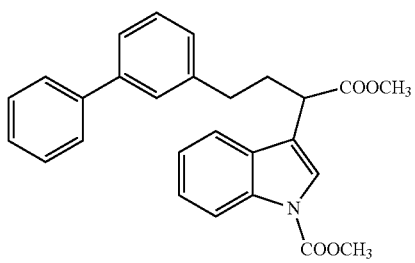

In a nitrogen atmosphere, 1-methoxycarbonyl-3-indoleacetic acid methyl ester (80 mg, 0.324 mmol) and hexamethylphosphoric triamide (HMPA, 290 mg, 1.618 mmol) were dissolved in tetrahydrofuran (2 ml), and the solution was cooled to −78° C. A 1.5 M solution of lithium diisopropylamide (LDA) in cyclohexane (0.32 ml, 1.5 eq) was slowly added dropwise thereto, and the mixture was stirred at −78° C. for 0.5 hours. To this reaction solution, a tetrahydrofuran (1 ml) solution of 3-(2-iodo-1-ethyl)-1,1'-biphenyl (99.7 mg, 0.324 mmol) was slowly added dropwise, and the mixture was stirred at −78° C. for 1 hour. After the reaction was confirmed by TLC to be complete, the temperature was adjusted to 0° C., and the reaction was terminated by the addition of water (5 ml), followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=85:15) to obtain α-[2-(1,1'-biphenyl-3-yl)-1-ethyl]-1-methoxycarbonyl-3-indoleacetic acid methyl ester (132 mg, yield: 96%): $^1$H NMR (400 MHz, CDCl$_3$): δ 8.19 (d, J=6.8 Hz, 1H), 7.55-7.58 (m, 4H), 7.31-7.44 (m, 7H), 7.24 (t, J=8.1 Hz, 1H), 7.15 (d, J=7.5 Hz, 1H), 4.02 (s, 3H), 3.86 (t, J=7.5 Hz, 1H), 3.65 (S, 3H), 2.73 (t, J=7.7 Hz, 2H), 2.25-2.58 (m, 2H); $^{13}$C NMR (100 MHz, CDCl$_3$): δ 173.8, 151.2, 141.4, 141.3, 141.1, 135.5, 129.3, 128.8, 128.6, 127.3, 127.2, 127.1, 124.9, 124.8, 123.1, 122.9, 119.3, 118.9, 115.2, 53.7, 52.1, 41.8, 33.7, 33.5; EI-MS: m/z 427 [M]$^+$.

72

α-[2-(1,1'-Biphenyl-3-yl)-1-ethyl]-3-indoleacetic Acid (Compound #22)

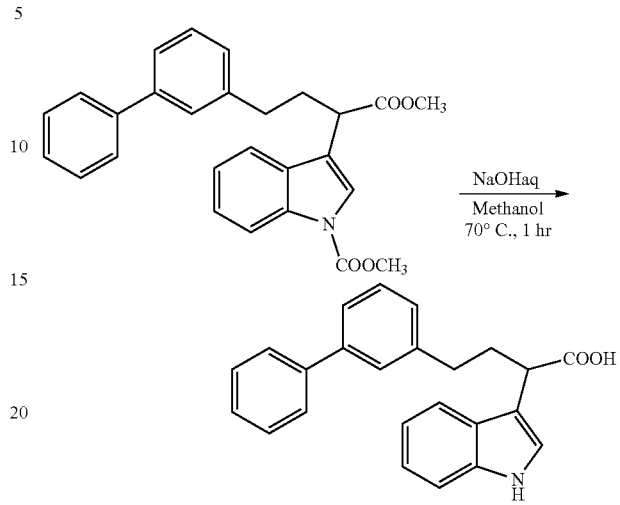

α-[2-(1,1'-Biphenyl-3-yl)-1-ethyl]-1-methoxycarbonyl-3-indoleacetic acid methyl ester (80.0 mg, 0.187 mmol) was dissolved in methanol (2 ml). To this solution, a 2 N aqueous sodium hydroxide solution (0.5 ml) was added, and the mixture was stirred at 70° C. for 1.5 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=95:5) to obtain α-[2-(1,1'-biphenyl-3-yl)-1-ethyl]-3-indoleacetic acid (compound #22) (60.3 mg, yield: 91%): $^1$H NMR (400 MHz, CDCl$_3$): δ 8.01 (s, 1H), 7.65 (d, J=7.9 Hz, 1H), 7.53-7.55 (m, 2H), 7.29-7.41 (m, 7H), 7.17 (t, J=7.2 Hz, 1H), 7.07-7.13 (m, 3H), 3.91 (t, J=7.5 Hz, 1H), 2.71 (t, J=7.7 Hz, 2H), 2.39 (m, 2H); $^{13}$C NMR (100 MHz, CDCl$_3$): δ 180.3, 141.8, 141.3, 141.2, 136.1, 128.8, 128.7, 127.4, 127.4, 127.2, 126.4, 124.9, 122.4, 122.3, 119.8, 119.3, 112.9, 111.3, 42.2, 33.8, 33.7; IR (neat): 3420, 1699, 1456, 1216, 1097 cm$^{-1}$; EI-MS: m/z 355 [M]$^+$.

Synthesis of compound #23

α-(2-Phenyl-1-ethyl)-1-methoxycarbonyl-3-indoleacetic Acid Methyl Ester

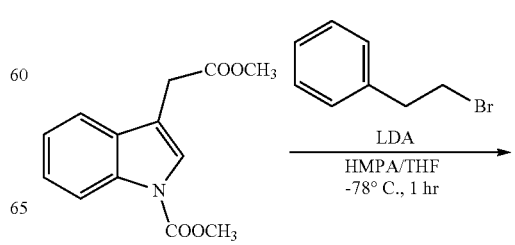

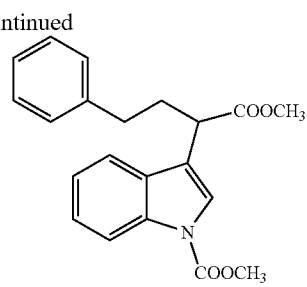

In a nitrogen atmosphere, 1-methoxycarbonyl-3-indoleacetic acid methyl ester (300 mg, 1.213 mmol) and hexamethylphosphoric triamide (HMPA, 1.09 g, 6.067 mmol) were dissolved in tetrahydrofuran (2 ml), and the solution was cooled to −78° C. A 1.5 M solution of lithium diisopropylamide (LDA) in cyclohexane (1.21 ml, 1.5 eq) was slowly added dropwise thereto, and the mixture was stirred at −78° C. for 0.5 hours. To this reaction solution, a tetrahydrofuran (2 ml) solution of 1-bromo-2-phenylethane (292 mg, 1.577 mmol) was slowly added dropwise, and the mixture was stirred at −78° C. for 1 hour. After the reaction was confirmed by TLC to be complete, the temperature was adjusted to 0° C., and the reaction was terminated by the addition of water (10 ml), followed by extraction with ethyl acetate (10 ml) three times. The organic layer was washed twice with saturated saline and dehydrated over anhydrous sodium sulfate. The solvent was distilled off under reduced pressure, and then, the residue was purified using silica gel column chromatography (benzene) to obtain α-(2-phenyl-1-ethyl)-1-methoxycarbonyl-3-indoleacetic acid methyl ester (228 mg, yield: 54%): $^1$H NMR (400 MHz, CDCl$_3$): δ 8.18 (d, J=6.0 Hz, 1H), 7.57 (s, 1H), 7.55 (d, J=8.0 Hz, 1H), 7.31 (t, J=7.8 Hz, 1H), 7.13-7.26 (m, 6H), 3.94 (s, 3H), 3.83 (t, J=7.5 Hz, 1H), 3.64 (s, 3H), 2.66 (t, J=7.8 Hz, 2H), 2.35 (m, 2H); $^{13}$C NMR (100 MHz, CDCl$_3$): δ 173.8, 151.2, 140.9, 135.4, 129.3, 128.4, 128.3, 126.0, 124.8, 123.1, 122.9, 119.3, 119.0, 115.2, 53.7, 52.0, 41.8, 33.5; EI-MS: m/z 351 [M]$^+$.

α-(2-Phenyl-1-ethyl)-3-indoleacetic Acid (Compound #23)

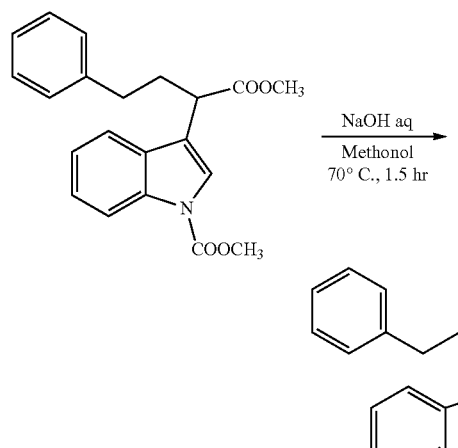

α-(2-Phenyl-1-ethyl)-1-methoxycarbonyl-3-indoleacetic acid methyl ester (150 mg, 0.427 mmol) was dissolved in methanol (2 ml). To this solution, a 2 N aqueous sodium hydroxide solution (0.5 ml) was added, and the mixture was stirred at 70° C. for 1.5 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=95:5) to obtain α-(2-phenyl-1-ethyl)-3-indoleacetic acid (compound #23) (85.3 mg, yield: 72%): $^1$H NMR (400 MHz, acetone-d$_6$): δ 10.16 (s, 1H), 7.67 (d, J=8.0 Hz, 1H), 7.40 (d, J=8.1 Hz, 1H), 7.09-7.32 (m, 7H), 7.03 (t, J=7.6 Hz, 1H), 3.93 (t, J=7.4 Hz, 1H), 2.67 (t, J=5.4 Hz, 2H), 2.35 (m, 2H); $^{13}$C NMR (100 MHz, acetone-d$_6$): δ 175.4, 142.4, 137.2, 128.8, 128.7, 127.2, 126.2, 123.2, 121.8, 119.4, 119.2, 113.6, 111.8, 42.5, 34.9, 34.1; IR (neat): 3416, 1700, 1457, 1246, 1098 cm$^{-1}$;
FAB-MS: m/z 280 [M+H]$^+$.

Synthesis of Compound #24

2-Cyclopentyl-1-iodoethane

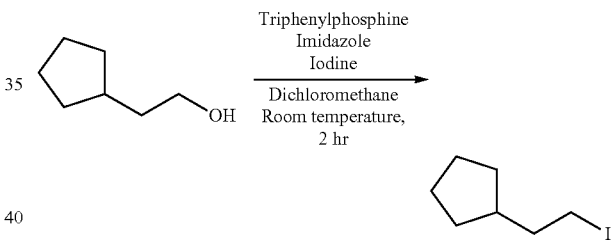

Triphenylphosphine (1.03 g, 3.942 mmol) and imidazole (0.27 g, 3.937 mmol) were dissolved in dichloromethane (5 ml), and the solution was stirred for 5 minutes. Then, iodine (1.0 g, 3.940 mmol) was added thereto, and the mixture was stirred for 10 minutes. A dichloromethane (1 ml) solution of 2-cyclopentyl-1-ethanol (0.3 g, 2.627 mmol) was added dropwise thereto, and the mixture was stirred at room temperature for 2 hours. After the reaction was confirmed by TLC to be complete, the reaction solution was filtered through celite, and a 5% aqueous sodium thiosulfate solution was added to the filtrate to remove iodine. The organic layer was washed twice with saturated saline and dehydrated over anhydrous sodium sulfate. The solvent was distilled off under reduced pressure, and then, the residue was purified using silica gel column chromatography (hexane) to obtain 2-cyclopentyl-1-iodoethane (0.46 g, yield: 84%).

1-Methoxycarbonyl-3-indoleacetic Acid Methyl Ester

Indole-3-acetic acid methyl ester (2.00 g, 10.57 mmol) was dissolved in dichloromethane (30 ml). To this solution, tetrabutylammonium iodide (TBAI, 30.0 mg, 0.081 mmol) and a 30% aqueous sodium hydroxide solution (24 ml) were added, and the mixture was cooled to 0° C. To the reaction solution, methyl formate chloride (1.96 g, 20.73 mmol) was added, and the mixture was stirred at 0° C. for 2 hours. After the reaction was confirmed by TLC to be complete, the reaction was terminated by the addition of 6 N hydrochloric acid. Water (50 ml) was added thereto, followed by extraction with chloroform (50 ml) three times. The organic layer was washed twice with saturated saline and dried over anhydrous sodium sulfate. The solvent was distilled off under reduced pressure, and the residue was then purified using silica gel column chromatography (hexane:ethyl acetate=8:2) to obtain 1-methoxycarbonyl-3-indoleacetic acid methyl ester (2.26 g, yield: 87%): $^1$H NMR (400 MHz, CDCl$_3$): δ 8.18 (d, J=7.0 Hz, 1H), 7.59 (s, 1H), 7.53 (d, J=7.7 Hz, 1H), 7.35 (t, J=7.5 Hz, 1H), 7.27 (t, J=7.4 Hz, 1H), 4.00 (s, 3H), 3.72 (s, 3H), 3.71 (s, 2H); $^{13}$C-NMR (100 MHz, CDCl$_3$) 171.1, 151.1, 135.2, 129.9, 124.6, 123.8, 122.8, 118.9, 115.0, 113.8, 53.5, 51.9, 30.6; EI-MS: m/z 247 [M]$^+$ α-(2-Cyclopentyl-1-ethyl)-1-methoxycarbonyl-3-indoleacetic Acid Methyl Ester

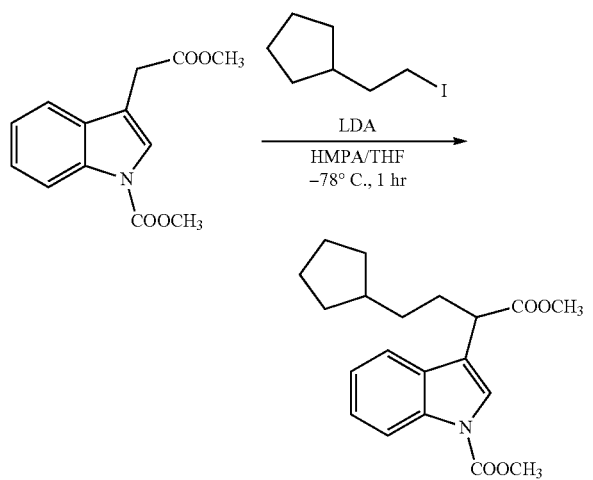

In a nitrogen atmosphere, 1-methoxycarbonyl-3-indoleacetic acid methyl ester (150 mg, 0.607 mmol) and hexamethylphosphoric triamide (544 mg, 3.036 mmol) were dissolved in anhydrous tetrahydrofuran 2 ml, and the solution was cooled to −78° C. A 1.5 M solution of lithium diisopropylamide in cyclohexane (0.61 ml, 1.5 eq) was slowly added dropwise thereto, and the mixture was stirred at −78° C. for 0.5 hours. To this reaction solution, a anhydrous tetrahydrofuran 1 ml solution of 2-cyclopentyl-1-iodoethane (204 mg, 0.910 mmol) was slowly added dropwise, and the mixture was stirred at −78° C. for 1 hour. After the reaction was confirmed by TLC to be complete, the temperature was adjusted to 0° C., and the reaction was terminated by the addition of water 5 ml, followed by extraction with ethyl acetate 5 ml three times. The organic layer was washed twice with saturated saline and dehydrated over anhydrous sodium sulfate. The solvent was distilled off under reduced pressure, and then, the residue was purified using silica gel column chromatography (hexane:ethyl acetate=95:5) to obtain α-(2-cyclopentyl-1-ethyl)-1-methoxycarbonyl-3-indoleacetic acid methyl ester (151 mg, yield: 72%): $^1$H NMR (400 MHz, CDCl3): δ 8.18 (d, J=6.8 Hz, 1H), 7.62 (d, J=7.7 Hz, 1H), 7.56 (s, 1H), 7.34 (t, J=7.4 Hz, 1H), 7.26 (t, J=7.3 Hz, 1H), 4.02 (s, 3H), 3.79 (t, J=7.6 Hz, 1H), 3.68 (s, 3H), 2.03 (m, 2H), 1.73-1.77 (m, 3H), 1.48-1.58 (m, 4H), 1.34 (q, J=7.2 Hz, 2H), 1.04-1.07 (m, 2H); $^{13}$C-NMR (100 MHz, CDCl3): δ 174.2, 151.3, 135.5, 129.5, 124.7, 122.9, 119.5, 119.3, 115.2, 53.7, 52.0, 42.8, 39.9, 34.1, 32.6, 32.5, 31.4, 25.1; EI-MS: m/z 343 [M]$^+$ α-(2-Cyclopentyl-1-ethyl)-1-methoxycarbonyl-3-indoleacetic Acid Methyl Ester (Compound #24)

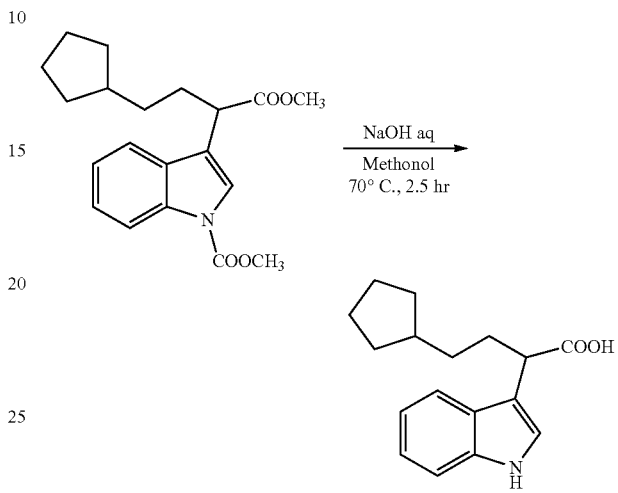

α-(2-Cyclopentyl-1-ethyl)-1-methoxycarbonyl-3-indoleacetic acid methyl ester (100 mg, 0.291 mmol) was dissolved in methanol (2 ml). To this solution, a 2 N aqueous sodium hydroxide solution (0.5 ml) was added, and the mixture was stirred at 70° C. for 2.5 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=95:5) to obtain α-(2-cyclopentyl-1-ethyl)-1-methoxycarbonyl-3-indoleacetic acid methyl ester (compound #24) (78.5 mg, yield: 99%): $^1$H NMR (400 MHz, CDCl$_3$): δ 8.19 (s, 1H), 7.69 (d, J=7.9 Hz, 1H), 7.29 (d, J=8.0 Hz, 1H), 7.16 (t, J=8.0 Hz, 1H), 7.10 (t, J=7.5 Hz, 1H), 7.06 (s, 1H), 3.83 (t, J=7.6 Hz, 1H), 2.01 (m, 2H), 1.70-1.75 (m, 3H), 1.45-1.55 (m, 4H), 1.34-1.37 (m, 2H), 0.98-1.03 (m, 2H); $^{13}$C NMR (100 MHz, CDCl$_3$): δ 180.7, 136.1, 126.5, 122.2, 122.0, 119.5, 119.2, 113.4, 111.2, 43.1, 39.9, 34.1, 32.5, 31.6, 25.1; IR (neat): 3415, 1703, 1457, 1339, 1098 cm$^{-1}$; FAB-MS: m/z 294 [M+Na]$^+$.

Synthesis of Compound #25

Cyclopentyliodomethane

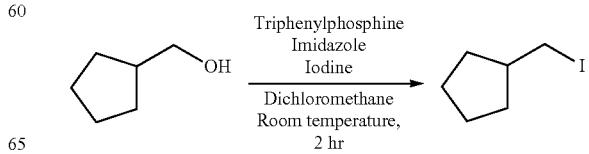

Triphenylphosphine (1.18 g, 4.491 mmol) and imidazole (0.31 g, 4.495 mmol) were dissolved in dichloromethane (5 ml), and the solution was stirred for 5 minutes. Then, iodine (1.14 g, 4.492 mmol) was added thereto, and the mixture was stirred for 10 minutes. A dichloromethane (1 ml) solution of cyclopentylmethanol (0.3 g, 2.995 mmol) was added dropwise thereto, and the mixture was stirred at room temperature for 2 hours. After the reaction was confirmed by TLC to be complete, the reaction solution was filtered through celite, and a 5% aqueous sodium thiosulfate solution was added to the filtrate to remove iodine. The organic layer was washed twice with saturated saline and dehydrated over anhydrous sodium sulfate. The solvent was distilled off under reduced pressure, and then, the residue was purified using silica gel column chromatography (hexane) to obtain cyclopentyliodomethane (0.53 g, yield: 84%).

α-Cyclopentylmethyl-1-methoxycarbonyl-3-indoleacetic Acid Methyl Ester

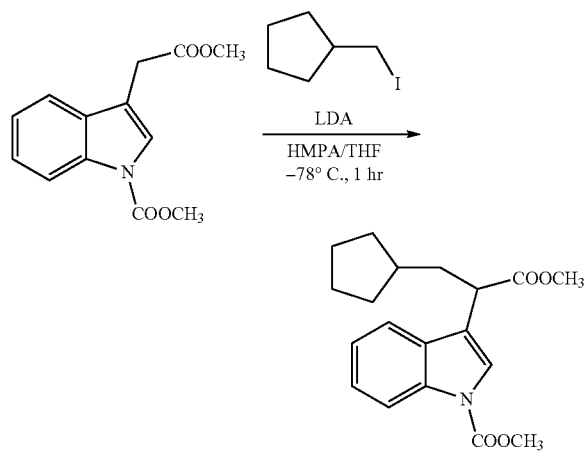

In a nitrogen atmosphere, 1-methoxycarbonyl-3-indoleacetic acid methyl ester (150 mg, 0.607 mmol) and hexamethylphosphoric triamide (HMPA, 544 mg, 3.036 mmol) were dissolved in tetrahydrofuran (2 ml), and the solution was cooled to −78° C. A 1.5 M solution of lithium diisopropylamide (LDA) in cyclohexane (0.61 ml, 1.5 eq) was slowly added dropwise thereto, and the mixture was stirred at −78° C. for 0.5 hours. To this reaction solution, a tetrahydrofuran (1 ml) solution of cyclopentyliodomethane (153 mg, 0.728 mmol) was slowly added dropwise, and the mixture was stirred at −78° C. for 1 hour. After the reaction was confirmed by TLC to be complete, the temperature was adjusted to 0° C., and the reaction was terminated by the addition of water (5 ml), followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=13:1) to obtain α-cyclopentylmethyl-1-methoxycarbonyl-3-indoleacetic acid methyl ester (153 mg, yield: 76%) $^1$H NMR (400 MHz, CDCl$_3$): δ 8.18 (d, J=6.0 Hz, 1H), 7.63 (d, J=7.8 Hz, 1H), 7.57 (s, 1H), 7.32 (t, J=7.4 Hz, 1H), 7.25 (t, J=7.4 Hz, 1H), 3.99 (s, 3H), 3.88 (t, J=7.7 Hz, 1H), 3.67 (s, 3H), 2.05 (m, 2H), 1.76-1.79 (m, 3H), 1.59-1.62 (m, 2H), 1.47-1.50 (m, 2H), 1.12-1.17 (m, 2H); $^{13}$C NMR (100 MHz, CDCl$_3$): δ 174.1, 151.1, 135.4, 129.4, 124.6, 122.8, 119.4, 119.2, 115.1, 53.6, 51.9, 41.7, 38.5, 37.9, 32.5, 32.3, 24.9; EI-MS: m/z 329 [M]$^+$.

α-Cyclopentylmethyl-3-indoleacetic Acid (Compound #25)

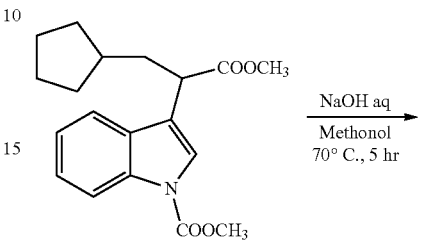

α-Cyclopentylmethyl-1-methoxycarbonyl-3-indoleacetic acid methyl ester (100 mg, 0.304 mmol) was dissolved in methanol (2 ml). To this solution, a 2 N aqueous sodium hydroxide solution (0.5 ml) was added, and the mixture was stirred at 70° C. for 2.5 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=95:5) to obtain α-cyclopentylmethyl-3-indoleacetic acid (compound #25) (58.3 mg, yield: 75%); $^1$H NMR (400 MHz, acetone-d$_6$): δ 10.13 (s, 1H), 7.70 (d, J=7.8 Hz, 1H), 7.38 (d, J=8.1 Hz, 1H), 7.28 (s, 1H), 7.10 (t, J=8.0 Hz, 1H), 7.02 (t, J=7.1 Hz, 1H), 3.73 (t, J=7.7 Hz, 1H), 2.06 (m, 2H), 1.78-1.83 (m, 3H), 1.47-1.61 (m, 4H), 1.17-1.20 (m, 2H); $^{13}$C NMR (100 MHz, acetone-d$_6$): δ 175.8, 137.3, 127.4, 123.1, 121.8, 119.5, 119.2, 114.1, 111.9, 42.4, 39.6, 38.7, 32.9, 32.9, 25.3, 25.3; IR (neat): 3418, 1699, 1456, 1339, 1097 cm$^{-1}$; FAB-MS: m/z 258 [M+H]$^+$.

Compounds #26 to 31 were each synthesized according to a method described in Muro Fumihito et. al. "Discovery of trans-4-[1-[[2,5-Dichloro-4-(1-methyl-3-indolylcarboxamido)phenyl]acetyl]-(4S)-methoxy-(2S)-pyrrolidinylmethoxy]cyclohexanecarboxylic Acid: An Orally Active, Selective Very Late Antigen-4 Antagonist" Journal of Medicinal Chemistry, 52 (24), 7974-7992; 2009.

Synthesis of Compound #26

N-Methyl-3-indoleacetic Acid Methyl Ester

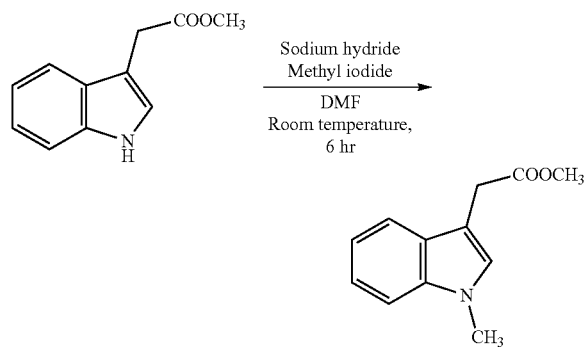

3-Indoleacetic acid methyl ester (200 mg, 1.1 mmol) was dissolved in N,N-dimethylformamide (3 mL). To the solution, sodium hydride (60 mg) was added. To this solution, methyl iodide (223 mg, 1.58 mmol) was added, and the mixture was stirred at room temperature for 6 hours. After the reaction was confirmed by TLC to be complete, the reaction solution was rendered acidic (pH=3 to 4) by the addition of 6 N hydrochloric acid, and water (5 ml) was added thereto, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=5:1) to obtain N-methyl-3-indoleacetic acid methyl ester (140 mg, yield: 65%); $^1$H NMR (400 MHz, CDCl$_3$): δ 7.60 (d, J=7.9 Hz, 1H), 7.29 (d, J=8.2 Hz, 1H), 7.23 (dd, J=8.2, 7.9 Hz, 1H), 7.12 (dd, J=8.2, 7.9 Hz, 1H), 7.03 (s, 1H), 3.75 (s, 3H), 3.77 (s, 2H), 3.69 (s, 3H); $^{13}$C NMR (100 MHz, CDCl$_3$): δ 172.6, 136.9, 127.7, 121.7 (2C), 119.26, 118.9, 109.3, 106.8, 51.9, 32.7, 31.0.

N-Methyl-3-indoleacetic Acid (Compound #26)

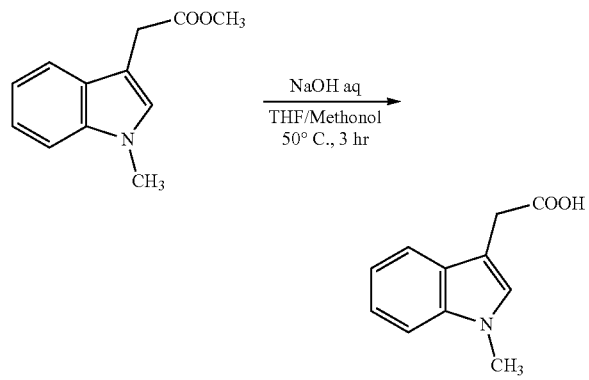

N-Methyl-3-indoleacetic acid methyl ester (120 mg, 0.59 mmol) was dissolved in tetrahydrofuran (0.5 ml). To this solution, methanol (0.5 ml) and a 2 N aqueous sodium hydroxide solution (0.25 ml) were added, and the mixture was stirred at 50° C. for 3 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=10:1) to obtain N-methyl-3-indoleacetic acid (compound #26) (108 mg, yield: 96%); $^1$H NMR (400 MHz, CDCl3): δ 7.59 (d, J=8.0 Hz, 1H), 7.35 (d, J=8.1 Hz, 1H), 7.18 (s, 1H), 7.16 (dd, J=7.0, 6.1 Hz, 1H), 7.04 (dd, J=8.1, 6.7 Hz, 1H), 3.79 (s, 3H), 3.73 (s, 2H). $^{13}$C NMR (100 MHz, CDCl$_3$): 177.6, 136.8, 127.9, 127.5, 121.8, 119.2, 118.9, 109.5, 106.1, 53.7, 31.7.

Synthesis of Compound #27

N-Ethyl-3-indoleacetic Acid Methyl Ester

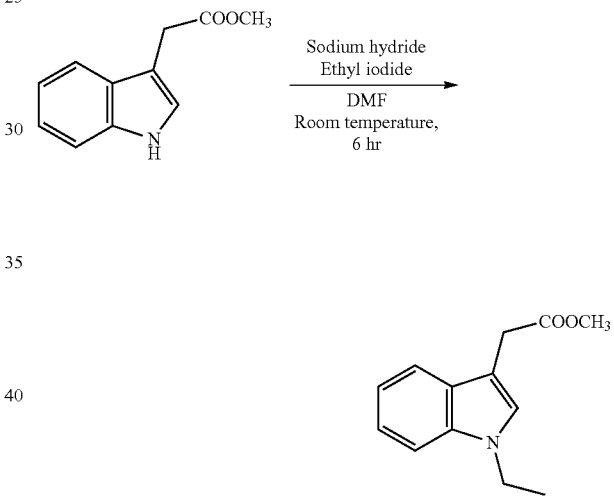

3-Indoleacetic acid methyl ester (200 mg, 1.1 mmol) was dissolved in N,N-dimethylformamide (3 mL). To the solution, sodium hydride (60 mg) was added. To this solution, ethyl iodide (246 mg, 1.58 mmol) was added, and the mixture was stirred at room temperature for 6 hours. After the reaction was confirmed by TLC to be complete, the reaction solution was rendered acidic (pH=3 to 4) by the addition of 6 N hydrochloric acid, and water (5 ml) was added thereto, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=5:1) to obtain N-ethyl-3-indoleacetic acid methyl ester (133 mg, yield: 58%); $^1$H NMR (400 MHz, CDCl$_3$): δ 7.60 (d, J=7.8 Hz, 1H), 7.31 (d, J=8.3 Hz, 1H), 7.21 (dd, J=8.3, 7.8 Hz, 1H), 7.11 (dd, J=8.3, 7.8 Hz, 1H), 7.09 (s, 1H), 4.11 (q, J=7.3 Hz, 2H), 3.76 (s, 2H), 3.68 (s, 3H), 1.43 (t, J=7.3, 3H); $^{13}$C NMR (100 MHz, CDCl$_3$): δ 172.6, 160.8, 135.9, 127.8, 125.9, 121.6, 119.0, 109.3, 51.9, 40.8, 31.1, 15.4.

N-Ethyl-3-indoleacetic Acid (Compound #27)

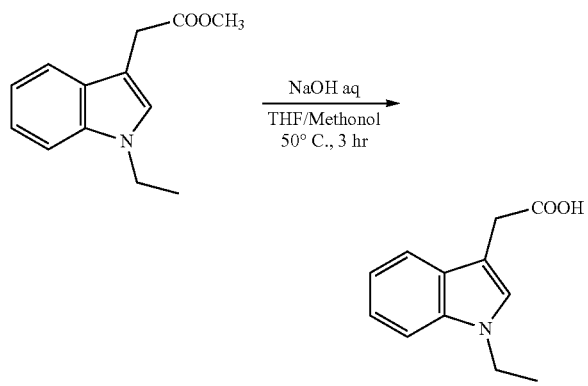

N-Methyl-3-indoleacetic acid methyl ester (120 mg, 0.59 mmol) was dissolved in tetrahydrofuran (0.5 ml). To this solution, methanol (0.5 ml) and a 2 N aqueous sodium hydroxide solution (0.25 ml) were added, and the mixture was stirred at 50° C. for 3 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=10:1) to obtain N-methyl-3-indoleacetic acid (compound #27) (108 mg, yield: 97%); $^1$H NMR (400 MHz, CDCl$_3$): δ 7.60 (d, J=7.9 Hz, 1H), 7.40 (d, J=8.2 Hz, 1H), 7.25 (s, 1H), 7.15 (ddd, J=7.5, 7.6 Hz, 1H), 7.04 (ddd, J=7.3, 7.5 Hz, 1H), 4.20 (q, J=7.3 Hz, 2H), 3.74 (s, 2H), 1.39 (t, J=7.3 Hz, 3H); $^{13}$C NMR (100 MHz, CDCl$_3$): δ 173.3, 136.8, 129.0, 127.1, 122.0, 119.8, 119.4, 110.1, 108.1, 41.1, 31.9, 15.8.

Synthesis of Compound #28

N-Propyl-3-indoleacetic Acid Methyl Ester

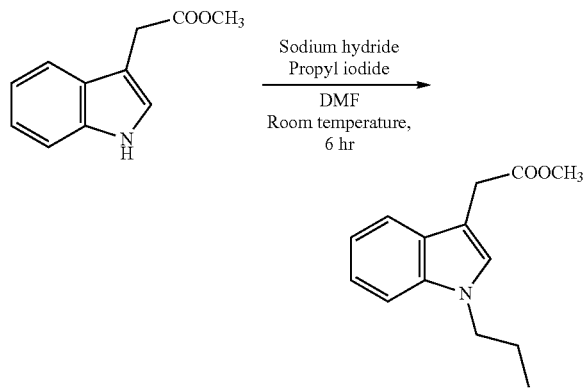

3-Indoleacetic acid methyl ester (200 mg, 1.1 mmol) was dissolved in N,N-dimethylformamide (3 mL). To the solution, sodium hydride (60 mg) was added. To this solution, propyl iodide (268 mg, 1.58 mmol) was added, and the mixture was stirred at room temperature for 6 hours. After the reaction was confirmed by TLC to be complete, the reaction solution was rendered acidic (pH=3 to 4) by the addition of 6 N hydrochloric acid, and water (5 ml) was added thereto, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=6:1) to obtain N-propyl-3-indoleacetic acid methyl ester (136 mg, yield: 56%); $^1$H NMR (400 MHz, CDCl$_3$): δ 7.60 (d, J=7.8 Hz, 1H) 7.31 (d, J=8.3 Hz, 1H) 7.21 (dd, J=8.0, 7.1 Hz, 1H) 7.11 (dd, J=7.7, 6.9 Hz, 1H) 7.08 (s, 1H) 4.04 (t, J=7.1 Hz, 2H) 3.77 (s, 2H) 3.69 (s, 3H) 1.86 (m, 2H) 0.93 (t, J=7.3 Hz, 3H); $^{13}$C NMR (100 MHz, CDCl$_3$): δ 172.6, 136.2, 127.70, 126.7, 121.5, 119.0, 119.0, 109.4, 106.6, 51.9, 47.9, 31.1, 23.5, 11.5.

N-Propyl-3-indoleacetic Acid (Compound #28)

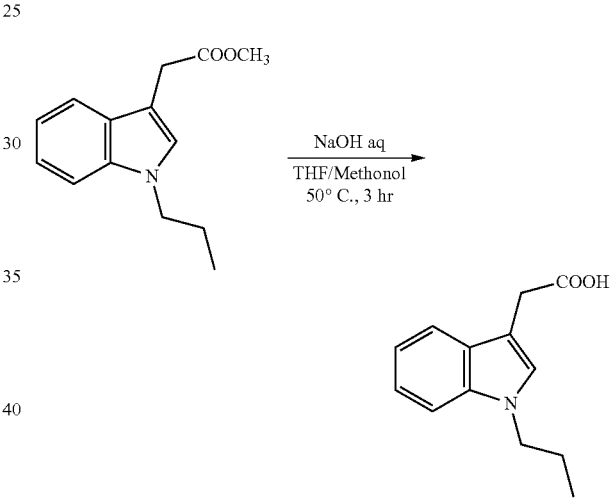

N-Propyl-3-indoleacetic acid methyl ester (120 mg, 0.52 mmol) was dissolved in tetrahydrofuran (0.5 ml). To this solution, methanol (0.5 ml) and a 2 N aqueous sodium hydroxide solution (0.25 ml) were added, and the mixture was stirred at 50° C. for 3 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=10:1) to obtain N-propyl-3-indoleacetic acid (compound #28) (103 mg, yield: 98%); $^1$H NMR (400 MHz, CDCl$_3$): δ 7.60 (d, J=8.0 Hz, 1H), 7.32 (d, J=8.2 Hz, 1H), 7.21 (dd, J=7.2, 8.0 Hz, 1H), 7.11 (dd, J=7.3, 9.8 Hz, 1H), 7.09 (s, 1H), 4.04 (t, J=7.1 Hz, 2H), 3.79 (s, 2H), 1.85 (m, 2H), 0.92 (t, J=7.4 Hz, 3H); $^{13}$C NMR (100 MHz, CDCl$_3$): δ 177.5, 136.2, 127.6, 127.0, 121.6, 119.1, 119.0, 109.5, 106.0, 53.7, 31.7, 23.5, 11.5.

Synthesis of Compound #29

N-Butyl-3-indoleacetic Acid Methyl Ester

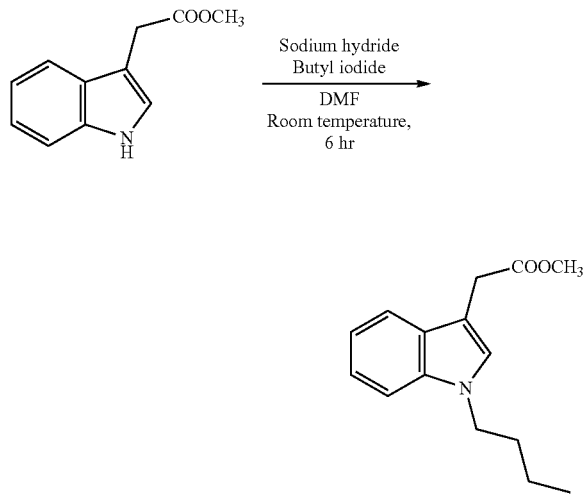

3-Indoleacetic acid methyl ester (200 mg, 1.1 mmol) was dissolved in N,N-dimethylformamide (3 mL). To the solution, sodium hydride (60 mg) was added. To this solution, butyl iodide (290 mg, 1.58 mmol) was added, and the mixture was stirred at room temperature for 6 hours. After the reaction was confirmed by TLC to be complete, the reaction solution was rendered acidic (pH=3 to 4) by the addition of 6 N hydrochloric acid, and water (5 ml) was added thereto, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=6:1) to obtain N-butyl-3-indoleacetic acid methyl ester (137 mg, yield: 53%); $^1$H NMR (400 MHz, CDCl$_3$): δ 7.60 (d, J=7.8 Hz, 1H), 7.32 (d, J=8.2 Hz, 1H), 7.21 (dd, J=8.5, 9.8 Hz, 1H), 7.11 (dd, J=9.7, 7.4 Hz, 1H), 7.08 (s, 1H), 4.08 (t, J=7.1 Hz, 2H), 3.77 (s, 2H), 3.69 (s, 3H), 1.80 (m, 2H), 1.34 (m, 2H), 0.93 (t, J=7.4 Hz, 3H); $^{13}$C NMR (100 MHz, CDCl$_3$): 172.6, 136.2, 127.7, 126.7, 121.5, 119.0, 119.0, 109.4, 106.7, 51.9, 46.0, 32.3, 31.1, 20.2, 13.7.

N-Butyl-3-indoleacetic Acid (Compound #29)

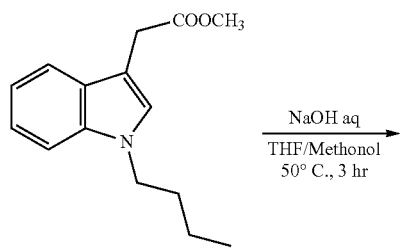

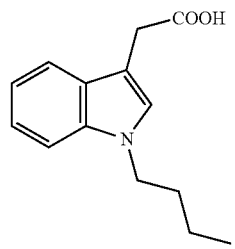

N-Butyl-3-indoleacetic acid methyl ester (120 mg, 0.52 mmol) was dissolved in tetrahydrofuran (0.5 ml). To this solution, methanol (0.5 ml) and a 2 N aqueous sodium hydroxide solution (0.25 ml) were added, and the mixture was stirred at 50° C. for 3 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=10:1) to obtain N-butyl-3-indoleacetic acid (compound #29) (104 mg, yield: 98%); $^1$H NMR (400 MHz, CDCl$_3$): δ 7.59 (d, J=7.9 Hz, 1H), 7.31 (d, J=8.2 Hz, 1H), 7.20 (dd, J=7.1, 7.9 Hz, 1H), 7.11 (dd, J=7.3, 7.5 Hz, 1H), 7.07 (s, 1H), 4.06 (t, J=7.2 Hz, 2H), 3.78 (s, 2H), 1.79 (m, 2H), 1.33 (m, 2H), 0.92 (t, J=7.4, 3H); $^{13}$C NMR (100 MHz, CDCl$_3$): δ 178.0, 136.1, 127.6, 126.9, 121.6119.10, 119.0, 109.5, 106.0, 53.6, 31.7, 29.1, 20.2, 13.7.

Synthesis of Compound #30

N-Hexyl-3-indoleacetic Acid Methyl Ester

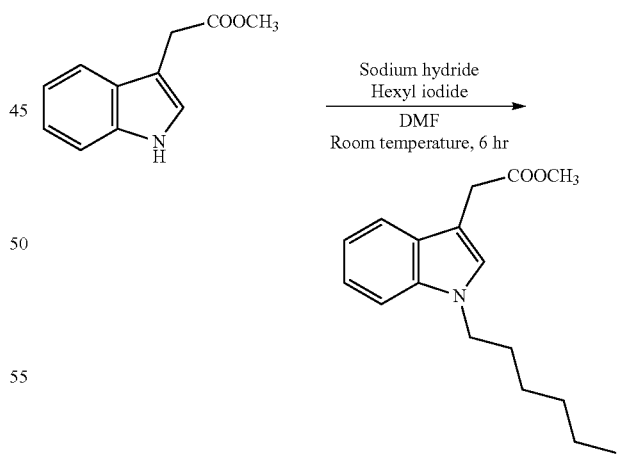

3-Indoleacetic acid methyl ester (200 mg, 1.1 mmol) was dissolved in N,N-dimethylformamide (3 mL). To the solution, sodium hydride (60 mg) was added. To this solution, hexyl iodide (334 mg, 1.58 mmol) was added, and the mixture was stirred at room temperature for 6 hours. After the reaction was confirmed by TLC to be complete, the reaction solution was rendered acidic (pH=3 to 4) by the addition of 6 N hydrochloric acid, and water (5 ml) was added thereto, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=6:1) to obtain N-hexyl-3-indoleacetic acid methyl ester (147 mg, yield: 51%); $^1$H NMR (400 MHz, CDCl$_3$): δ 7.60 (d, J=7.8 Hz, 1H) 7.31, (d, J=8.2 Hz, 1H), 7.20 (ddd, J=8.6, 5.6 Hz, 1H), 7.11 (ddd, J=8.0, 7.3 Hz, 1H), 7.08 (s, 2H), 4.06 (t, J=7.2 Hz, 2H), 3.77 (s, 2H), 3.69 (s, 3H), 1.81 (m, 2H), 1.30 (m, 6H), 0.87 (t, J=6.9 Hz, 3H); $^{13}$C NMR (100 MHz, CDCl$_3$): 172.6, 136.1, 127.7, 126.7, 121.5, 119.0, 119.0, 109.4, 106.6, 51.9, 46.3, 31.4, 31.1, 30.2, 22.6, 22.5, 14.0.

N-Hexyl-3-indoleacetic Acid (Compound #30)

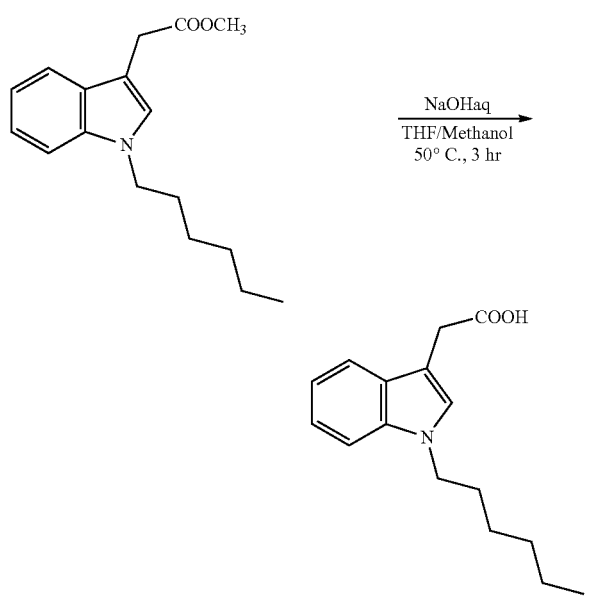

N-Hexyl-3-indoleacetic acid methyl ester (120 mg, 0.52 mmol) was dissolved in tetrahydrofuran (0.5 ml). To this solution, methanol (0.5 ml) and a 2 N aqueous sodium hydroxide solution (0.25 ml) were added, and the mixture was stirred at 50° C. for 3 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=10:1) to obtain N-hexyl-3-indoleacetic acid (compound #30) (103 mg, yield: 96%); $^1$H NMR (400 MHz, CDCl$_3$): δ 7.59 (d, J=7.9 Hz, 1H), 7.31 (d, J=8.2 Hz, 1H), 7.20 (ddd, J=7.9, 7.3 Hz, 1H), 7.20 (ddd, J=7.4, 7.7 Hz, 1H), 7.07 (1H, s, 1H), 4.05 (t, J=7.2 Hz, 2H), 3.78 (s, 2H), 1.81 (m, 2H), 1.31 (m, 6H), 0.88 (t, J=6.3 Hz, 3H); $^{13}$C NMR (100 MHz, CDCl$_3$): δ 178.0, 136.1, 127.6, 127.6, 121.6, 119.1, 119.0, 109.5, 106.0, 53.7, 31.7, 29.2, 28.9, 27.0, 23.0, 14.02.

Synthesis of Compound #31

N-Heptyl-3-indoleacetic Acid Methyl Ester

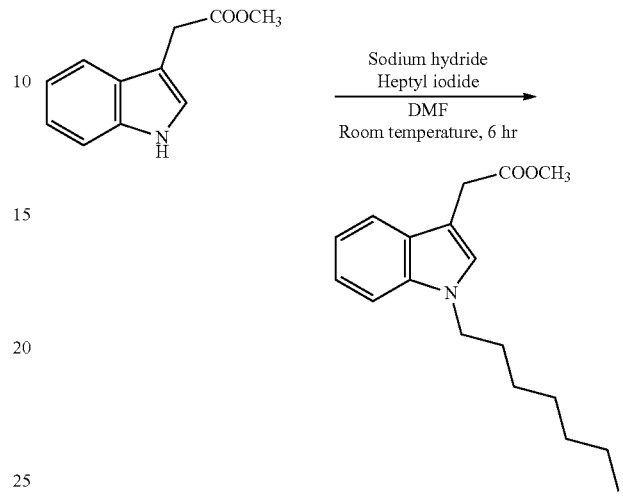

3-Indoleacetic acid methyl ester (200 mg, 1.1 mmol) was dissolved in N,N-dimethylformamide (3 mL). To the solution, sodium hydride (60 mg) was added. To this solution, heptyl iodide (358 mg, 1.58 mmol) was added, and the mixture was stirred at room temperature for 6 hours. After the reaction was confirmed by TLC to be complete, the reaction solution was rendered acidic (pH=3 to 4) by the addition of 6 N hydrochloric acid, and water (5 ml) was added thereto, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=6:1) to obtain N-heptyl-3-indoleacetic acid methyl ester (148 mg, yield: 49%); $^1$H NMR (400 MHz, CDCl$_3$): δ 3.69 (3H, s), 7.60 (1H, d, J=7.8), 7.31 (1H, d, J=8.2) 7.11 (1H, dd, J=8.2, 6.7), 7.08 (1H, s), 4.06 (2H, t, J=7.1), 3.77 (2H, s) 3.59 (1H, dd, J=8.2, 6.7), 1.82 (2H, m), 1.29 (8H, m), 0.87 (3H, t, J=7.1); $^{13}$C NMR (100 MHz, CDCl$_3$): δ 172.57, 136.16, 127.70, 126.66, 121.54, 118.98, 118.98, 109.43, 106.64, 51.89, 46.31, 31.67, 31.11, 30.24, 28.89, 26.96, 22.55, 14.02.

N-Heptyl-3-indoleacetic Acid (Compound #31)

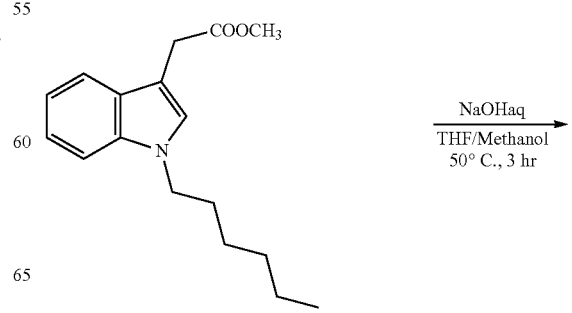

-continued

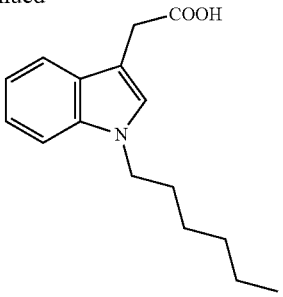

N-Heptyl-3-indoleacetic acid methyl ester (120 mg, 0.52 mmol) was dissolved in tetrahydrofuran (0.5 ml). To this solution, methanol (0.5 ml) and a 2 N aqueous sodium hydroxide solution (0.25 ml) were added, and the mixture was stirred at 50° C. for 3 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=10:1) to obtain N-heptyl-3-indoleacetic acid (compound #31) (180 mg, yield: 95%); $^1$H NMR (400 MHz, CDCl$_3$): δ 7.59 (1H, d, J=7.96), 7.31 (1H, d, J=8.17), 7.21 (1H, ddd, J=8.49, 6.73), 7.11 (1H, ddd, J=7.21, 7.29), 7.08 (1H, S), 4.06 (2H, t, J=7.25), 3.79 (2H, s) 1.81 (2H, m) 1.29 (8H, m) 0.87 (3H, t, J=6.83); $^{13}$C NMR (100 MHz, CDCl$_3$): δ 177.81, 136.10, 127.55, 126.85, 121.62, 119.11, 118.94, 109.49, 105.91, 53.63, 46.32, 30.99, 29.68, 29.16, 26.64, 22.49, 13.99.

Compounds #33 and 34 were each synthesized with α-(7-hydroxy-1-naphthalenyl)-acetic acid ethyl ester as a key intermediate. The α-(7-hydroxy-1-naphthalenyl)-acetic acid ethyl ester was synthesized according to a method described in E. Tsuda et. al., "Alkoxy-auxins are selective inhibitors of auxin transport mediated by PIN, ABCB, and AUX1 transporters" Journal of Biological Chemistry, 286 (3), 2354-2364; 2011.

Synthesis of Compound #33

α-(7-Butoxy-1-naphthalenyl)-acetic Acid Ethyl Ester

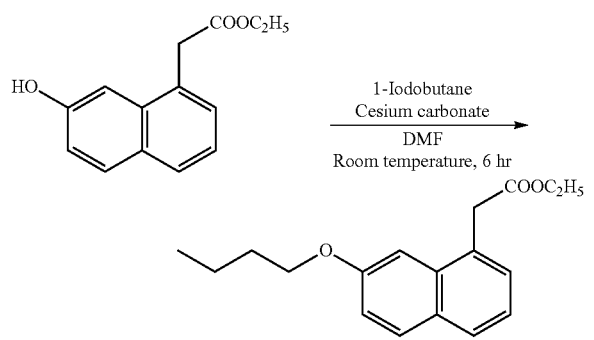

α-(7-Hydroxy-1-naphthalenyl)-acetic acid ethyl ester (90 mg, 0.39 mmol) was dissolved in N,N-dimethylformamide (5 ml). To this solution, 1-iodobutane (107 mg, 0.58 mmol) was added dropwise, then cesium carbonate (127 mg, 0.39 mmol) was added, and the mixture was stirred at room temperature for 6 hours. After the reaction was confirmed by TLC to be complete, water (5 ml) was added to the reaction solution, followed by extraction with ethyl acetate (10 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=7:3) to obtain α-(7-butoxy-1-naphthalenyl)-acetic acid ethyl ester as a colorless oil (92 mg, yield: 83%); $^1$H NMR (400 MHz, CDCl$_3$): δ 7.71 (d, J=8.9 Hz, 1H), 7.35 (d, J=6.9 Hz, 1H), 7.67 (d, J=8.1 Hz, 1H), 7.27 (d, J=2.3 Hz, 1H), 7.25 (dd, J=8.1, 6.9 Hz, 1H), 7.14 (q, J=8.9, 2.3 Hz, 1H), 4.12 (q, J=7.1 Hz, 2H), 4.07 (t, J=6.6 Hz, 2H), 3.97 (s, 2H), 1.82 (m, 2H), 1.53 (m, 2H), 1.19 (t, J=7.1 Hz, 3H), 0.96 (t, J=7.5 Hz, 3H); $^{13}$C NMR (100 MHz, CDCl$_3$): δ 171.5, 157.4, 133.2, 130.0, 129.3, 129.1, 128.3, 127.6, 123.0, 118.5, 103.2, 67.6, 60.8, 39.5, 31.2, 19.2, 14.1, 13.8; IR (neat): 2958, 1733, 1510, 1459, 1210, 1156 cm$^{-1}$; HREI-MS found m/z286.1556 [M]$^+$, calcd for 286.1569 (C$_{18}$H$_{22}$O$_3$).

α-(7-Butoxy-1-naphthalenyl)-acetic Acid (Compound #33)

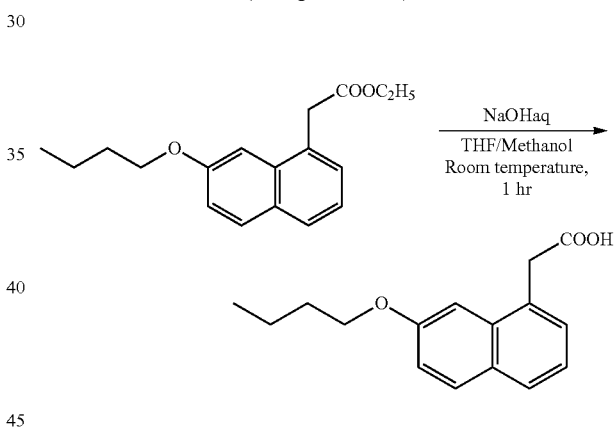

α-(7-Butoxy-1-naphthalenyl)-acetic acid ethyl ester (75 mg, 0.26 mmol) was dissolved in a mixed solution of tetrahydrofuran:methanol:2 M aqueous sodium hydroxide solution=2:2:1 (1.5 ml), and the solution was stirred at room temperature for 1 hour. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (10 ml) three times. The organic layer was washed twice with saturated saline and dehydrated over anhydrous sodium sulfate. The solvent was distilled off under reduced pressure, and then, the residue was purified using silica gel column chromatography (chloroform:methanol=9:1) to obtain α-(7-butoxy-1-naphthalenyl)-acetic acid (compound #33) (67 mg, yield: 98%); Melting point: 102 to 104° C.; $^1$H NMR (400 MHz, CDCl$_3$): δ 7.75 (d, J=8.9 Hz, 1H), 7.71 (d, J=8.1 Hz, 1H), 7.34 (d, J=6.9 Hz, 1H), 7.26 (dd, J=8.1, 6.9 Hz, 1H), 7.23 (d, J=2.0 Hz, 1H), 7.16 (q, J=8.9, 2.0 Hz, 1H), 4.05 (t, J=6.5 Hz, 2H), 4.00 (s, 2H), 1.51 (m, 2H), 1.80 (m, 2H), 0.98 (t, J=7.4 Hz, 3H); $^{13}$C NMR (100 MHz, CDCl$_3$): δ 177.6, 157.6, 133.2, 130.2, 129.1, 128.6, 127.9 (2C), 123.0, 118.7, 103.1, 67.7, 39.2, 31.2, 19.3, 13.8; IR (neat): 3021, 2931, 1699, 1457, 1138 cm$^{-1}$; HREI-MS found m/z 258.1268 [M]$^{+}$, calcd for 258.1256 ($C_{16}H_{18}O_3$).

Synthesis of Compound #34

α-(7-Pentoxy-1-naphthalenyl)-acetic Acid Ethyl Ester

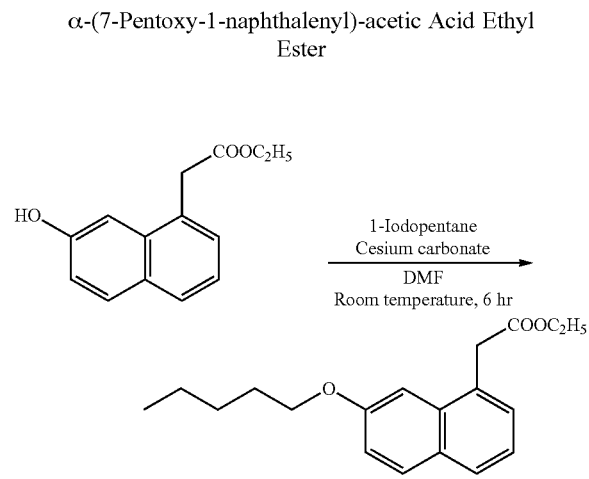

α-(7-Hydroxy-1-naphthalenyl)-acetic acid ethyl ester (90 mg, 0.39 mmol) was dissolved in N,N-dimethylformamide (5 ml). To this solution, 1-iodopentane (116 mg, 0.58 mmol) was added dropwise, then cesium carbonate (127 mg, 0.39 mmol) was added, and the mixture was stirred at room temperature for 6 hours. After the reaction was confirmed by TLC to be complete, water (5 ml) was added to the reaction solution, followed by extraction with ethyl acetate (10 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=7:3) to obtain α-(7-pentoxy-1-naphthalenyl)-acetic acid ethyl ester as a colorless oil (103 mg, yield: 88%): $^1$H NMR (400 MHz, CDCl$_3$): δ 1.00 (t, J=7.2 Hz, 3H), 1.26 (t, J=7.1 Hz, 3H), 1.48 (m, 2H), 1.55 (m, 2H), 1.91 (m, 2H), 4.03 (s, 2H), 4.13 (t, J=6.5 Hz, 2H), 4.19 (q, J=7.1 Hz, 2H), 7.20 (dd, J=8.9, 2.5 Hz, 1H), 7.31 (dd, J=8.1, 7.0 Hz, 1H), 7.33 (d, J=2.5 Hz, 1H), 7.41 (d, J=7.0 Hz, 1H), 7.74 (d, J=8.1 Hz, 1H), 7.78 (d, J=8.9 Hz, 1H); $^{13}$C NMR (100 MHz, CDCl$_3$): δ 171.5, 157.4, 133.2, 130.0, 129.3, 129.1, 128.4, 127.6, 123.0, 118.5, 103.2, 67.8, 60.8, 39.6, 28.9, 28.2, 22.4, 14.1, 14.0; IR (neat): 2969, 1734, 1509, 1459, 1160 cm$^{-1}$; HREI-MS found m/z 300.1727 [M]$^+$, calcd for 300. 1725 ($C_{19}H_{24}O_3$).

α-(7-Pentoxy-1-naphthalenyl)-acetic Acid (Compound #34)

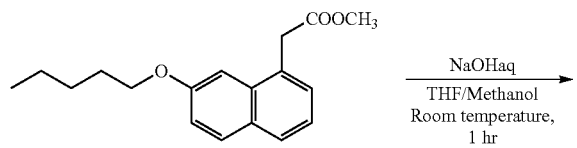

α-(7-Pentoxy-1-naphthalenyl)-acetic acid ethyl ester (90 mg, 0.30 mmol) was dissolved in a mixed solution of tetrahydrofuran:methanol:2 M aqueous sodium hydroxide solution=2:2:1 (1.5 ml), and the solution was stirred at room temperature for 1 hour. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (10 ml) three times. The organic layer was washed twice with saturated saline and dehydrated over anhydrous sodium sulfate. The solvent was distilled off under reduced pressure, and then, the residue was purified using silica gel column chromatography (chloroform:methanol=6:1) to obtain α-(7-pentoxy-1-naphthalenyl)-acetic acid (compound #34) (75 mg, yield: 92%); Melting point: 104 to 106° C.; $^1$H NMR (400 MHz, CDCl$_3$): δ 7.71 (d, J=8.1 Hz, 1H), 7.39 (d, J=6.9 Hz, 1H), 7.26 (t, J=8.1, 6.9 Hz, 1H), 7.21 (d, J=2.1 Hz, 1H), 7.15 (dd, J=8.9, 2.1 Hz, 1H), 4.03 (t, J=6.5 Hz, 2H), 4.00 (s, 2H), 3.87 (d, J=8.9 Hz, 1H), 1.82 (m, 2H), 1.45 (m, 2H), 1.39 (m, 2H), 0.93 (t, J=7.1 Hz, 3H); $^{13}$C NMR (100 MHz, CDCl$_3$): δ 177.6, 157.6, 133.2, 130.2, 129.1, 128.6, 128.4, 128.0, 123.0, 118.7, 103.1, 68.0, 39.1, 28.9, 28.2, 22.5, 14.0; IR (neat): 3014, 2945, 1689, 1463, 1169 cm$^{-1}$; HREI-MS found m/z 272.1378 [M]$^+$, calcd for 272.1412 ($C_{17}H_{20}O_3$).

Compounds #35 to 37 were each synthesized with 5-hydroxy-3-indoleacetic acid methyl ester as a key intermediate.

5-Hydroxy-3-indoleacetic Acid Methyl Ester

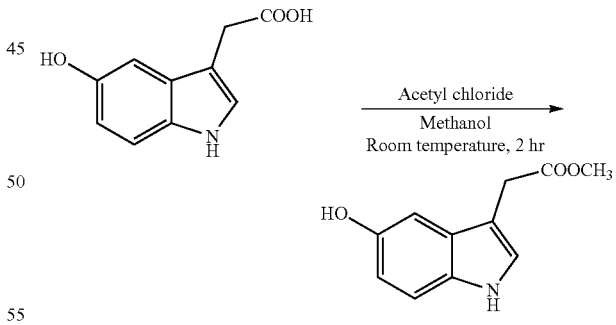

5-Hydroxy-3-indoleacetic acid (1.00 g) was dissolved in methanol (25 ml). To the solution, acetyl chloride (1.0 ml) was slowly added dropwise, and the mixture was stirred at room temperature for 2 hours. After the reaction was confirmed by TLC to be complete, the reaction was terminated by the addition of a saturated aqueous solution of sodium bicarbonate, and the solvent was distilled off under reduced pressure. Then, water (20 ml) was added to the residue, followed by extraction with ethyl acetate (50 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=3:2) to obtain 5-hydroxy-3-indoleacetic acid methyl ester (1.05 g, yield: 98%); $^1$H NMR (400 MHz, CDCl$_3$): δ 7.20 (s, J=8.7 Hz, 1H), 7.13 (d, J=2.4 Hz, 1H), 7.00 (d, J=2.4 Hz, 1H), 6.78 (dd, J=8.8, 2.4 Hz, 1H), 3.72 (s, 2H), 3.70 (s, 3H); $^{13}$C NMR (100 MHz, CDCl$_3$): δ 172.6, 149.6, 131.4, 127.9, 124.2, 112.1, 111.9, 103.4, 107.8, 52.0, 31.2; IR (neat): 3411, 3000, 2952, 1728, 1459, 1459, 1154 cm$^{-1}$; EI-MS m/z [M]$^+$205, 146; HREI-MS found m/z 205.0761 [M]$^+$, calcd for 205.0739 ($C_{11}H_{11}NO_3$).

Synthesis of Compound #35

5-(3,5-Dimethoxybenzyloxy)-3-indoleacetic Acid Methyl Ester

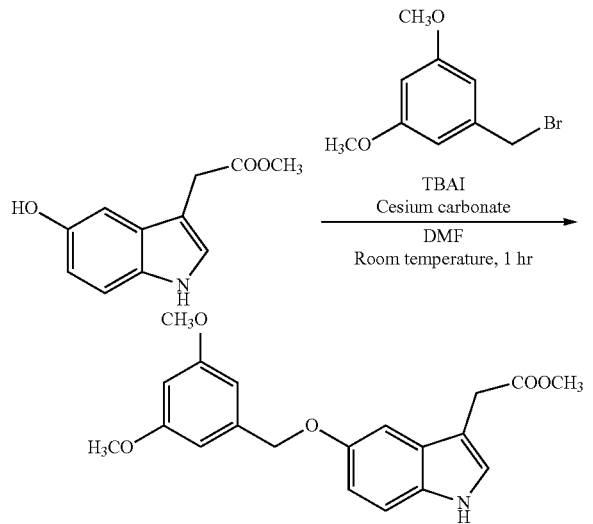

5-Hydroxy-3-indoleacetic acid methyl ester (42.9 mg, 0.21 mmol) was dissolved in N,N-dimethylformamide (DMF). To this solution, 3,5-dimethoxybenzyl bromide (82.2 mg, 0.36 mmol) was added dropwise, then tetra-N-butylammonium iodide (83.0 mg, 2.00 mmol) and cesium carbonate (136.37 mg, 0.42 mmol) put aside in another container were added, and the mixture was stirred at room temperature for 1 hour. After the reaction was confirmed by TLC to be complete, the reaction was terminated by the addition of an aqueous sodium bicarbonate solution, followed by extraction with ethyl acetate (50 ml) three times. The organic layer was washed twice with saturated saline and dehydrated over anhydrous sodium sulfate. The solvent was distilled off under reduced pressure, and then, the residue was purified using silica gel column chromatography (hexane:ethyl acetate=3:2) to obtain 5-(3,5-dimethoxybenzyloxy)-3-indoleacetic acid methyl ester (81.5 mg, yield: 94%); $^1$H NMR (400 MHz, CDCl$_3$): δ 7.17 (d, J=2.2 Hz, 1H), 7.12 (d, J=8.7 Hz, 1H), 7.04 (s, 2H), 6.92 (dd, J=8.7, 2.2 Hz, 1H), 6.64 (d, J=2.2 Hz, 2H), 6.41 (t, J=2.2 Hz, 1H), 5.13 (s, 2H), 3.78 (s, 6H), 3.72 (s, 2H), 3.67 (s, 3H); $^{13}$C NMR (100 MHz, CDCl$_3$): δ 172.5, 160.9 (2C), 153.2, 140.0, 131.4, 124.0, 127.5, 113.0, 111.9, 107.9, 105.2 (2C), 102.2, 99.8, 70.8, 55.3 (2C), 51.9, 31.2; IR (neat): 3396, 2948, 1734, 1449, 1159 cm$^{-1}$.

5-(3,5-Dimethoxybenzyloxy)-3-indoleacetic Acid (Compound #35)

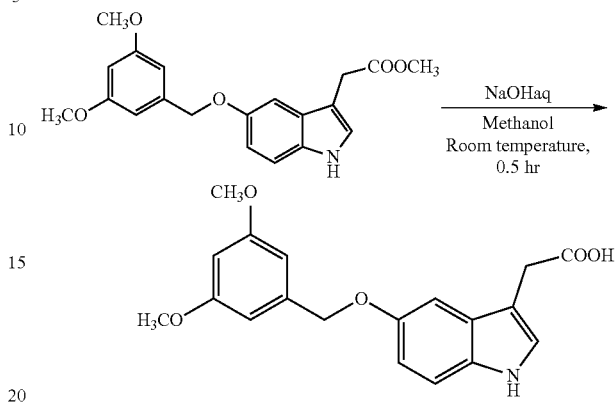

5-(3,5-Dimethoxybenzyloxy)-3-indoleacetic acid methyl ester (81.5 mg, 0.23 mmol) was dissolved in tetrahydrofuran (0.5 ml). To this solution, methanol (0.5 ml) and a 2 N aqueous sodium hydroxide solution (0.25 ml) were added, and the mixture was stirred at room temperature for 0.5 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=10:1) to obtain 5-(3,5-dimethoxybenzyloxy)-3-indoleacetic acid (compound #35) (55.2 mg, yield: 100%); Melting point: 146.1 to 148.6° C.; H NMR (400 MHz, CDCl$_3$): δ 7.19 (d, J=8.8 Hz, 1H), 7.12 (d, J=2.2 Hz, 1H), 7.06 (s, 1H), 6.92 (dd, J=8.8, 2.2 Hz, 1H), 6.68 (d, J=2.2 Hz, 2H), 6.40 (t, J=2.2 Hz, 1H), 5.01 (S, 2H), 3.77 (S, 6H), 3.73 (s, 2H); $^{13}$C NMR (100 MHz, CDCl$_3$): δ 177.5, 160.8 (2C), 153.3, 140.0, 131.4, 127.5, 124.1, 113.1, 112.0, 107.4, 105.3 (2C), 102.2, 99.9, 70.9, 55.3 (2C), 31.1; IR (neat): 3406, 2957, 2926, 1702, 1458, 1155 cm$^{-1}$.

Synthesis of Compound #36

5-Methoxy-3-indoleacetic Acid Methyl Ester

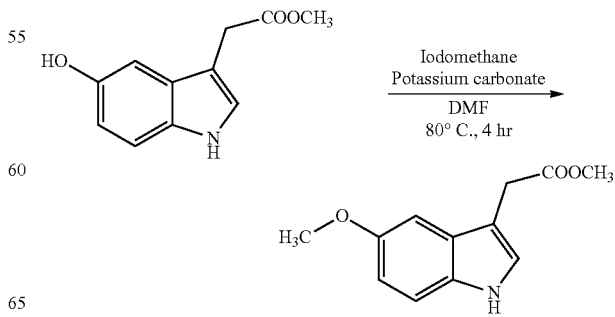

5-Hydroxy-3-indoleacetic acid methyl ester (99.3 mg, 0.48 mmol) was dissolved in N,N-dimethylformamide (2 ml). To this solution, iodomethane (206.2 mg, 1.45 mmol) was added dropwise, then potassium carbonate (200.8 mg, 1.45 mmol) put aside in another container was added, and the mixture was stirred overnight at room temperature and subsequently stirred at 80° C. for 4 hours. After the reaction was confirmed by TLC to be complete, a 10% aqueous sodium bicarbonate solution (20 ml) was added thereto, followed by extraction with ethyl acetate (50 ml). The organic layer was washed twice with saturated saline and dehydrated over anhydrous sodium sulfate. The solvent was distilled off under reduced pressure, and then, the residue was purified using silica gel column chromatography (hexane:ethyl acetate=7:3) to obtain 5-methoxy-3-indoleacetic acid methyl ester (58.6 mg, yield: 55.2%); $^1$H NMR (400 MHz, CDCl$_3$): δ 7.22 (1H, d, J=8.8), 7.11 (d, J=2.3 Hz, 1H), 7.05 (d, J=1.3 Hz, 1H), 6.93 (dd, J=8.8, 2.3 Hz, 1H), 3.70 (s, 3H), 3.85 (s, 3H), 3.74 (s, 2H); $^{13}$C NMR (100 MHz, CDCl$_3$): δ 172.5, 154.2, 131.2, 127.6, 123.8, 112.5, 111.9, 108.1, 100.6, 55.9, 51.9, 31.2; IR (neat): 3403, 2951, 1729, 1486, 1213, 1154 cm$^{-1}$; EI-MS m/z [M]$^+$219, 160; HREI-MS found m/z 219.0886 [M]$^+$, calcd for 219.0895 (C$_{12}$H$_{13}$NO$_3$).

5-Methoxy-3-indoleacetic Acid (Compound #36)

Synthesis of Compound #36

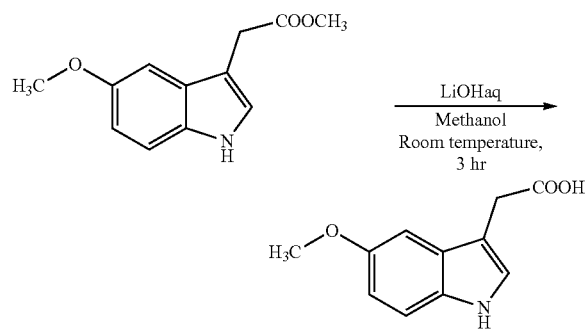

5-Methoxy-3-indoleacetic acid methyl ester (60.0 mg, 0.27 mmol) was dissolved in methanol (2 ml). To the solution, lithium hydroxide (19.7 mg, 0.82 mmol) was added, and the mixture was stirred at room temperature for 3 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=9:1) to obtain 5-methoxy-3-indoleacetic acid (compound #36) (15.3 mg, yield: 27.2%); Melting point: 147.0 to 149.8° C.; $^1$H NMR (400 MHz, CDCl$_3$): δ 7.28 (d, J=8.8 Hz, 1H), 7.26 (s, 1H), 7.11 (d, J=2.3 Hz, 1H), 6.77 (dd, J=8.8, 2.3 Hz, 1H), 3.80 (s, 3H), 3.71 (s, 1H); $^{13}$C NMR (100 MHz, CDCl$_3$): δ 173.3, 154.8, 132.6, 128.9, 125.2, 112.7, 112.4, 108.8, 101.4, 55.8, 31.5; IR (neat): 3359, 2996, 2851, 1705, 1456, 1137 cm$^{-1}$; EI-MS m/z [M]$^+$205 (75%), 160; HREI-MS found m/z 205.0737 [M]$^+$, calcd for 205.0739 (C$_{11}$H$_{11}$NO$_3$).

Synthesis of Compound #37

5-Ethoxy-3-indoleacetic Acid Methyl Ester

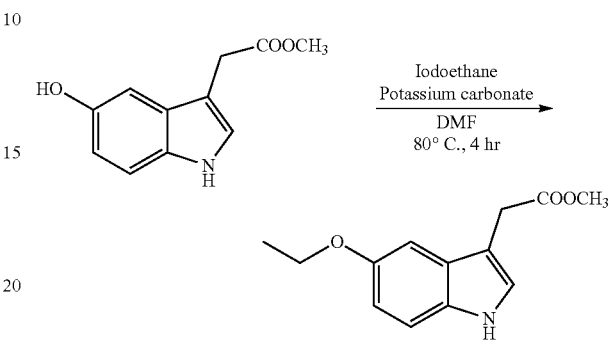

5-Hydroxy-3-indoleacetic acid methyl ester (109.0 mg, 0.53 mmol) was dissolved in N,N-dimethylformamide (2 ml). To this solution, iodoethane (248.74 mg, 1.60 mmol) was added dropwise, then potassium carbonate (220.5 mg, 1.60 mmol) put aside in another container was added, and the mixture was stirred at room temperature for 2 hours and stirred at 80° C. for 4 hours. After the reaction was confirmed by TLC to be complete, a 10% aqueous sodium bicarbonate solution (20 ml) was added thereto, followed by extraction with ethyl acetate (50 ml). The organic layer was washed twice with saturated saline and dehydrated over anhydrous sodium sulfate. The solvent was distilled off under reduced pressure, and then, the residue was purified using silica gel column chromatography (hexane:ethyl acetate=7:3) to obtain 5-ethoxy-3-indoleacetic acid methyl ester (100.7 mg, yield: 81.2%); $^1$H NMR (400 MHz, CDCl$_3$): δ 7.86 (q, J=7.0 Hz, 2H), 7.23 (d, J=8.8 Hz, 1H), 7.05 (d, J=2.3 Hz, 1H), 7.12 (d, J=2.0 Hz, 1H), 6.87 (dd, J=8.8, 2.3 Hz, 1H), 3.75 (s, 2H), 3.70 (s, 3H), 1.45 (t, J=7.0 Hz, 3H); $^{13}$C NMR (100 MHz, CDCl$_3$): δ 172.5, 153.4, 131.2, 127.6, 123.7, 113.0, 111.8, 108.1, 101.8, 64.2, 52.0, 31.2, 15.0; IR (neat): 3404, 2978, 1729, 1474, 1211, 1154 cm$^{-1}$; HREI-MS found m/z 233.1034 [M]$^+$, calcd for 233.1052 (C$_{13}$H$_{15}$NO$_3$).

5-Ethoxy-3-indoleacetic Acid (Compound #37)

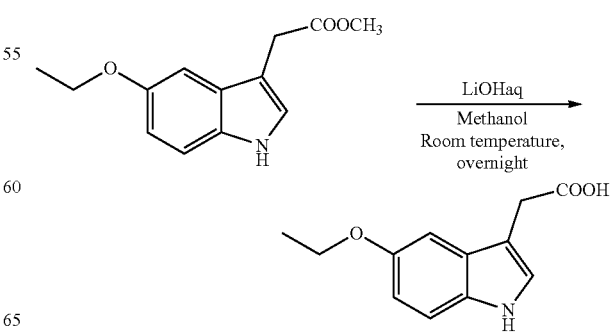

5-Ethoxy-3-indoleacetic acid methyl ester (90.2 mg, 0.27 mmol) was dissolved in methanol (4 ml). To the solution, lithium hydroxide (13.9 mg, 0.58 mmol) was added, and the mixture was stirred overnight at room temperature. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=9:1) to obtain 5-ethoxy-3-indoleacetic acid (compound #37) (83.8 mg, yield: 98.9%); Melting point: 86.0 to 92.7° C.; $^1$H NMR (400 MHz, CDCl$_3$): δ 7.23 (d, J=8.8 Hz, 1H), 7.12 (d, J=1.9 Hz, 1H), 7.04 (d, J=2.3 Hz, 1H), 6.86 (dd, J=8.8, 2.3 Hz, 1H), 4.09 (q, J=7.0 Hz, 2H), 3.80 (s, 2H), 1.42 (t, J=7.0 Hz, 3H); $^{13}$C NMR (100 MHz, CDCl$_3$): δ 177.4, 153.5, 131.2, 127.5, 124.0, 113.2, 111.9, 107.7, 101.7, 64.2, 31.1, 15.0; IR (neat): 3354, 3066, 2930, 1695, 1457, 1112 cm$^{-1}$; EI-MS m/z [M]$^+$219, 205 (40%), 190, 174, 162 (70%), 160 (50%); HREI-MS found m/z 219.0886 [M]$^+$, calcd for 219.0895 (C$_{12}$H$_{13}$NO$_3$).

Synthesis of Compound #38

5-(1-Propoxy)-3-indoleacetic Acid Methyl Ester

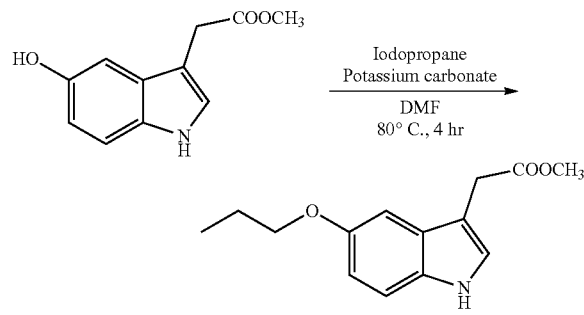

5-Hydroxy-3-indoleacetic acid methyl ester (108.4 mg, 0.53 mmol) was dissolved in N,N-dimethylformamide (2 ml). To this solution, iodopropane was added dropwise, then potassium carbonate (219.3 mg, 1.59 mmol) put aside in another container was added, and the mixture was stirred at room temperature for 2 hours and stirred at 80° C. for 4 hours. After the reaction was confirmed by TLC to be complete, a 10% aqueous sodium bicarbonate solution (20 ml) was added thereto, followed by extraction with ethyl acetate (50 ml). The organic layer was washed twice with saturated saline and dehydrated over anhydrous sodium sulfate. The solvent was distilled off under reduced pressure, and then, the residue was purified using silica gel column chromatography (hexane:ethyl acetate=7:3) to obtain 5-(1-propoxy)-3-indoleacetic acid methyl ester (78.6 mg, yield: 60.1%); Melting point: 38.6 to 41.0° C.; H NMR (400 MHz, CDCl$_3$): δ 7.21 (d, J=8.8 Hz, 1H), 7.10 (d, J=2.3 Hz, 1H), 7.05 (d, J=2.3 Hz, 1H), 6.86 (dd, J=8.8, 2.3 Hz, 1H), 4.01 (t, J=6.7 Hz, 2H), 3.74 (s, 2H), 3.70 (s, 3H), 1.82 (m, 2H), 1.07 (t, J=6.7 Hz, 3H); $^{13}$C NMR (100 MHz, CDCl$_3$): δ 172.5, 153.6, 131.2, 127.6, 123.7, 113.0, 111.8, 108.0, 101.7, 70.4, 52.0, 31.2, 22.8, 10.6; IR (neat): 3355, 3061, 2961, 1695, 1457, 1126 cm$^{-1}$; EI-MS m/z [M]$^+$247 (70%), 188 (30%), 149, 131 (75%); HREI-MS found m/z 247.1225 [M]$^+$, calcd for 247.1208 (C$_{14}$H$_{17}$NO$_3$).

5-(1-Propoxy)-3-indoleacetic Acid (Compound #38)

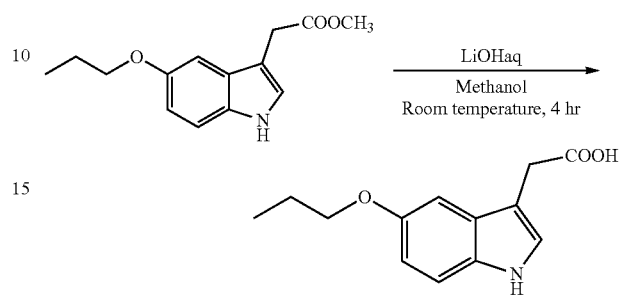

5-(1-Propoxy)-3-indoleacetic acid methyl ester (64.3 mg, 0.26 mmol) was dissolved in methanol (2 ml). To the solution, lithium hydroxide (9.35 mg, 0.39 mmol) was added, and the mixture was stirred at room temperature for 4 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=9:1) to obtain 5-(1-propoxy)-3-indoleacetic acid (compound #38) (59.3 mg, yield: 97.7%); Melting point: 133.6 to 136.8° C.; $^1$H NMR (400 MHz, CDCl$_3$): δ 7.23 (d, J=8.8 Hz, 1H), 7.13 (s, 1H), 7.04 (d, J=2.2 Hz, 1H), 6.87 (dd, J=8.1, 2.2 Hz, 1H), 3.96 (t, J=6.6 Hz, 2H), 3.76 (s, 3H), 1.82 (m, 2H), 1.05 (t, J=7.4 Hz, 3H); $^{13}$C NMR (100 MHz, CDCl$_3$): δ 177.4, 153.7, 131.2, 127.5, 123.9, 113.2, 111.9, 107.5, 101.7, 70.4, 31.0, 22.8, 10.6, 10.6; IR (neat): 3407, 2954, 1728, 1456, 1213, 1160 cm$^{-1}$; EI-MS m/z [M]$^+$233, 191 (50%); HREI-MS found m/z 233.1043 [M]$^+$, calcd for 233.1052 (C$_{12}$H$_{15}$NO$_3$).

Synthesis of Compound #39

5-(1-Butoxy)-3-indoleacetic Acid Methyl Ester

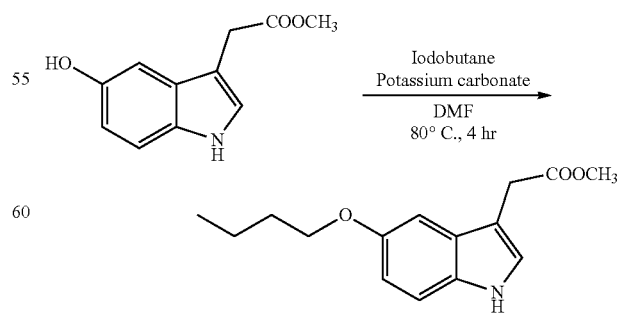

5-Hydroxy-3-indoleacetic acid methyl ester (108.4 mg, 0.53 mmol) was dissolved in N,N-dimethylformamide (2 ml). To this solution, iodobutane was added dropwise, then potassium carbonate (184.2 mg, 1.33 mmol) put aside in another container was added, and the mixture was stirred at 80° C. for 4 hours. After the reaction was confirmed by TLC to be complete, a 10% aqueous sodium bicarbonate solution (20 ml) was added thereto, followed by extraction with ethyl acetate (50 ml). The organic layer was washed twice with saturated saline and dehydrated over anhydrous sodium sulfate. The solvent was distilled off under reduced pressure, and then, the residue was purified using silica gel column chromatography (hexane:ethyl acetate=7:3) to obtain 5-(1-butoxy)-3-indoleacetic acid methyl ester (140.2 mg, yield: 80.5%); $^1$H NMR (400 MHz, CDCl$_3$): δ 7.21 (d, J=7.2 Hz, 1H), 7.10 (d, J=2.3 Hz, 1H), 7.05 (d, J=2.3 Hz, 1H), 6.86 (dd, J=8.8, 2.3 Hz, 1H), 4.01 (t, J=6.5 Hz, 2H), 3.74 (s, 2H), 3.70 (s, 3H), 1.82 (m, 2H), 1.52 (m, 2H), 0.98 (t, J=7.4 Hz, 3H); $^{13}$C NMR (100 MHz, CDCl$_3$): δ 172.5, 153.6, 131.2, 127.6, 123.7, 113.0, 111.8, 108.0, 101.7, 68.5, 51.9, 31.9, 31.2, 19.3, 13.9; IR (neat): 3355, 2957, 1694, 1459, 1127 cm$^{-1}$; HREI-MS found m/z 261.137 [M]$^+$, calcd for 261.1365 (C$_{15}$H$_{19}$NO$_3$).

5-(1-Butoxy)-3-indoleacetic Acid (Compound #39)

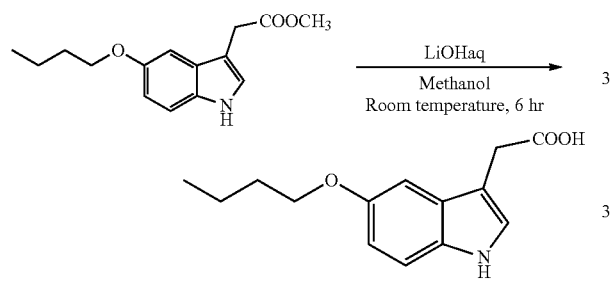

5-(1-Butoxy)-3-indoleacetic acid methyl ester (91.0 mg, 0.35 mmol) was dissolved in methanol (2 ml). To the solution, lithium hydroxide (12.5 mg, 0.52 mmol) was added, and the mixture was stirred at room temperature for 6 hours. After the reaction was confirmed by TLC to be complete, the reaction solution was rendered acidic (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with saturated saline and dehydrated over anhydrous sodium sulfate. The solvent was distilled off under reduced pressure, and then, the residue was purified using silica gel column chromatography (chloroform:methanol=9:1) to obtain 5-(1-butoxy)-3-indoleacetic acid (compound #39) (43.8 mg, yield: 51.0%); Melting point: 137.8 to 141.1° C.; H NMR (400 MHz, CDCl$_3$): δ 7.24 (d, J=8.8 Hz, 1H), 7.14 (s, 1H), 7.04 (d, J=2.0 Hz, 1H), 6.87 (dd, J=8.8, 2.0 Hz, 1H), 4.01 (t, J=6.6 Hz, 2H), 3.76 (s, 2H), 1.78 (m, 2H), 1.05 (t, J=7.4 Hz, 3H); $^{13}$C NMR (100 MHz, CDCl$_3$): δ 173.3, 153.8, 131.2, 123.9, 113.2, 111.6, 107.5, 101.6, 31.6, 29.7, 19.3, 13.9; IR (neat): 3407, 2954, 1728, 1456, 1213, 1160 cm$^{-1}$; EI-MS m/z [M]$^+$247, 191 (60%); HREI-MS found m/z 247.1189 [M]$^+$, calcd for 247.1208 (C$_{14}$H$_{17}$NO$_3$).

Synthesis of Compound of Formula (1)

Synthesis of 4-(2,4-difluorophenyl)-2-(6-fluoro-1H-indol-3-yl)-4-oxo-butanoic Acid (Compound (4-1))

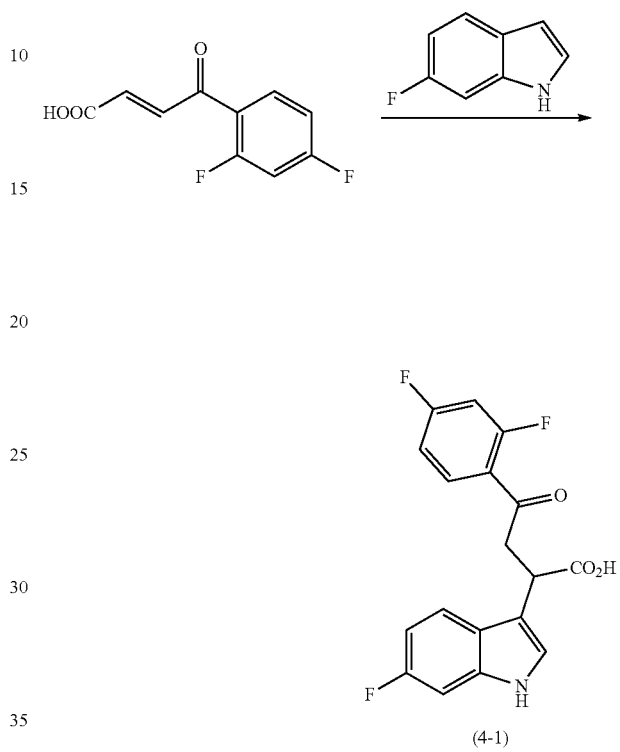

(4-1)

In a 50-mL round-bottomed flask, 6-fluoroindole (485 mg, 3.59 mmol) was added and (E)-4-(2,4-difluorophenyl)-4-oxo-2-butenoic acid (508 mg, 2.39 mmol) was dissolved in benzene (20 mL) and the mixture was heated at 80° C. for 7 hours to reflux. Distilled water (50 mL) was added to the reaction mixture, and extracted with ethyl acetate (50 mL). The organic layer was washed with saturated saline (30 mL), dried over anhydrous sodium sulfate, and concentrated under reduced pressure. The product obtained by the concentration was purified using silica gel column chromatography (hexane:acetone=2:1) to obtain 4-(2,4-Difluorophenyl)-2-(6-fluoro-1H-indol-3-yl)-4-oxo-butanoic acid (433 mg, yield: 52%) as a colorless crystal.

Melting point: 210 to 214° C.;

$^1$H-NMR (400 MHz, CDCl$_3$) δ 10.31 (s, 1H), 8.01 (m, 1H), 7.47 (dd, J=8.8, 5.2, 1H), 7.34 (d, J=2.0, 2H), 7.12-7.20 (m, 3H), 6.92 (td, J=9.6, 2.4, 1H), 4.54 (dd, J=10.4, 4.0, 1H), 4.01 (ddd, J=18.8, 10.8, 3.2, 1H), 3.38 (td, J=18.8, 3.2, 1H); $^{13}$C-NMR (100 MHz, CDCl$_3$) δ 195.18, 174.85, 166.28 J$_{C-F}$ (dd, 254, 13 Hz), 163.42 J$_{C-F}$ (dd, 254, 13 Hz), 161.74, 159.4, 137.54 J$_{C-F}$ (d, 13 Hz), 133.47 J$_{C-F}$ (dd, 11, 3 Hz), 123. 35 J$_{C-F}$ (d, 4 Hz), 123. 02 J$_{C-F}$ (dd, 13, 4 Hz), 120.97 J$_{C-F}$ (d, 11 Hz), 113.51, 112.94 J$_{C-F}$ (dd, 10, 2 Hz), 108.27 J$_{C-F}$ (d, 24 Hz), 105.59 J$_{C-F}$ (t, 27 Hz), 98.27 J$_{C-F}$ (d, 26 Hz), 46.68 J$_{C-F}$ (d, 7 Hz), 38.47;

FAB-MS m/z=348 [M+H]$^+$

Synthesis of 4-(2,4-difluorophenyl)-2-(5-fluoro-1H-indol-3-yl)-4-oxo-butanoic Acid (Compound (3-1))

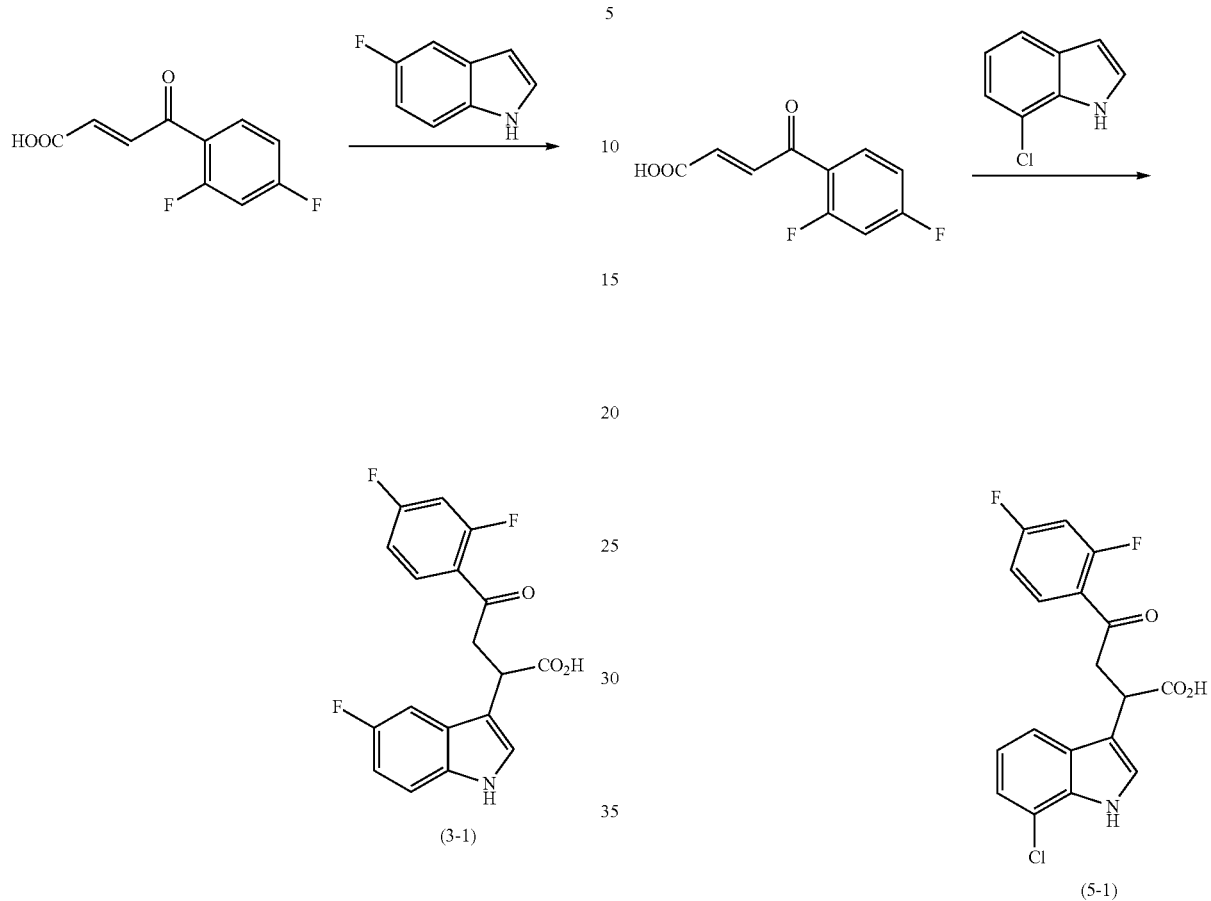

(3-1)

In a 50-mL round-bottomed flask, 5-fluoroindole (925 mg, 6.85 mmol) was added and (E)-4-(2,4-difluorophenyl)-4-oxo-2-butenoic acid (969 mg, 4.57 mmol) was dissolved in benzene (20 mL) and the mixture was heated at 80° C. for 11 hours to reflux. Distilled water (50 mL) was added to the reaction mixture, and extracted twice with ethyl acetate (50 mL). The organic layer was washed with saturated saline (30 mL), dried over anhydrous sodium sulfate, and concentrated under reduced pressure. The product obtained by the concentration was filtrated with a Hirsch funnel, and the residue was recrystallized from chloroform and ethyl acetate to obtain 4-(2,4-difluorophenyl)-2-(5-fluoro-1H-indol-3-yl)-4-oxo-butanoic acid (1122 mg, yield: 71%) as a colorless crystal.

Melting point: 207 to 208° C.;

$^1$H-NMR (400 MHz, acetone-$d_6$) δ10.34 (s, 1H), 8.02 (m, 1H), 7.47 (dd, J=10.4, 2.8, 1H), 7.39-7.43 (m, 2H), 7.13-7.21 (m, 2H), 6.93 (td, J=9.2, 2.8, 1H), 4.52 (dd, J=10.4, 3.6, 1H), 4.03 (ddd, 18.4, 10.8, 3.6, 1H), 3.40 (td, 18.4, 3.6, 1H); $^{13}$C-NMR (100 MHz, acetone-$d_6$) δ 195.17, 174.86, 166.52 $J_{C-F}$ (dd, 254, 13 Hz), 163.58 $J_{C-F}$ (dd, 254, 13 Hz), 159.52, 157.21, 134.25, 133.46 $J_{C-F}$ (dd, 11, 4 Hz), 127.66 $J_{C-F}$ (d, 11 Hz), 123.01 $J_{C-F}$ (dd, 10, 4 Hz), 113.42 $J_{C-F}$ (d, 5 Hz), 113.28 $J_{C-F}$ (d, 10 Hz), 113.51 $J_{C-F}$ (d, 21, 4 Hz), 110.56 $J_{C-F}$ (d, 27 Hz), 105.61 $J_{C-F}$ (t, 27 Hz), 104.65 $J_{C-F}$ (d, 24 Hz), 46.68 $J_{C-F}$ (d, 8 Hz), 38.48;

FAB-MS m/z=348 [M+H]$^+$

Synthesis of 2-(7-chloro-1H-indol-3-yl)-4-(2,4-difluorophenyl)-4-oxo-butanoic Acid (Compound(5-1))

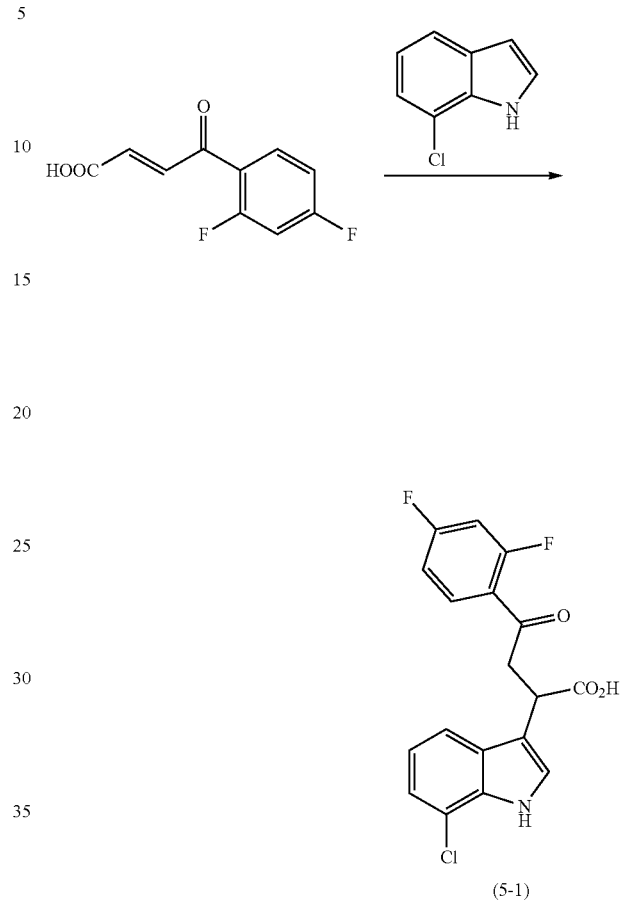

(5-1)

In a 50-mL round-bottomed flask, 7-chloroindole (1094 mg, 5.16 mmol) was added and (E)-4-(2,4-difluorophenyl)-4-oxo-2-butenoic acid (935 mg, 4.41 mmol) was dissolved in benzene (20 mL) and the mixture was heated at 80° C. for 10 hours to reflux. Distilled water (50 mL) was added to the reaction mixture, and extracted twice with ethyl acetate (50 mL). The organic layer was washed with saturated saline (30 mL), dried over anhydrous sodium sulfate, and concentrated under reduced pressure. The product obtained by the concentration was filtrated with a Hirsch funnel, and the residue was recrystallized from benzene and acetone to obtain 2-(7-chloro-1H-indol-3-yl)-4-(2,4-difluorophenyl)-4-oxo-butanoic acid (1017 mg, yield: 54%) as a colorless crystal.

Melting point: 225 to 227° C.;

$^1$H-NMR (400 MHz, acetone-$d_6$) δ10.55 (s, 1H), 8.01 (m, 1H), 7.75 (d, J=8.4, 1H), 7.45 (d, J=2.8, 1H), 7.06-7.14 (m, 4H), 7.08 (t, J=7.6, 1H), 4.57 (dd, J=10.4, 3.6, 1H), 4.03 (ddd, 18.4, 10.8, 3.6, 1H), 3.41 (td, 18.4, 3.6, 1H);

$^{13}$C-NMR (100 MHz, acetone-$d_6$) δ195.06, 74.67, 166.53, $J_{C-F}$ (dd, 252, 12 Hz), 163.63 $J_{C-F}$ (dd, 252, 12 Hz), 134. 45, 133.46 $J_{C-F}$ (dd, 11, 5 Hz), 129.25, 124.97, 122.98 $J_{C-F}$ (dd, 13, 4 Hz), 121.91, 120.84, 119.03, 117.22, 114.73, 112.99 $J_{C-F}$ (dd, 21, 3 Hz), 105.61 $J_{C-F}$ (t, 27 Hz), 46.71 $J_{C-F}$ (d, 8 Hz), 38.50;

FAB-MS m/z=364 [M+H]$^+$

101
Synthesis of 2-(5-chloro-1H-indol-3-yl)-4-(2,4-difluorophenyl)-4-oxo-butanoic Acid (Compound(3-2))

102
Synthesis of 2-(4-chloro-1H-indol-3-yl)-4-(2,4-difluorophenyl)-4-oxo-butanoic Acid (Compound(2-1))

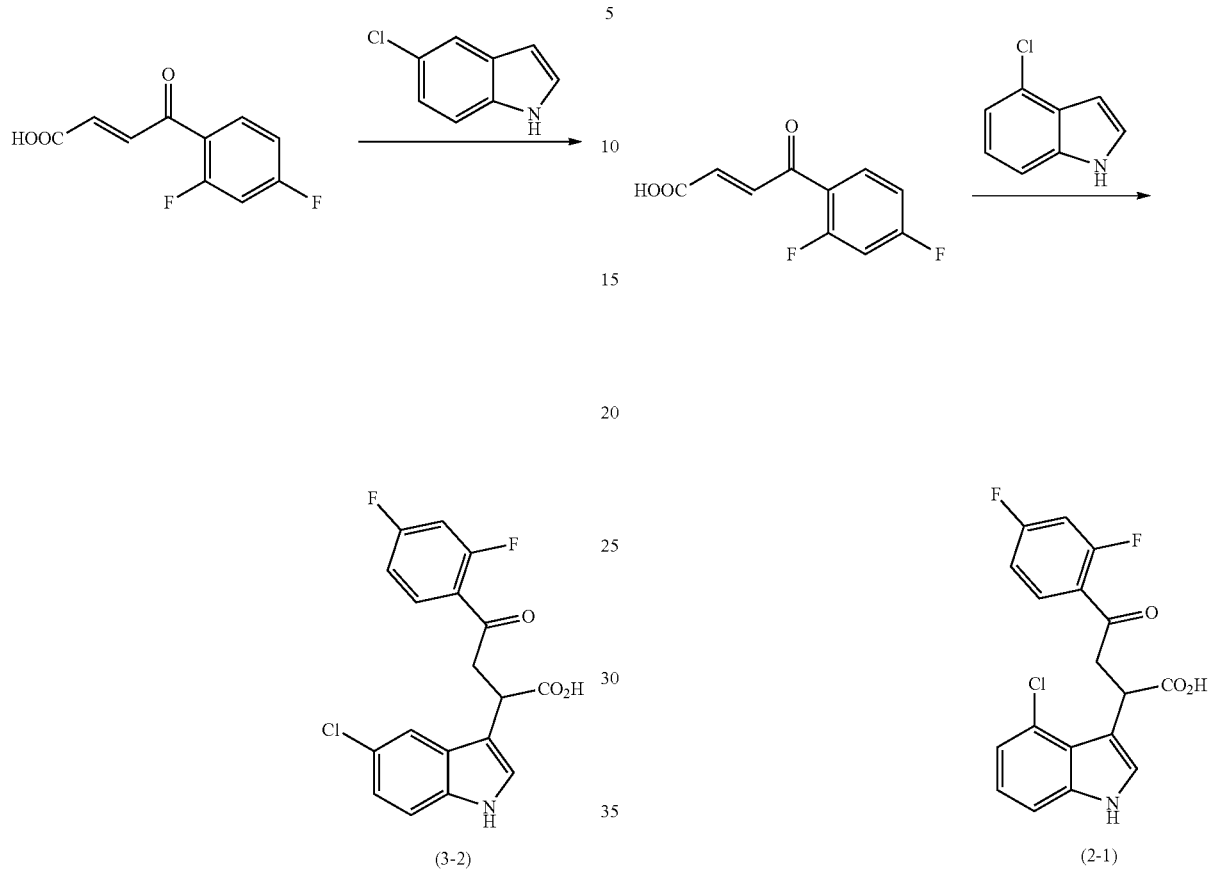

(3-2)

(2-1)

In a 50-mL round-bottomed flask, 5-chloroindole (1000 mg, 6.61 mmol) was added and (E)-4-(2,4-difluorophenyl)-4-oxo-2-butenoic acid (935 mg, 4.41 mmol) was dissolved in benzene (20 mL) and the mixture was heated at 80° C. for 7 hours to reflux. Distilled water (50 mL) was added to the reaction mixture, and extracted twice with ethyl acetate (50 mL). The organic layer was washed twice with saturated saline (30 mL), dried over anhydrous sodium sulfate, and concentrated under reduced pressure. The product obtained by the concentration was filtrated with a Hirsch funnel, and the residue was recrystallized from benzene and acetone to obtain 2-(5-chloro-1H-indol-3-yl)-4-(2,4-difluorophenyl)-4-oxo-butanoic acid (1084 mg, yield: 63%) as a light yellow crystal.

Melting point: 236 to 239° C.;

$^1$H-NMR (400 MHz, acetone-$d_6$) δ10.45 (s, 1H), 8.02 (q, J=8.3, 1H), 7.80 (d, J=1.6, 1H), 7.44 (m, 2H), 7.11-7.22 (m, 3H), 4.54 (dd, J=10.4, 3.8, 1H), 4.01 (ddd, J=18.7, 10.7, 3.2, 1H), 3.41 (td, J=18.7, 3.2, 1H);

$^{13}$C-NMR (100 MHz, acetone-$d_6$) δ195.10, 174.76, 166.52 $J_{C-F}$ (dd, 253, 12 Hz), 163.62 $J_{C-F}$ (dd, 253, 12 Hz), 136.06, 133.44 $J_{C-F}$ (dd, 12, 4 Hz), 128.47, 125.62, 122.96 $J_{C-F}$ (dd, 13, 4 Hz), 122.48, 119.33, 113.77, 113.12, 112.96 $J_{C-F}$ (dd, 22, 3 Hz), 105.61 $J_{C-F}$ (t, 27 Hz), 46.72 $J_{C-F}$ (d, 8 Hz), 38.35;

FAB-MS m/z=364 [M+H]$^+$

In a 50-mL round-bottomed flask, 4-chloroindole (903 mg, 5.98 mmol) was added and (E)-4-(2,4-difluorophenyl)-4-oxo-2-butenoic acid (842 mg, 3.97 mmol) was dissolved in benzene (20 mL) and the mixture was heated at 80° C. for 7 hours to reflux. Distilled water (50 mL) was added to the reaction mixture, and extracted with ethyl acetate (50 mL). The organic layer was washed with saturated saline (30 mL), dried over anhydrous sodium sulfate, and concentrated under reduced pressure. The product was purified using silica gel column chromatography (chloroform:methanol=9:1), and the residue was then recrystallized from benzene and acetone to obtain 2-(4-chloro-1H-indol-3-yl)-4-(2,4-difluorophenyl)-4-oxo-butanoic acid (602 mg, yield: 51%) as a colorless crystal.

Melting point: 203 to 204° C.;

$^1$H-NMR (400 MHz, acetone-$d_6$) δ10.24 (s, 1H), 8.01 (m, 1H), 7.77 (d, J=8.4, 1H), 7.42 (d, J=8.0, 1H), 7.21~7.03 (m, 4H), 4.57 (dd, J=10.8, 3.6, 1H), 4.03 (ddd 18.8, 10.8, 3.2, 1H), 3.38 (td, 18.8, 3.2, 1H);

$^{13}$C-NMR (100 MHz, acetone-$d_6$) δ195.28, 174.97, 166.55 $J_{C-F}$ (dd, 254, 12 Hz), 163.62 $J_{C-F}$ (dd, 254, 12 Hz), 137.646, 137.49, 133.46 $J_{C-F}$ (dd, 11, 4 Hz), 127.37, 123.70, 123.54, 123.05 $J_{C-F}$ (dd, 13, 4 Hz), 122.39, 119.88, 119.79, 112.95 $J_{C-F}$ (dd, 22, 4 Hz), 105.58 $J_{C-F}$ (t, 26 Hz), 46.95 $J_{C-F}$ (d, 8 Hz), 38.47;

FAB-MS m/z=364 [M+H]$^+$

Synthesis of 4-(2,4-difluorophenyl)-2-(5-methyl-1H-indol-3-yl)-4-oxo-butanoic Acid (Compound(3-3))

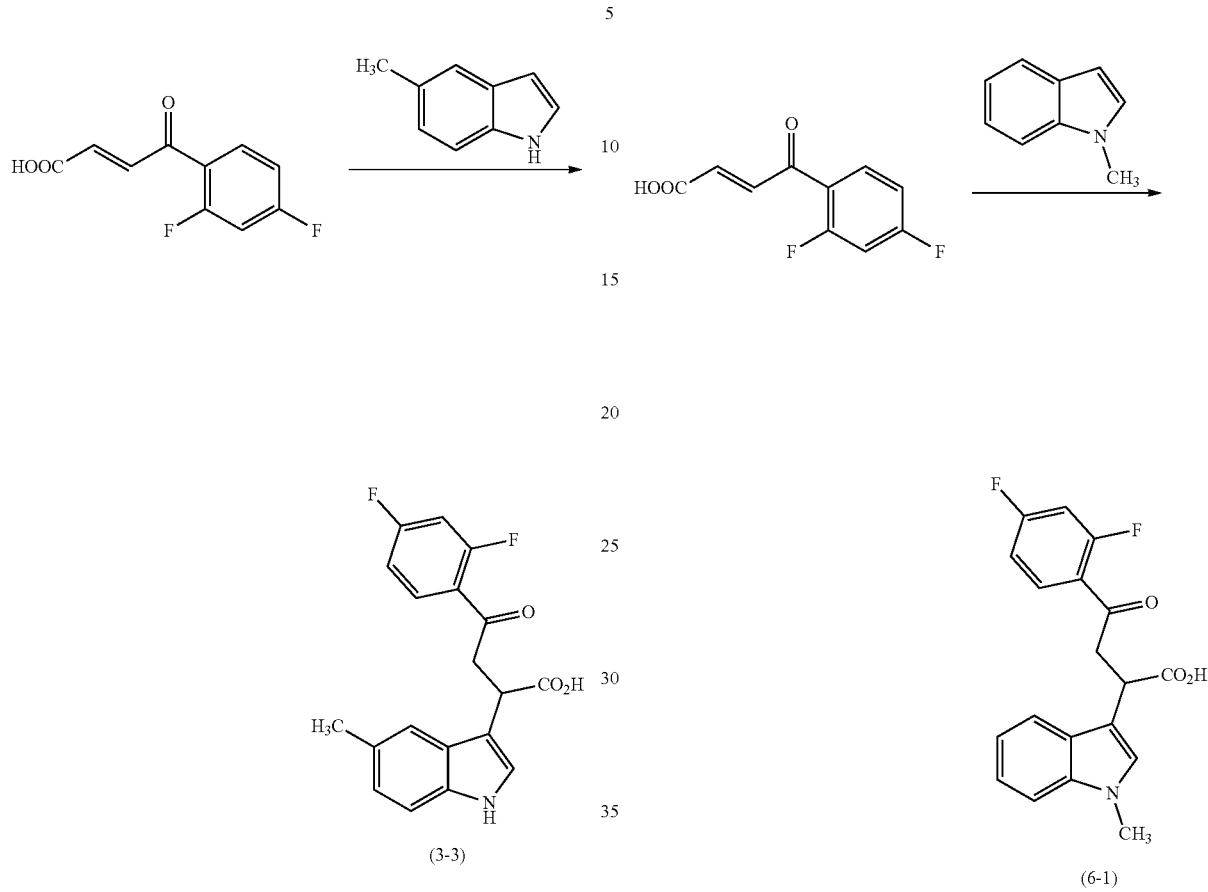

(3-3)

Synthesis of 4-(2,4-difluorophenyl)-2-(1-methyl-1H-indol-3-yl)-4-oxo-butanoic Acid (Compound(6-1))

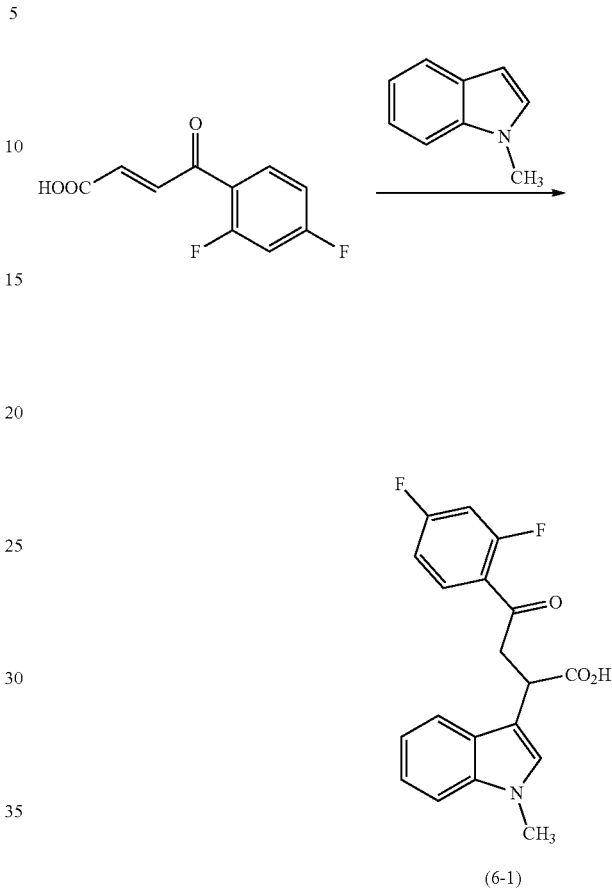

(6-1)

In a 50-mL round-bottomed flask, 5-methylindole (171 mg, 1.31 mmol) was added and (E)-4-(2,4-difluorophenyl)-4-oxo-2-butenoic acid (185 mg, 0.87 mmol) was dissolved in benzene (20 mL) and the mixture was heated at 80° C. for 7 hours to reflux. Distilled water (50 mL) was added to the reaction mixture, and extracted with ethyl acetate (50 mL). The organic layer was washed with saturated saline (30 mL), dried over anhydrous sodium sulfate, and concentrated under reduced pressure. The product obtained by the concentration was filtrated with a Hirsch funnel, and the residue was recrystallized from benzene and acetone to obtain 4-(2,4-difluorophenyl)-2-(5-methyl-1H-indol-3-yl)-4-oxo-butanoic acid (200 mg, yield: 67%) as a colorless crystal.

Melting point: 200 to 202° C.;

$^1$H-NMR (400 MHz, acetone-$d_6$) δ10.10 (s, 1H), 8.01 (m, 1H), 7.54 (s, 1H), 7.20-7.31 (m, 2H), 7.13-7.20 (m, 1H), 7.96 (d, J=6.8, 1H), 4.53 (dd, J=10.6, 3.6, 1H), 4.01 (ddd 18.8, 10.6, 3.2, 1H), 3.36 (td, 18.8, 3.2, 1H), 2.40 (s, 3H);

$^{13}$C-NMR (100 MHz, acetone-$d_6$) δ195.33, 175.08, 166.54 $J_{C-F}$ (dd, 254, 12 Hz), 163.49 $J_{C-F}$ (dd, 254, 12 Hz), 136.01, 133.45 $J_{C-F}$ (dd, 11, 4 Hz), 128.59, 127.63, 124.02, 123.72, 123.05 $J_{C-F}$ (dd, 13, 4 Hz), 119.43, 112.94 $J_{C-F}$ (dd, 22, 4 Hz), 112.74, 112.03, 105.59 $J_{C-F}$ (t, 26 Hz), 47.01 $J_{C-F}$ (d, 7 Hz), 38.45, 21.64;

FAB-MS m/z=344 [M+H]$^+$

In a 50-mL round-bottomed flask, 1-methylindole (2512 mg, 19.17 mmol) was added and (E)-4-(2,4-difluorophenyl)-4-oxo-2-butenoic acid (2710 mg, 12.78 mmol) was dissolved in benzene (20 mL) and the mixture was heated at 80° C. for 1 hour to reflux. Distilled water (50 mL) was added to the reaction mixture, and extracted twice with ethyl acetate (50 mL). The organic layer was washed twice with saturated saline (30 mL), dried over anhydrous sodium sulfate, and concentrated under reduced pressure. The product obtained by the concentration was filtrated with a Hirsch funnel, and the residue was recrystallized from benzene and acetone to obtain 4-(2,4-difluorophenyl)-2-(1-methyl-1H-indol-3-yl)-4-oxo-butanoic acid (3898 mg, yield: 89%) as a colorless crystal.

Melting point: 192 to 193° C.; $^1$H-NMR (400 MHz, acetone-$d_6$) δ 8.00 (m, 1H), 7.75 (d, J=7.6, 1H), 7.37 (d, J=8.4, 1H), 7.12-7.22 (m, 4H), 7.07 (t, J=7.6, 1H), 4.54 (dd, J=10.8, 3.6, 1H), 4.00 (ddd, 18.8, 10.4, 3.6, 1H), 3.79 (s, 3H), 3.36 (td, 18.8, 3.6, 1H);

$^{13}$C-NMR (100 MHz, acetone-$d_6$) δ195.22, 174.94, 166.52 $J_{C-F}$ (dd, 253, 13 Hz), 163.57 $J_{C-F}$ (dd, 253, 13 Hz), 138.08, 133.46 $J_{C-F}$ (dd, 11, 4 Hz), 128.00, 127.79, 123.03 $J_{C-F}$ (dd, 13, 4 Hz), 122.36, 120.07, 119.72, 112.94 $J_{C-F}$ (d, 22, 4 Hz), 112.33, 110.32, 105.60 $J_{C-F}$ (t, 27 Hz), 47.01 $J_{C-F}$ (d, 8 Hz), 38.36, 32.72;

FAB-MS m/z=344 [M+H]$^+$

Synthesis of 4-(2,4-difluorophenyl)-2-(7-methoxy-1H-indol-3-yl)-4-oxo-butanoic Acid (Compound(5-2))

Synthesis of 4-(2,4-difluorophenyl)-2-(5-methoxy-1H-indol-3-yl)-4-oxo-butanoic Acid (Compound(3-4))

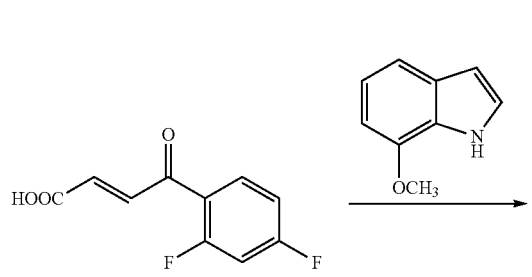

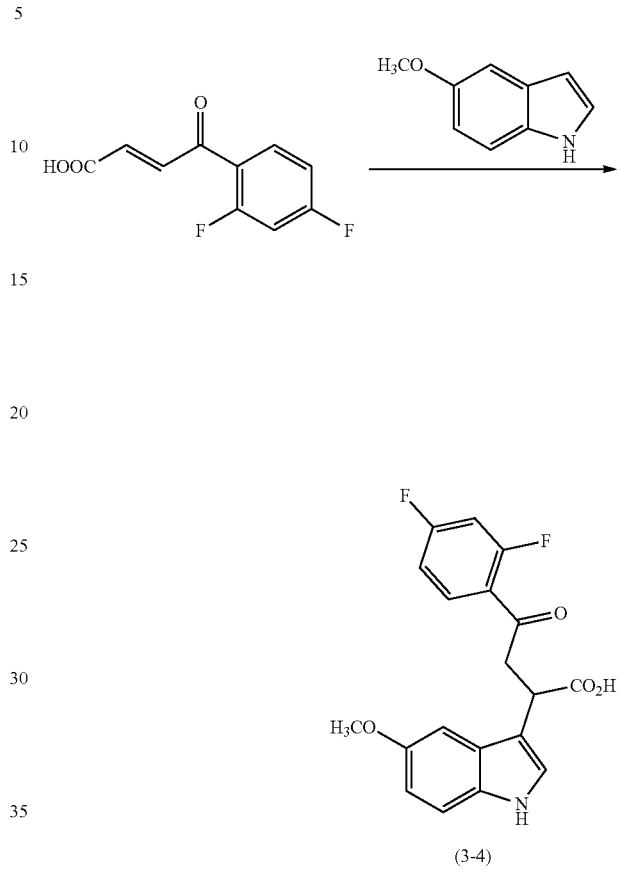

In a 50-mL round-bottomed flask, 7-methoxyindole (1083 mg, 7.36 mmol) was added and (E)-4-(2,4-difluorophenyl)-4-oxo-2-butenoic acid (1041 mg, 4.90 mmol) was dissolved in benzene (20 mL) and the mixture was heated at 80° C. for 14 hours to reflux. Distilled water (50 mL) was added to the reaction mixture, and extracted with ethyl acetate (50 mL). The organic layer was washed with saturated saline (30 mL), dried over anhydrous sodium sulfate, and concentrated under reduced pressure. The product obtained by the concentration was filtrated with a Hirsch funnel, and the residue was recrystallized from benzene and acetone to obtain 4-(2,4-difluorophenyl)-2-(7-methoxy-1H-indol-3-yl)-4-oxo-butanoic acid (1179 mg, yield: 67%) as a colorless crystal.

Melting point: 181 to 183° C.;

$^1$H-NMR (400 MHz, acetone-$d_6$) δ10.26 (s, 1H), 8.01 (m, 1H), 7.35 (d, J=8.0, 1H), 7.28 (d, J=2.8, 1H), 7.12-7.20 (m, 2H), 6.98 (t, J=7.8, 1H), 6.67 (d, J=7.8, 1H), 4.54 (dd, J=10.8, 3.6, 1H), 4.03 (ddd 18.8, 10.6, 3.3, 1H), 3.92 (s, 3H), 3.36 (td, 18.6, 3.2, 1H);

$^{13}$C-NMR (100 MHz, acetone-$d_6$) δ1195.28, 174.98, 166.54 $J_{C-F}$ (dd, 252, 12 Hz), 163.48 $J_{C-F}$ (dd, 252, 12 Hz), 147.35, 133.44 $J_{C-F}$ (dd, 11, 4 Hz), 128.81, 127.83, 123.22, 123.05 $J_{C-F}$ (dd, 13, 4 Hz), 120.43, 113.76, 112.94 $J_{C-F}$ (dd, 22, 4 Hz), 112.7, 105.59 $J_{C-F}$ (t, 27 Hz), 102.52, 55.52, 46.97 $J_{C-F}$ (d, 8 Hz), 38.59;

FAB-MS m/z=360 [M+H]$^+$

In a 50-mL round-bottomed flask, 5-methoxyindole (1166 mg, 7.93 mmol) was added and (E)-4-(2,4-difluorophenyl)-4-oxo-2-butenoic acid was dissolved in benzene (20 mL) and the mixture was heated at 80° C. for 10 hours to reflux. Distilled water (50 mL) was added to the reaction mixture, and extracted twice with ethyl acetate (50 mL). The organic layer was washed twice with saturated saline (30 mL), and dried over anhydrous sodium sulfate, and concentrated under reduced pressure. The product obtained by the concentration was filtrated with a Hirsch funnel, and the residue was recrystallized from benzene and acetone following by recrystallizing from chloroform to obtain 4-(2,4-difluorophenyl)-2-(5-methoxy-1H-indol-3-yl)-4-oxo-butanoic acid (1478 mg, yield: 75%) as a colorless crystal.

Melting point: 205 to 206° C.;

$^1$H-NMR (400 MHz, acetone-$d_6$) δ10.09 (s, 1H), 8.02 (m, 1H), 7.27-7.31 (m, 3H), 7.13-7.20 (m, 2H), 6.79 (dd, J=8.8, 2.4, 1H), 4.52 (dd, J=10.8, 3.6, 1H), 4.00 (ddd, 18.8, 10.4, 3.4, 1H), 3.80 (s, 3H), 3.38 (td, 18.6, 3.4, 1H;

$^{13}$C-NMR (100 MHz, acetone-$d_6$) δ195.35, 175.03, 166.53, $J_{C-F}$ (dd, 253, 12 Hz), 163.61 $J_{C-F}$ (dd, 253, 12 Hz), 154.84, 133.45 $J_{C-F}$ (dd, 11, 4 Hz), 132.72, 127.78, 124.22, 123.04 $J_{C-F}$ (dd, 12, 4 Hz), 112.95 $J_{C-F}$ (dd, 22, 4 Hz), 112.96, 112.68, 105.61 $J_{C-F}$ (t, 26 Hz), 101.58, 55.79, 46.9 $J_{C-F}$ (d, 8 Hz), 38.67;

FAB-MS m/z=360 [M+H]$^+$

107

Synthesis of 2-(6-benzyloxy-1H-indol-3-yl)-4-(2,4-difluorophenyl)-4-oxo-butanoic Acid (Compound(4-2))

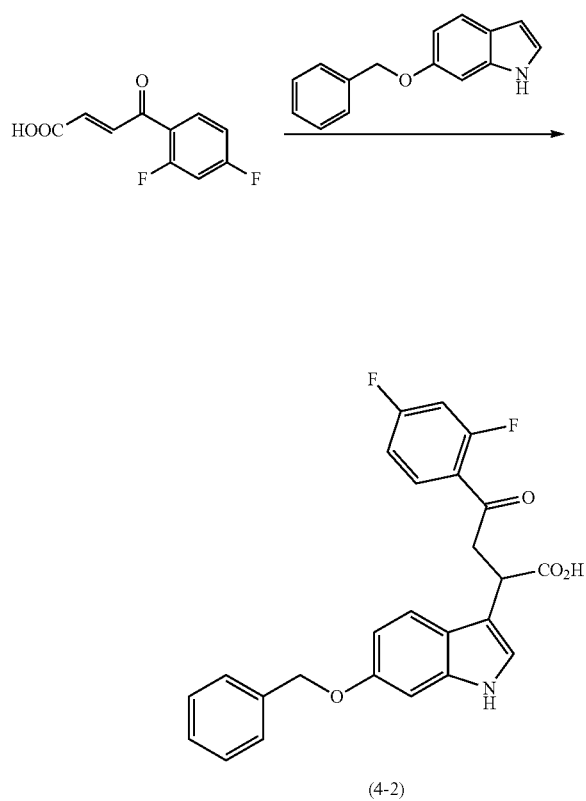

(4-2)

In a 50-mL round-bottomed flask, 6-benzyloxyindole (1255 mg, 5.62 mmol) was added and (E)-4-(2,4-difluorophenyl)-4-oxo-2-butenoic acid (795 mg, 3.74 mmol) was dissolved in benzene (20 mL) and the mixture was heated at 80° C. for 9 hours to reflux. Distilled water (50 mL) was added to the reaction mixture, and extracted with ethyl acetate (50 mL). The organic layer was washed with saturated saline (30 mL), dried over anhydrous sodium sulfate, and concentrated under reduced pressure. The product obtained by the concentration was filtrated with a Hirsch funnel, and the residue was recrystallized from chloroform to obtain 2-(6-benzyloxy-1H-indol-3-yl)-4-(2,4-difluorophenyl)-4-oxo-butanoic acid (531 mg, yield: 33%) as a light yellow crystal.

Melting point: 177 to 178° C.;

$^1$H-NMR (400 MHz, acetone-$d_6$) δ 10.0 4 (s, 1H), 8.01 (m, 1H), 7.65 (d, J=8.8, 1H), 7.48 (d, J=7.6, 2H), 7.38 (t, J=7.2, 2H), 7.31 (m, 1H), 7.13-7.20 (m, 3H), 7.03 (d, J=2.0, 1H), 6.83 (dd, J=8.4, 2.0, 1H), 4.51 (dd, J=10.4, 3.6, 1H), 4.01 (ddd, 18.1, 10.4, 3.3, 1H), 3.36 (td, 18.1, 3.3, 1H);

$^{13}$C-NMR (100 MHz, acetone-$d_6$) δ195.29, 175.00, 166.54 $J_{C-F}$ (dd, 254, 12 Hz), 163.52 $J_{C-F}$ (dd, 254, 12 Hz), 156.33, 138.85, 138.45, 133.45, $J_{C-F}$ (dd, 11, 4 Hz), 129.17, 128.37, 128.23, 123.01 $J_{C-F}$ (dd, 13, 4 Hz), 122.49, 121.97, 120.54, 113.24, 113.06 $J_{C-F}$ (dd, 21, 4 Hz), 110.73, 105.59 $J_{C-F}$ (t, 27 Hz), 96.89, 70.70, 46.94 $J_{C-F}$ (d, 8 Hz), 38.57;

FAB-MS m/z=436 [M+H]$^+$

108

Reference Example 1

(E)-4-(2,4-Difluorophenyl)-4-oxo-2-butenoic Acid

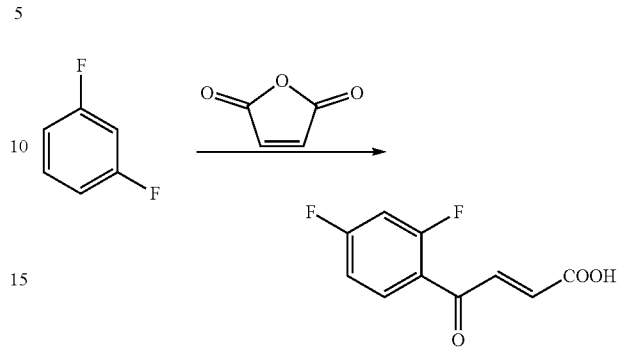

(E)-4-(2,4-Difluorophenyl)-4-oxo-2-butenoic acid which is used for the synthesize of the present compounds #1 to 10 was synthesized as follows. Specifically, in a 100-mL round-bottomed flask, 1,3-difluorobenzene (1300 mg, 11.39 mmol) and maleic anhydride (894 mg, 9.12 mmol) was added and dissolved in dichloromethane (40 mL) and stirred by a stirrer machine. While stirring, to the solution, anhydrous aluminum chloride (2279 mg, 17.09 mmol) were added little by little, and the mixture was stirred at room temperature for 6 hours. The reaction solution in the round-bottomed flask was added into iced water (100 mL) to terminate the reaction. Thereafter, the water layer was extracted with ethyl acetate (150 mL), and the organic layer was extracted with saturated saline (100 mL) for 2 times Thereafter, the organic layer was dried over anhydrous sodium sulfate, and then concentrated under reduced pressure to obtain a solid. The solid was purified by recrystallization from benzene and a little amount of acetone to obtain (E)-4-(2,4-difluorophenyl)-4-oxo-2-butenoic acid as a crystal with light yellow color by yield 48%.

Melting point: 136.0 to 139.0° C.;

$^1$H-NMR (400 MHz, acetone-$d_6$) δ 7.98 (m, 1H), 7.72 (dd, J=15.6, 3.6, 1H), 7.20-7.28 (m, 2H), 6.75 (d, J=15.6, 2H);

$^{13}$C-NMR (100 MHz, acetone-$d_6$) δ187.13, 166.86 $J_{C-F}$ (dd, 254, 12 Hz), 166.35, 163.33 $J_{C-F}$ (dd, 254, 12 Hz), 139.95 $J_{C-F}$ (d, 7 Hz), 133.98 $J_{C-F}$ (dd, 66, 59 Hz), 132.91, 123.22 $J_{C-F}$ (d, 9 Hz), 113.33 $J_{C-F}$ (dd, 22, 3 Hz), 105.76, $J_{C-F}$ (t, 22 Hz)

Example 2

2. Confirmation that the Compound Group of the Present Invention has an Effect of Enhancing Fertilization Function of a Mammal Sperm The effect of enhancing fertilization function of a mammal sperm was confirmed by a method given below using the compound group of the present invention (compound #5) synthesized in Example 1. Sperm preculture and semination were performed under conditions of 5% $CO_2$/20% $O_2$ and 37° C.

[Method]

[1] Pregnant mare serum gonadotropin (PMSG) was intraperitoneally administered to female C57/B6 mice. Multiple ovulation was induced with human chorionic gonadotropin (hCG) 48 hours after PMSG administration. The mice were euthanized 5 to 17 hours after hCG administration, and their fallopian tubes were recovered.

[2] Male C57/B6 mice were euthanized, and their epididymal tails were then removed and recovered.

[3] Droplets (drops) consisting of 100 μL each of 4 types of culture media (culture medium for semination [TYH culture medium, manufactured by LSI Medience Corp.] containing 0.0001% DMSO, TYH culture medium containing 1 μM compound #5, TYH culture medium containing 10 μM FCCP (carbonyl cyanide-p-trifluoromethoxyphenylhydrazone), and TYH culture medium containing 10 μM FCCP and 1 μM compound #5) were prepared and covered with mineral oil (manufactured by Sigma-Aldrich Corp.). The recovered epididymal tails were transferred into the mineral oil, and the epididymal ducts were damaged with a 1 mL syringe for tuberculin with a 26 G needle (manufactured by Nipro Corp.) while held with tweezers. The obtained sperm masses were transferred to the 4 types of culture media in the mineral oil and cultured before semination (precultured) for 1 hour.

[4] 3 μL each of the sperms precultured in the 4 types of culture media was transferred into 200 μL of drops of TYH culture medium containing a cumulus oocyte complex (COC) using a micropipette (manufactured by Eppendorf AG, Germany) and covered with mineral oil (manufactured by Sigma-Aldrich Corp.), followed by semination.

[5] The presence or absence of a two-cell egg was observed 24 to 28 hours after semination. When the two-cell egg was observed, fertilization was evaluated as being successful and the fertilization rate was measured.

[Results]

Semination using sperms precultured in TYH culture medium containing the solvent DMSO for compound #5, i.e., a culture medium free from compound #5, had a fertilization rate of 40%, whereas semination using sperms precultured in a culture medium containing compound #5 had a fertilization rate of 100% (see Table 1).

The results indicate that the compound group of the present invention (compound #5) has an effect of activating (enhancing) fertilization function of sperms.

TABLE 1

| Culture medium | The number of ova | The number of two-cell eggs | Fertilization rate (%) |
|---|---|---|---|
| TYH culture medium | 5 | 2 | 40 |
| Compound #5-containing TYH culture medium | 11 | 11 | 100 |

Sperms move forwardly by flagella through the use of ATP produced by mitochondria. The effect of the compound group of the present invention (compound #5) on sperms having decreased fertilization function was studied by inhibiting such mitochondrial function.

Semination using sperms precultured in a culture medium containing FCCP, an uncoupler, had a fertilization rate of 30%, which was confirmed to be lower than that (47.4%) of semination using sperms precultured in a culture medium free from FCCP (see Table 2). On the other hand, preculture of sperms in a FCCP-containing culture medium supplemented with compound #5 recovered the fertilization rate to 50% (see Table 2).

The results indicate that the compound group of the present invention (compound #5) has an effect of improving the decreased fertilization function (e.g., forward motion using ATP) of sperms.

TABLE 2

| Culture medium | The number of ova | The number of two-cell eggs | Fertilization rate (%) |
|---|---|---|---|
| TYH culture medium | 19 | 9 | 47.4 |
| FCCP-containing TYH culture medium | 10 | 3 | 30 |
| Compound #5- and FCCP-containing TYH culture medium | 10 | 5 | 50 |

INDUSTRIAL APPLICABILITY

The present invention contributes to treatment of infertility.

The invention claimed is:

1. A method for increasing fertilization rate of a mammal sperm with a mammal ovum, comprising step (a) of transferring at least one collected mammal sperm into a physiological aqueous solution containing one or more compounds selected from the group consisting of compounds of the following formula ($I_0$), formula (II), and formula (III), and physiologically acceptable salts thereof when $R^3$ is OH:

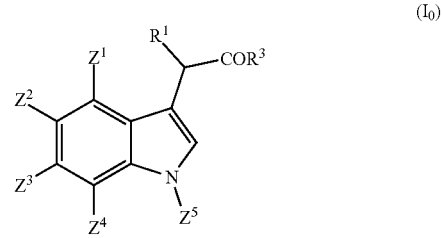

($I_0$)

[wherein $R^1$ is a benzoylmethyl group whose benzene ring is unsubstituted or a benzoylmethyl group whose benzene ring is substituted by an alkyl group having 1 to 7 carbon atoms, an alkoxyl group having 1 to 7 carbon atoms, fluorine, and/or chlorine; an unsubstituted or fluorine-substituted linear or branched alkyl group having 4 to 6 carbon atoms; or phenyl group-or cyclopentyl group-substituted methylene or ethylene; wherein the phenyl group is optionally further substituted by one or more phenyl groups, $Z^1$, $Z^2$, $Z^3$ and $Z^4$ are the same or different and each is a hydrogen atom, a halogen atom, a C1 to C6 alkyl group, a C2 to C6 alkenyl group, a C2 to C6 alkynyl group, an organic oxy group represented by $OR^8$, $R^8$ is a C1 to C7 alkyl group, a C2 to C6 alkenyl group or a C2 to C6 alkynyl group, $Z^5$ is a hydrogen atom or a C1 to C6 alkyl group, $R^3$ is any group selected from OH, $OR^4$, $NHR^4$, and $NR^4R^5$, and $R^4$ and $R^5$ are the same or different and each is a substituted or unsubstituted alkyl group having 1 to 4 carbon atoms], (II)

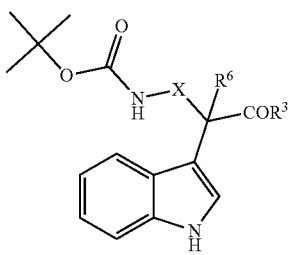

[wherein $R^6$ is hydrogen or a methyl group, X is an alkylene group having 4 to 6 carbon atoms or an ether group having 4 carbon atoms, $R^3$ is any group selected from OH, $OR^4$, $NHR^4$, and $NR^4R^5$, and $R^4$ and $R^5$ are the same or different and each is a substituted or unsubstituted alkyl group having 1 to 4 carbon atoms], and (III)

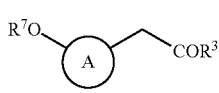

[wherein A is indole or naphthalene, and when A is indole, positions 3 and 5 of the indole are substituted by an acetic acid group and $R^7O$, respectively, and when A is naphthalene, positions 1 and 7 of the naphthalene are substituted by an acetic acid group and $R^7O$, respectively, $R^7$ is an alkyl group having 1 to 5 carbon atoms or a benzyl group, wherein the benzene ring of the benzyl group is optionally substituted by one or more alkyl groups having 1 to 3 carbon atoms or alkoxyl groups having 1 to 3 carbon atoms, $R^3$ is any group selected from OH, $OR^4$, $NHR^4$, and $NR^4R^5$, and $R^4$ and $R^5$ are the same or different and each is a substituted or unsubstituted alkyl group having 1 to 4 carbon atoms].

2. The method according to claim 1, wherein the compound is a compound of the following formula (I-2):

(I-2)

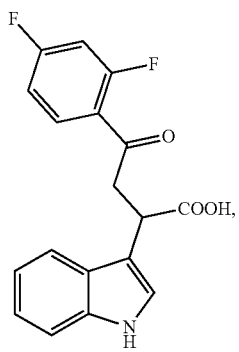

or a physiologically acceptable salt thereof.

3. A method for preparing a mammal fertilized egg, comprising step (a) of transferring at least one collected mammal sperm into a physiological aqueous solution containing one or more compounds selected from the group consisting of compounds of the following formula ($I_0$), formula (II), and formula (III), and physiologically acceptable salts thereof when $R^3$ is OH:

($I_0$)

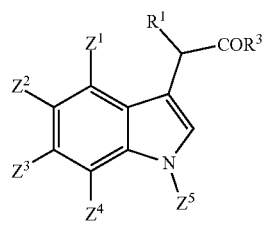

[wherein $R^1$ is a benzoylmethyl group whose benzene ring is unsubstituted or a benzoylmethyl group whose benzene ring is substituted by an alkyl group having 1 to 7 carbon atoms, an alkoxyl group having 1 to 7 carbon atoms, fluorine, and/or chlorine; an unsubstituted or fluorine-substituted linear or branched alkyl group having 4 to 6 carbon atoms; or phenyl group-or cyclopentyl group-substituted methylene or ethylene; wherein the phenyl group is optionally further substituted by one or more phenyl groups, $Z^1$, $Z^2$, $Z^3$ and $Z^4$ are the same or different and each is a hydrogen atom, a halogen atom, a C1 to C6 alkyl group, a C2 to C6 alkenyl group, a C2 to C6 alkynyl group, an organic oxy group represented by $OR^8$, $R^8$ is a C1 to C7 alkyl group, a C2 to C6 alkenyl group or a C2 to C6 alkynyl group, $Z^5$ is a hydrogen atom or a C1 to C6 alkyl group, $R^3$ is any group selected from OH, $OR^4$, $NHR^4$, and $NR^4R^5$, and $R^4$ and $R^5$ are the same or different and each is a substituted or unsubstituted alkyl group having 1 to 4 carbon atoms], (II)

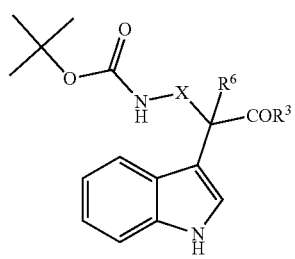

[wherein $R^6$ is hydrogen or a methyl group, X is an alkylene group having 4 to 6 carbon atoms or an ether group having 4 carbon atoms, $R^3$ is any group selected from OH, $OR^4$, $NHR^4$, and $NR^4R^5$, and $R^4$ and $R^5$ are the same or different and each is a substituted or unsubstituted alkyl group having 1 to 4 carbon atoms], and (III)

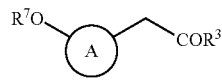

[wherein A is indole or naphthalene, and when A is indole, positions 3 and 5 of the indole are substituted by an acetic acid group and $R^7O$, respectively, and when A is naphthalene, positions 1 and 7 of the naphthalene are substituted by an acetic acid group and R⁷O, respectively, R⁷ is an alkyl group having 1 to 5 carbon atoms or a benzyl group, wherein the benzene ring of the benzyl group is optionally substituted by one or more alkyl groups having 1 to 3 carbon atoms or alkoxyl groups having 1 to 3 carbon atoms, R³ is any group selected from OH, OR⁴, NHR⁴, and NR⁴R⁵, and R⁴ and R⁵ are the same or different and each is a substituted or unsubstituted alkyl group having 1 to 4 carbon atoms];
and step (b-1) of culturing the mammal sperm of after step (a) in a culture medium containing at least one collected mammal ovum.

4. A method for preparing a mammal fertilized egg, comprising step (b-2) of culturing at least one collected mammal sperm and at least one collected mammal ovum in a culture medium containing one or more compounds selected from the group consisting of compounds of the following formula (I₀), formula (II), and formula (III), and physiologically acceptable salts thereof when R³ is OH:

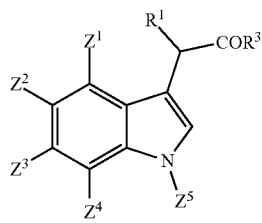

(I₀)

[wherein R¹ is a benzoylmethyl group whose benzene ring is unsubstituted or a benzoylmethyl group whose benzene ring is substituted by an alkyl group having 1 to 7 carbon atoms, an alkoxyl group having 1 to 7 carbon atoms, fluorine, and/or chlorine; an unsubstituted or fluorine-substituted linear or branched alkyl group having 4 to 6 carbon atoms; or phenyl group-or cyclopentyl group-substituted methylene or ethylene; wherein the phenyl group is optionally further substituted by one or more phenyl groups, Z¹, Z², Z³ and Z⁴ are the same or different and each is a hydrogen atom, a halogen atom, a C1 to C6 alkyl group, a C2 to C6 alkenyl group, a C2 to C6 alkynyl group, an organic oxy group represented by OR⁸, R⁸ is a C1 to C7 alkyl group, a C2 to C6 alkenyl group or a C2 to C6 alkynyl group, Z⁵ is a hydrogen atom or a C1 to C6 alkyl group, R³ is any group selected from OH, OR⁴, NHR⁴, and NR⁴R⁵, and R⁴ and R⁵ are the same or different and each is a substituted or unsubstituted alkyl group having 1 to 4 carbon atoms],

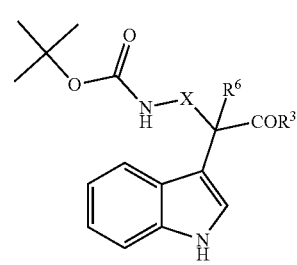

(II)

[wherein R⁶ is hydrogen or a methyl group, X is an alkylene group having 4 to 6 carbon atoms or an ether group having 4 carbon atoms, R³ is any group selected from OH, OR⁴, NHR⁴, and NR⁴R⁵, and R⁴ and R⁵ are the same or different and each is a substituted or unsubstituted alkyl group having 1 to 4 carbon atoms], and

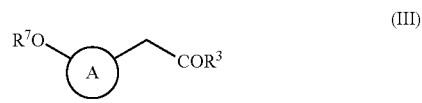

(III)

[wherein A is indole or naphthalene, and when A is indole, positions 3 and 5 of the indole are substituted by an acetic acid group and R⁷O, respectively, and when A is naphthalene, positions 1 and 7 of the naphthalene are substituted by an acetic acid group and R⁷O, respectively, R⁷ is an alkyl group having 1 to 5 carbon atoms or a benzyl group, wherein the benzene ring of the benzyl group is optionally substituted by one or more alkyl groups having 1 to 3 carbon atoms or alkoxyl groups having 1 to 3 carbon atoms, R³ is any group selected from OH, OR⁴, NHR⁴, and NR⁴R⁵, and R⁴ and R⁵ are the same or different and each is a substituted or unsubstituted alkyl group having 1 to 4 carbon atoms].

5. The method for preparing a mammal fertilized egg according to claim 4,
wherein the compound is a compound of the following formula (I-2)

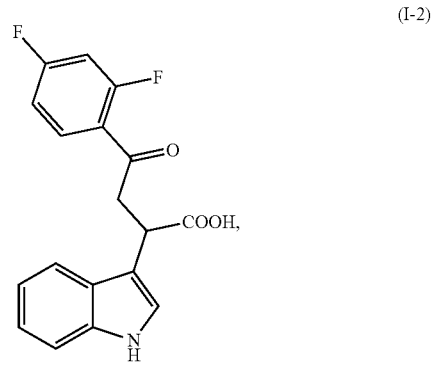 [SMILES: O=C(CC(C(=O)O)c1c[nH]c2ccccc12)c1ccc(F)cc1F]

(I-2)

or a physiologically acceptable salt thereof.

6. The method for preparing a mammal fertilized egg according to claim 3,
wherein the compound is a compound of the following formula (I-2)

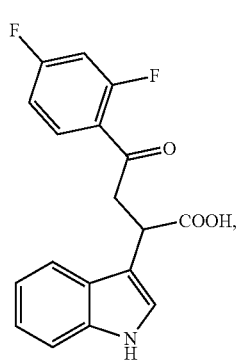
(I-2)
or a physiologically acceptable salt thereof.
* * * * *